(12) United States Patent
Lee et al.

(10) Patent No.: US 9,911,925 B2
(45) Date of Patent: Mar. 6, 2018

(54) CARBAZOLE-BASED COMPOUND AND ORGANIC LIGHT-EMITTING DEVICE INCLUDING THE SAME

(71) Applicants: Samsung Electronics Co., Ltd., Suwon-si, Gyeonggi-do (KR); Samsung SDI Co., Ltd., Yongin-si, Gyeonggi-do (KR)

(72) Inventors: Banglin Lee, Suwon-si (KR); Sangdong Kim, Hwaseong-si (KR); Sangyeob Lee, Hwaseong-si (KR); Ohyun Kwon, Yongin-si (KR); Youngkwon Kim, Gyeongsangbuk-do (KR)

(73) Assignees: SAMSUNG ELECTRONICS CO., LTD., Gyeonggi-Do (KR); SAMSUNG SDI CO., LTD., Gyeonggi-Do (KR)

( * ) Notice: Subject to any disclaimer, the term of this patent is extended or adjusted under 35 U.S.C. 154(b) by 307 days.

(21) Appl. No.: 14/618,393

(22) Filed: Feb. 10, 2015

(65) Prior Publication Data
US 2015/0228908 A1    Aug. 13, 2015

(30) Foreign Application Priority Data
Feb. 11, 2014  (KR) .................. 10-2014-0015645

(51) Int. Cl.
*H01L 51/00* (2006.01)
*C07D 403/04* (2006.01)
(Continued)

(52) U.S. Cl.
CPC ........ *H01L 51/0067* (2013.01); *C07D 403/04* (2013.01); *C07D 403/10* (2013.01);
(Continued)

(58) Field of Classification Search
None
See application file for complete search history.

(56) References Cited

U.S. PATENT DOCUMENTS 8,247,575 B2 * 8/2012 Nomura ............... C07D 403/12
                                                    313/504
8,367,850 B2    2/2013 Ma et al.
(Continued)

FOREIGN PATENT DOCUMENTS

JP    2004071500 A * 3/2004 ............ H05B 33/14
JP    2010502689 A    1/2010
(Continued)

OTHER PUBLICATIONS

Mounggon Kim, et al. "Synthesis of 2- and 4-substituted carbazole derivatives and correlation of substitution position with photophysical properties and device performances of host materials", Organic Electronics 2013, 14, 67-73.

*Primary Examiner* — Robert S Loewe
(74) *Attorney, Agent, or Firm* — Cantor Colburn LLP

(57) ABSTRACT

A carbazole-based compound represented by Formula 1A and 1B:

(Continued)

US 9,911,925 B2
Page 2

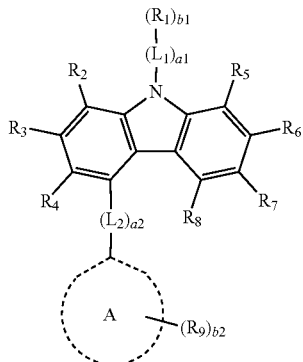

Formula 1A

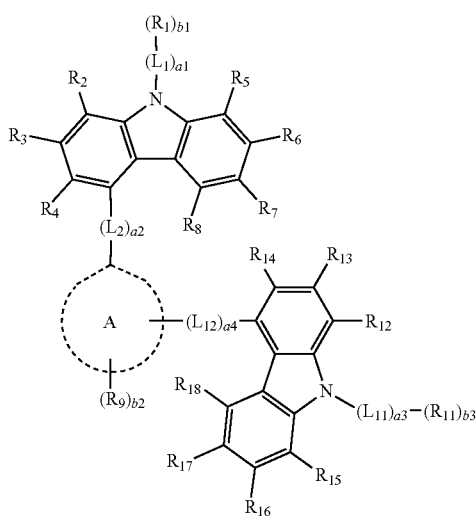

Formula 1B wherein in Formulae 1A and 1B, ring A, groups $L_1$, $L_2$, $L_{11}$, and $L_{12}$, substituents $R_1$ to $R_9$ and $R_{11}$ to $R_{18}$, and variables a1 to a4 and b1 to b3 are the same as defined in the specification.

8 Claims, 1 Drawing Sheet

(51) Int. Cl.
| | | |
|---|---|---|
| C07D 403/10 | (2006.01) | |
| C07D 409/14 | (2006.01) | |
| C07D 487/04 | (2006.01) | |
| C07D 405/14 | (2006.01) | |
| C07F 7/08 | (2006.01) | |
| C07D 495/04 | (2006.01) | |
| H01L 51/50 | (2006.01) | |
| H01L 51/52 | (2006.01) | |

(52) U.S. Cl.
CPC ......... *C07D 405/14* (2013.01); *C07D 409/14* (2013.01); *C07D 487/04* (2013.01); *C07D 495/04* (2013.01); *C07F 7/0812* (2013.01); *H01L 51/0054* (2013.01); *H01L 51/0072* (2013.01); *H01L 51/5016* (2013.01); *H01L 51/5221* (2013.01)

(56) References Cited

U.S. PATENT DOCUMENTS

| | | | | |
|---|---|---|---|---|
| 9,006,721 | B2* | 4/2015 | Lee | H01L 51/0061 257/40 |
| 2006/0183022 | A1* | 8/2006 | Takahashi | H01M 4/60 429/213 |
| 2009/0302752 | A1* | 12/2009 | Parham | C07D 209/80 313/504 |
| 2011/0057180 | A1* | 3/2011 | Ono | H01L 51/0042 257/40 |
| 2012/0175598 | A1* | 7/2012 | Balaganesan | C07D 209/88 257/40 |
| 2012/0211736 | A1 | 8/2012 | Kim et al. | |
| 2012/0223276 | A1* | 9/2012 | Parham | C07D 403/10 252/500 |
| 2013/0161603 | A1* | 6/2013 | Chung | C07F 9/657172 257/40 |
| 2016/0308142 | A1 | 10/2016 | Kim et al. | |
| 2016/0351826 | A1 | 12/2016 | Kim et al. | |
| 2017/0012216 | A1 | 1/2017 | Kim et al. | |

FOREIGN PATENT DOCUMENTS

| | | | |
|---|---|---|---|
| JP | 2012049518 A | 3/2012 | |
| JP | 2012089777 A | 5/2012 | |
| KR | 1020110048840 A | 5/2011 | |
| KR | 1020130018724 A | 2/2013 | |
| KR | 101288696 B1 | 7/2013 | |
| KR | 101395080 B1 * | 5/2014 | ........... C07D 403/10 |
| KR | 10-2015-0083786 A | 7/2015 | |
| KR | 10-2015-0083787 A | 7/2015 | |
| KR | 10-2015-0084657 A | 7/2015 | |
| WO | 03078541 A1 | 9/2003 | |
| WO | 03080760 A1 | 10/2003 | |

* cited by examiner

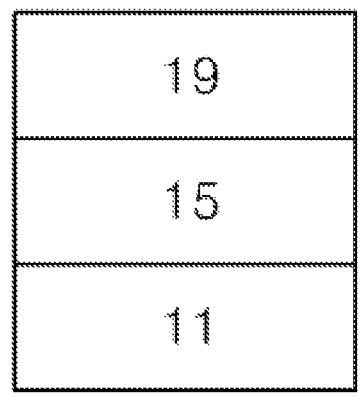

CARBAZOLE-BASED COMPOUND AND ORGANIC LIGHT-EMITTING DEVICE INCLUDING THE SAME

CROSS-REFERENCE TO RELATED APPLICATIONS

This application claims the priority to Korean Patent Application No. 10-2014-0015645, filed on Feb. 11, 2014, and all the benefits accruing therefrom under 35 U.S.C. § 119, the content of which is incorporated herein in its entirety by reference.

BACKGROUND

1. Field

One or more embodiments of the present disclosure relate to a carbazole-based compound and an organic light-emitting device including the carbazole-based compound.

2. Description of the Related Art

Organic light-emitting devices (OLEDs), which are self-emitting devices, have advantages such as wide viewing angles, excellent contrast ratios, and quick response times. In addition, OLEDs exhibit high brightness, excellent driving voltage characteristics, and can provide multicolored images.

A typical organic light-emitting device may include an anode, a cathode, and an emission layer disposed between the anode and the cathode. The organic light-emitting device may include a hole transport region between the anode and the emission layer, and an electron transport region between the emission layer and the cathode. Holes injected from the anode move to the emission layer via the hole transport region, while electrons injected from the cathode move to the emission layer via the electron transport region. Carriers such as the holes and electrons recombine in the emission layer to generate excitons. When the excitons drop from an excited state to a ground state, light is emitted.

Various types of organic light emitting devices are known. However, there still remains a need in OLEDs having low driving voltage, high efficiency, high brightness, and long lifespan.

SUMMARY

One or more embodiments of the present disclosure include a novel carbazole-based compound, and an organic light-emitting device including the same.

Additional aspects will be set forth in part in the description which follows and, in part, will be apparent from the description, or may be learned by practice of the presented embodiments.

According to one or more embodiments, a carbazole-based compound represented by Formula 1A or 1B is provided:

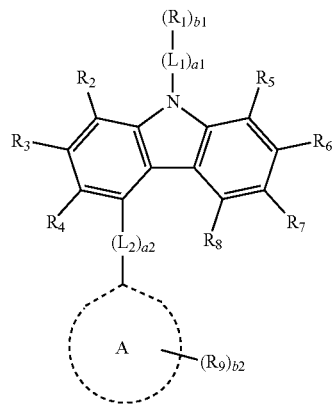

Formula 1A

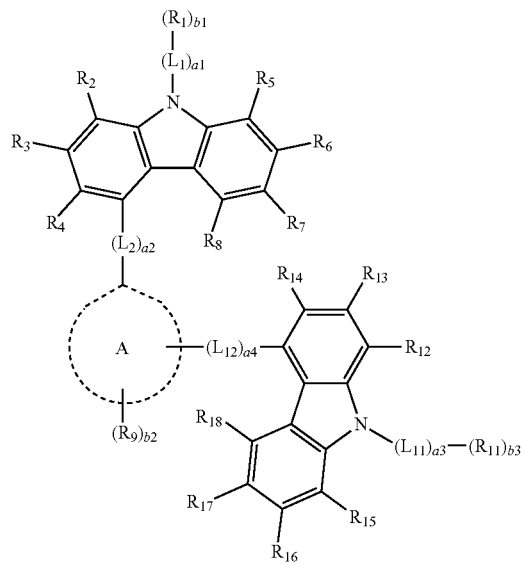

Formula 1B wherein, in Formulae 1A and 1B, ring A is a $C_2$-$C_{20}$ heterocyclic group including at least two nitrogens as ring-forming atoms and is a 6-membered ring, a 6-membered ring to which a 6-membered ring is condensed, or a 6-membered ring to which a 5-membered ring is condensed;

$L_1$, $L_2$, $L_{11}$, and $L_{12}$ are each independently selected from a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent nonaromatic condensed polycyclic group, and a substituted or unsubstituted divalent nonaromatic condensed heteropolycyclic group;

a1, a2, a3, and a4 are each independently an integer selected from 0 to 3;

$R_1$ to $R_9$, and $R_{11}$ to $R_{18}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent nonaromatic condensed polycyclic group, a substituted or unsubstituted monovalent nonaromatic condensed heteropolycyclic group, and —Si($Q_1$)($Q_2$)($Q_3$); and b1, b2, and b3 are each independently an integer selected from 1 to 5, wherein at least one of $R_5$ to $R_8$ is selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent nonaromatic condensed polycyclic group, and a substituted or unsubstituted monovalent nonaromatic condensed heteropolycyclic group;

at least one substituent of the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent nonaromatic condensed polycyclic group, the substituted divalent nonaromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent nonaromatic condensed polycyclic group, and the substituted monovalent nonaromatic condensed heteropolycyclic group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, a monovalent nonaromatic condensed heteropolycyclic group, —Si($Q_{11}$)($Q_{12}$)($Q_{13}$), and —B($Q_{14}$)($Q_{15}$), a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, and a monovalent nonaromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, and a monovalent nonaromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, a monovalent nonaromatic condensed heteropolycyclic group, —Si($Q_{21}$)($Q_{22}$)($Q_{23}$), and —B($Q_{24}$)($Q_{25}$), and —Si($Q_{31}$)($Q_{32}$)($Q_{33}$), and —B($Q_{34}$)($Q_{35}$);

wherein $Q_1$ to $Q_3$, $Q_{11}$ to $Q_{15}$, $Q_{21}$ to $Q_{25}$, and $Q_{31}$ to $Q_{35}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent nonaromatic condensed polycyclic group, and a monovalent nonaromatic condensed heteropolycyclic group.

According to one or more embodiments of the present disclosure, an organic light-emitting device includes:

a first electrode;

a second electrode; and an organic layer disposed between the first electrode and the second electrode, wherein the organic layer includes an emission layer and at least one of the carbazole-based compounds.

BRIEF DESCRIPTION OF THE DRAWINGS

These and/or other aspects will become apparent and more readily appreciated from the following description of the embodiments, taken in conjunction with the accompanying drawings in which:

FIG. 1 is a schematic view of an organic light-emitting device according to an embodiment of the present disclosure.

DETAILED DESCRIPTION

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

According to an embodiment of the present disclosure, there is provided a carbazole-based compound represented by Formula 1A or 1B:

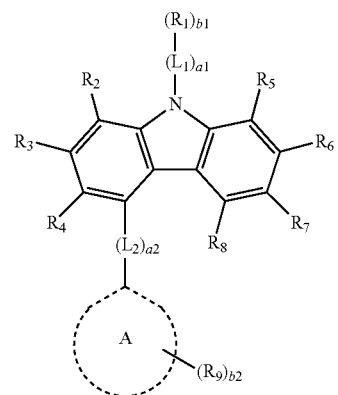

Formula 1A

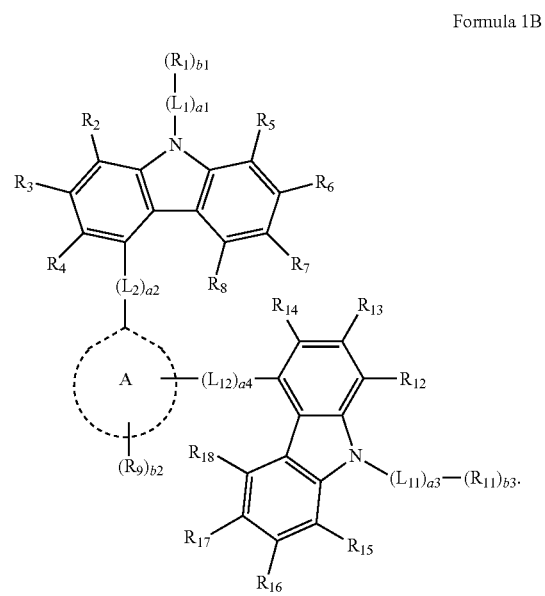

Formula 1B

In Formulae 1A and 1B, ring A may be a $C_2$-$C_{20}$ heterocyclic group including at least two nitrogens (N) as ring-forming atoms and is a 6-membered ring, a 6-membered ring to which a 6-membered ring is condensed, or a 6-membered ring to which a 5-membered ring is condensed.

For example, in Formulae 1A and 1B, ring A may be a $C_2$-$C_{20}$ heterocyclic group including at least three nitrogens as ring-forming atoms.

For example, in Formulae 1A and 1B, the ring A may be selected from groups represented by Formulae 2-1 to 2-8, but is not limited thereto:

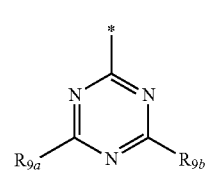

Formula 2-1

-continued

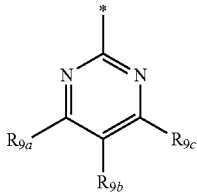

Formula 2-2

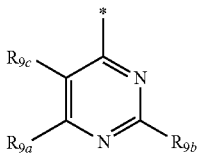

Formula 2-3

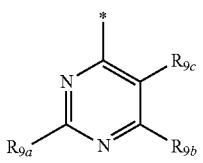

Formula 2-4

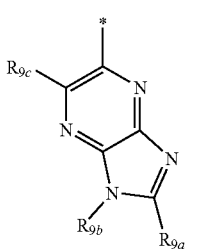

Formula 2-5

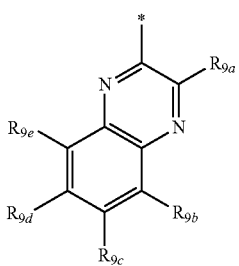

Formula 2-6

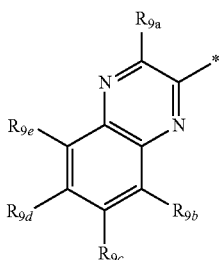

Formula 2-7

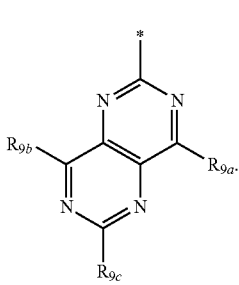

Formula 2-8

In Formulae 2-1 to 2-8,
$R_{9a}$ to $R_{9e}$ may be the same or different, and each may have the same definition as $R_9$ to be described below, and * indicates a binding site to an adjacent atom.

For example, the ring A in Formula 1A or 1B may be a group represented by one of Formulae 2-1, 2-5, and 2-8, but is not limited thereto.

Also, for example, the ring A in Formula 1A or 1B may be a group represented by one of Formulae 2-1 to 2-4, but is not limited thereto.

In Formulae 1A and 1B, $L_1$, $L_2$, $L_{11}$, and $L_{12}$ may be each independently selected from a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent nonaromatic condensed polycyclic group, and a substituted or unsubstituted divalent nonaromatic condensed heteropolycyclic group.

For example, in Formulae 1A and 1B, $L_1$, $L_2$, $L_{11}$, and $L_{12}$ may be each independently selected from:
a phenylene group, a pentalenylene group, an indenylene group, a naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, fluoranthenylene group, a triphenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, an imidazopyrimidinylene group, and an imidazopyridinylene group, and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzooxazolylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, an imidazopyrimidinylene group, and an imidazopyridinylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a $C_6$-$C_{20}$ aryl group, and a $C_2$-$C_{60}$ heteroaryl group, and groups represented by Formulae 3-1 to 3-6.

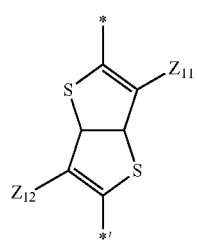

Formula 3-1

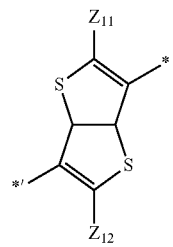

Formula 3-2

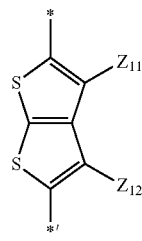

Formula 3-3

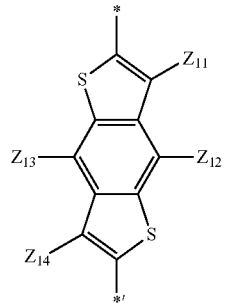

Formula 3-4

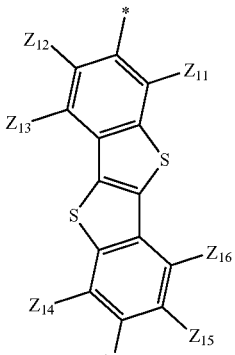

Formula 3-5

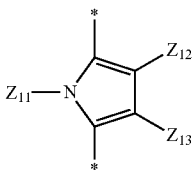

Formula 3-6

In Formulae 3-1 to 3-6, $Z_{11}$ to $Z_{16}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a $C_6$-$C_{20}$ aryl group, and a $C_2$-$C_{60}$ heteroaryl group; and

* and *' each indicate a binding site to an adjacent atom.

In some embodiments, in Formulae 1A and 1B, $L_1$, $L_2$, $L_{11}$, and $L_{12}$ may be each independently selected from, but not limited to, a phenylene group, a naphthylene group, a phenalenylene group, a phenanthrenylene group, a triphenylenylene group, an anthracenylene group, a pyrrolylene group, a pyridinylene group, a pyrazinylene group, a pyrimidinylene group, a pyridazinylene group, an isoindolylene group, an indolylene group, a furanylene group, a benzofuranylene group, a thiophenylene group, a benzothiophenylene group, and a triazinylene group, a phenylene group, a naphthylene group, a phenalenylene group, a phenanthrenylene group, a triphenylenylene group, an anthracenylene group, a pyrrolylene group, a pyridinylene group, a pyrazinylene group, a pyrimidinylene group, a pyridazinylene group, an isoindolylene group, an indolylene group, a furanylene group, a benzofuranylene group, a thiophenylene group, a benzothiophenylene group, and a triazinylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a triphenylenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group, and groups represented by Formulae 3-1 to 3-6.

In Formulae 3-1 to 3-6, $Z_{11}$ to $Z_{16}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a triphenylenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group.

For example, in Formulae 1A and 1B, $L_1$, $L_2$, $L_{11}$, and $L_{12}$ may be each independently selected from groups represented by Formulae 4-1 to 4-15, and Formulae 3-1 to 3-6, but are not limited thereto:

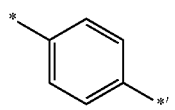

Formula 4-1

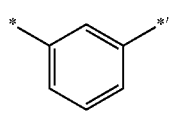

Formula 4-2

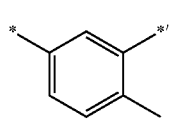

Formula 4-3

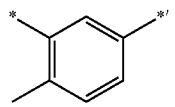

Formula 4-4

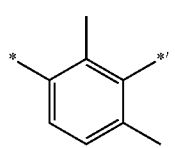

Formula 4-5

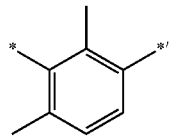

Formula 4-6

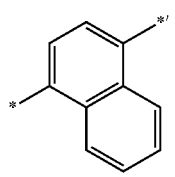

Formula 4-7

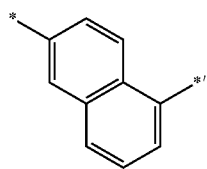

Formula 4-8

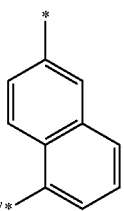

Formula 4-9

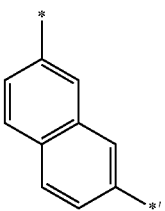

Formula 4-10

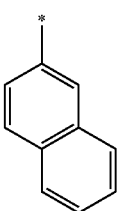

Formula 4-11

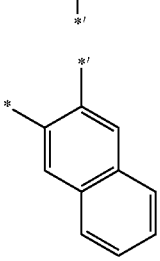

Formula 4-12

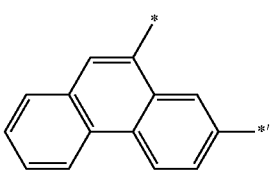

Formula 4-13

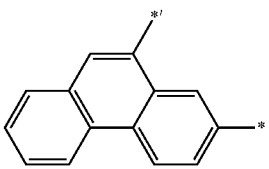

Formula 4-14

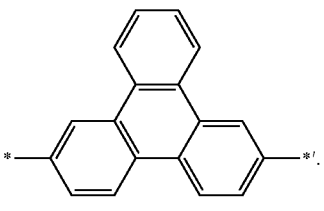

Formula 4-15

In Formula 1A, a1, which indicates the number of groups $L_1$, may be an integer selected from 0 to 3. For example, a1 may be 0, 1, or 2. When a1 is 0, $R_1$ may be directly linked to the nitrogen atom (N) of the carbazole ring. When a1 is 2 or greater, the two or more groups $L_1$ may be identical to or different from each other. Variables a2, a3, and a4 may be understood based on the description of a1 and the structures of Formulae 1A and 1B.

In Formulae 1A and 1B, a1, a2, a3, and a4 may be each independently 0, 1, or 2, but are not limited thereto.

In Formulae 1A and 1B, $R_1$ to $R_9$, and $R_{11}$ to $R_{18}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group alkynyl group, a substituted or unsubstituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent nonaromatic condensed polycyclic group, a substituted or unsubstituted monovalent nonaromatic condensed heteropolycyclic group, and —Si($Q_1$)($Q_2$)($Q_3$).

For example, in Formulae 1A and 1B, $R_1$ and $R_{11}$ may be each independently selected from a substituted or unsubstituted $C_6$-$C_{20}$ aryl group, a substituted or unsubstituted $C_2$-$C_{20}$ heteroaryl group, a substituted or unsubstituted monovalent nonaromatic condensed polycyclic group, a substituted or unsubstituted monovalent nonaromatic condensed heteropolycyclic group, and —Si($Q_1$)($Q_2$)($Q_3$);

$R_2$ to $R_9$, and $R_{12}$ to $R_{18}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{20}$ aryl group, a substituted or unsubstituted $C_2$-$C_{20}$ heteroaryl group, a substituted or unsubstituted monovalent nonaromatic condensed polycyclic group, a substituted or unsubstituted monovalent nonaromatic condensed heteropolycyclic group, and —Si($Q_1$)($Q_2$)($Q_3$); wherein at least one of $R_5$ to $R_8$ may be selected from a substituted or unsubstituted $C_6$-$C_{20}$ aryl group, a substituted or unsubstituted $C_2$-$C_{20}$ heteroaryl group, a substituted or unsubstituted monovalent nonaromatic condensed polycyclic group, and a substituted or unsubstituted monovalent nonaromatic condensed heteropolycyclic group.

In some embodiments, in Formulae 1A and 1B, $R_1$ to $R_9$, and $R_{11}$ to $R_{18}$ may be each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a imidazopyrimidinyl group, and an imidazopyridinyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, and an imidazopyridinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group, and —Si(Q₁)(Q₂)(Q₃); wherein at least one of R₅ to R₈ may be selected from:

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, and an imidazopyridinyl group, and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, and an imidazopyridinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group; and R₁ and R₁₁ may be each independently selected from, but not limited to, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, and an imidazopyridinyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, and an imidazopyridinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group, and —Si(Q₁)(Q₂)(Q₃), wherein $Q_1$ to $Q_3$ are each independently selected from a hydrogen, $C_1$-$C_{20}$ alkyl group, a $C_1$-$C_{20}$ alkoxy group, a phenyl group, a naphthyl group, an anthracenyl group, a pyrenyl group, a phenanthrenyl group, a triphenylenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group.

In some embodiments, in Formulae 1A and 1B, $R_1$ and $R_{11}$ may be each independently selected from groups represented by Formulae 5-1 to 5-40, and —Si($Q_1$)($Q_2$)($Q_3$), wherein $Q_1$ to $Q_3$ may be each independently selected from a hydrogen, $C_1$-$C_{20}$ alkyl group, a $C_1$-$C_{20}$ alkoxy group, a phenyl group, a naphthyl group, an anthracenyl group, a pyrenyl group, a phenanthrenyl group, a triphenylenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group;

$R_2$ to $R_4$, and $R_{11}$ to $R_{14}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

$R_5$ to $R_9$, and $R_{15}$ to $R_{18}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, and groups represented by Formulae 5-1 to 5-40; wherein at least one of $R_5$ to $R_8$, and at least one of $R_{15}$ to $R_{18}$ may be each independently selected from groups represented by Formulae 5-1 to 5-40; and at least one of groups $R_9$ is selected from groups represented by Formulae 5-1 to 5-40. However, embodiments of the present disclosure are not limited thereto.

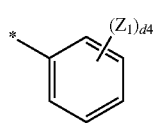

Formula 5-1

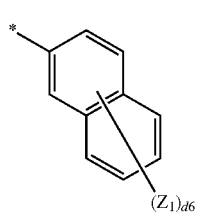

Formula 5-2

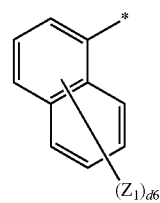

Formula 5-3

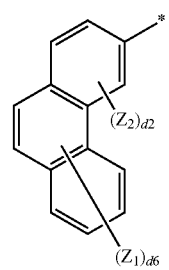

Formula 5-4

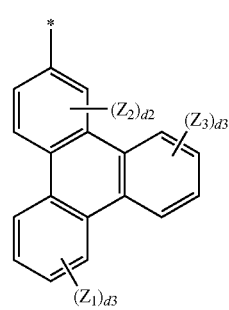

Formula 5-5

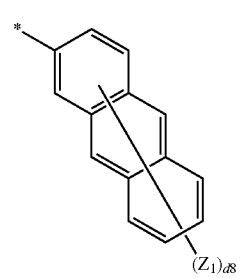

Formula 5-6

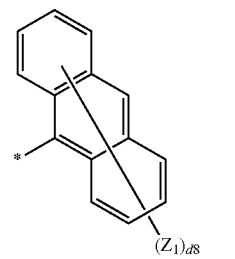

Formula 5-7

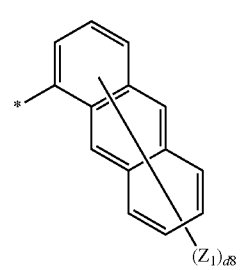

Formula 5-8

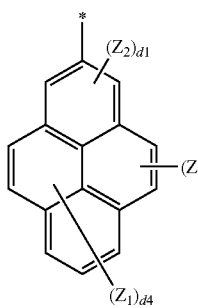
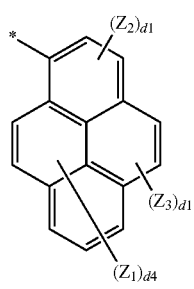
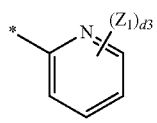
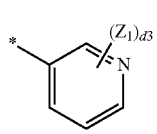
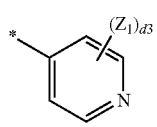
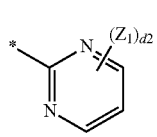
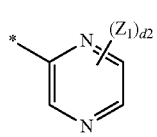
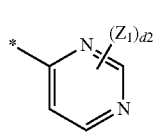
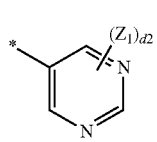
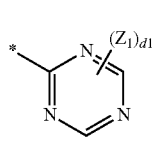
Formula 5-9
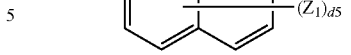
Formula 5-10
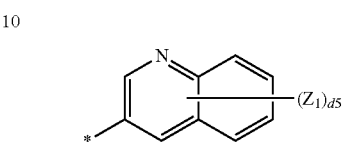
Formula 5-11
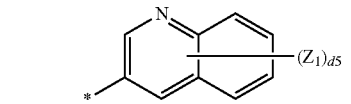
Formula 5-12
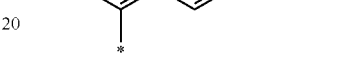
Formula 5-13
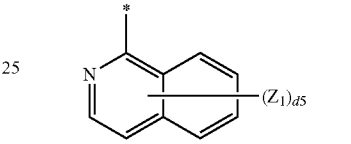
Formula 5-14
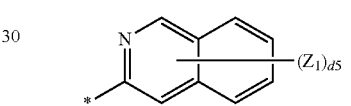
Formula 5-15
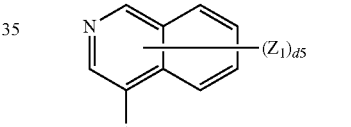
Formula 5-16
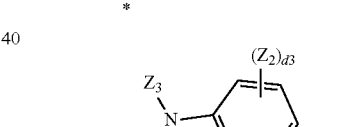
Formula 5-17
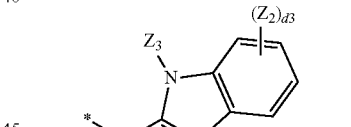
Formula 5-18
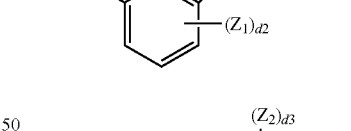
Formula 5-19
Formula 5-20
Formula 5-21
Formula 5-22
Formula 5-23
Formula 5-24
Formula 5-25
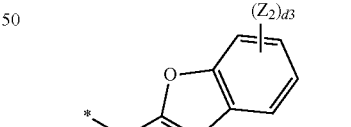
Formula 5-26
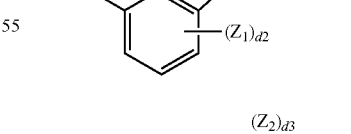
Formula 5-27
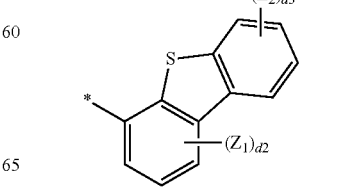

Formula 5-28 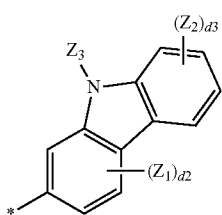
Formula 5-29 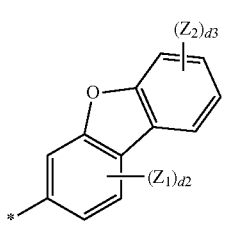
Formula 5-30 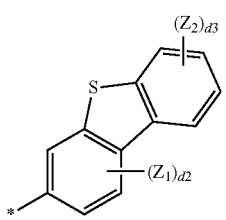
Formula 5-31 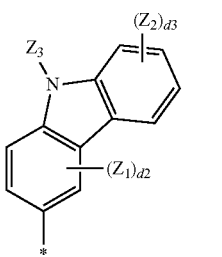
Formula 5-32 
Formula 5-33 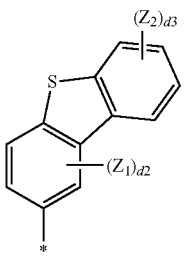
Formula 5-34 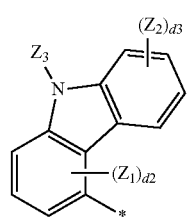
Formula 5-35 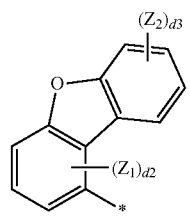
Formula 5-36 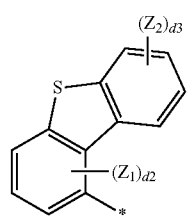
Formula 5-37 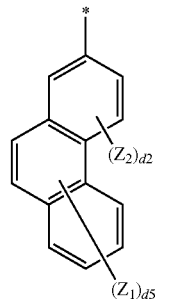
Formula 5-38 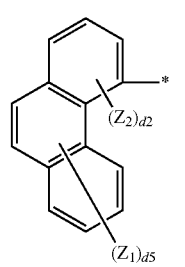
Formula 5-39 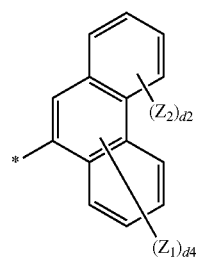

-continued

Formula 5-40

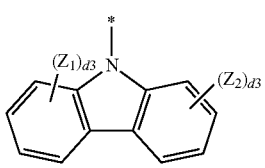

In Formulae 5-1 to 5-40, $Z_1$ to $Z_3$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group;

d1 may be 1 or 2;
d2 may be an integer selected from 1 to 3;
d3 may be an integer selected from 1 to 4;
d4 may be an integer selected from 1 to 5;
d5 may be an integer selected from 1 to 6;
d6 may be an integer selected from 1 to 7;
d7 may be an integer selected from 1 to 8; and
d8 may be an integer selected from 1 to 9;
* indicates a binding site to an adjacent atom.

In some embodiments, in Formulae 1A and 1B, $R_1$ to $R_8$, and $R_{11}$ to $R_{18}$ may be each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group, a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof, a phenyl group, a naphthyl group, an anthracenyl group, a triphenylenyl group, a pyrenyl group, a phenanthrenyl group, a phenylenyl group, a fluorenyl group, a carbazolyl group, a dibenzofuranyl group, and a dibenzothiophenyl group, a phenyl group, a naphthyl group, an anthracenyl group, a triphenylenyl group, a pyrenyl group, a phenanthrenyl group, a phenylenyl group, a fluorenyl group, a carbazolyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a phenylenyl group, a fluorenyl group, a carbazolyl group, a dibenzofuranyl group, and a dibenzothiophenyl group, and —Si($Q_1$)($Q_2$)($Q_3$), wherein $Q_1$ to $Q_3$ may be each independently selected from a hydrogen, $C_1$-$C_{20}$ alkyl group, a $C_1$-$C_{20}$ alkoxy group, a phenyl group, a naphthyl group, an anthracenyl group, a pyrenyl group, a phenanthrenyl group, a triphenylenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group; wherein at least one of $R_5$ to $R_8$, and at least one of $R_{15}$ to $R_{18}$ may be each independently selected from, but not limited to, a phenyl group, a naphthyl group, an anthracenyl group, a triphenylenyl group, a pyrenyl group, a phenanthrenyl group, a phenylenyl group, a fluorenyl group, a carbazolyl group, a dibenzofuranyl group, and a dibenzothiophenyl group, and a phenyl group, a naphthyl group, an anthracenyl group, a triphenylenyl group, a pyrenyl group, a phenanthrenyl group, a phenylenyl group, a fluorenyl group, a carbazolyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyrenyl group, a phenanthrenyl group, a phenylenyl group, a fluorenyl group, a carbazolyl group, a dibenzofuranyl group, and a dibenzothiophenyl group.

In Formulae 1A and 1B, b1, which indicates the number of substituents $R_1$, may be an integer selected from 1 to 5. For example, b1 may be 1 or 2.

In Formulae 1A and 1B, b2, which indicates the number of substituents $R_9$, may be an integer selected from 1 to 5. For example, b2 may be 1 or 2.

In Formulae 1A and 1B, b3, which indicates the number of substituents $R_{11}$, may be an integer selected from 1 to 5. For example, b3 may be 1 or 2.

In some embodiments, at least one of substituents $R_9$ may be selected from a substituted or unsubstituted $C_6$-$C_{60}$ aryl group, a substituted or unsubstituted $C_2$-$C_{60}$ heteroaryl group, a substituted or unsubstituted monovalent nonaromatic condensed polycyclic group, and a substituted or unsubstituted monovalent nonaromatic condensed heteropolycyclic group.

For example, at least one of $R_{9a}$ and $R_{9b}$ in Formula 2-1, at least one of $R_{9a}$ to $R_{9c}$ in Formulae 2-2 to 2-5, and 2-8, and at least one of $R_{9a}$ to $R_{9e}$ in Formulae 2-6, 2-7, and 2-9 to 2-16 may be selected from a substituted or unsubstituted $C_6$-$C_{60}$ aryl group, a substituted or unsubstituted $C_2$-$C_{60}$ heteroaryl group, a substituted or unsubstituted monovalent nonaromatic condensed polycyclic group, and a substituted or unsubstituted monovalent nonaromatic condensed heteropolycyclic group.

For example, in Formulae 1A and 1B, each of b1, b2, and b3 may be 1. However, embodiments of the present disclosure are not limited thereto.

For example, in Formula 1B, $L_1$=$L_{11}$, $L_2$=$L_{12}$, a1=a3, a2=a4, $R_1$=$R_{11}$, $R_2$=$R_{12}$, $R_3$=$R_{13}$, $R_4$=$R_{14}$, $R_5$=$R_{15}$, $R_6$=$R_{16}$, $R_7$=$R_{17}$, $R_8$=$R_{18}$, and b1=b3. However, embodiments of the present disclosure are not limited thereto.

In some embodiments, the carbazole-based compound may be represented by Formula 1A in which a1 is 0;
$R_1$ is selected from Formulae 5-1 to 5-40 (for example, $R_1$ may be represented by Formula 5-1);
b1 is 0;
$R_2$ to $R_6$ and $R_8$ are a hydrogen;
$R_7$ is selected from Formulae 5-1 to 5-40 (for example, $R_7$ may be represented by Formula 5-40); a2 is 0 or 1;
$L_2$ is selected from Formulae 4-1 to 4-15 (for example, $L_2$ may be represented by Formula 4-2);
ring A is represented Formula 2-1 (wherein, in Formula 2-1, $R_{9a}$ and $R_{9b}$ may be each independently, selected from Formulae 5-1 to 5-40, and, for example, $R_{9a}$ and $R_{9b}$ may be represented by Formula 5-1).

In other embodiments, the carbazole-based compound may be represented by Formula 1A in which a1 is 0;
$R_1$ is represented by Formula 5-1;
b1 is 0;
$R_2$ to $R_6$ and $R_8$ are a hydrogen;
$R_7$ is represented by Formula 5-40; a2 is 0 or 1;
$L_2$ is represented by Formula 4-2;
ring A is represented Formula 2-1 (wherein, in Formula 2-1, $R_{9a}$ and $R_{9b}$ is represented by Formula 5-1).

In some embodiments, the carbazole-based compound of Formula 1A or 1B may be one of Compounds 1 to 130.

1

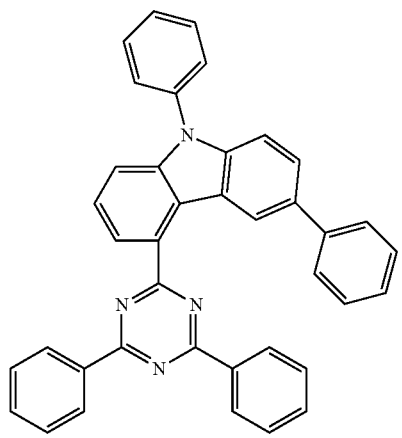

2

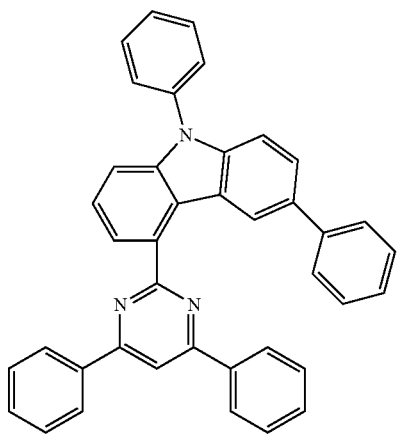

3

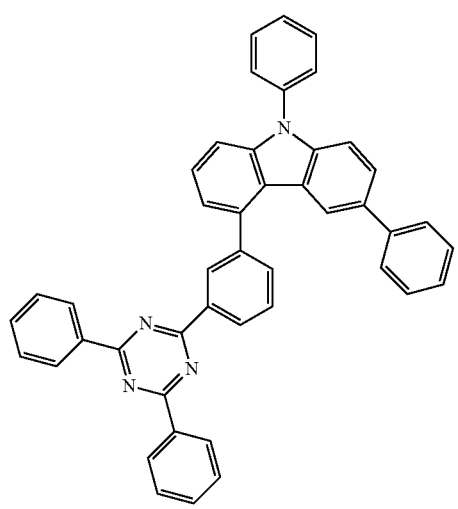

4

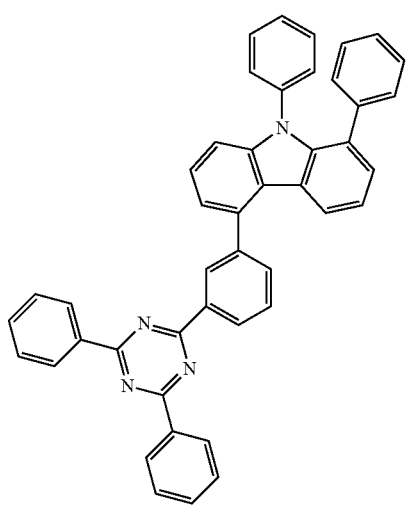

-continued
5
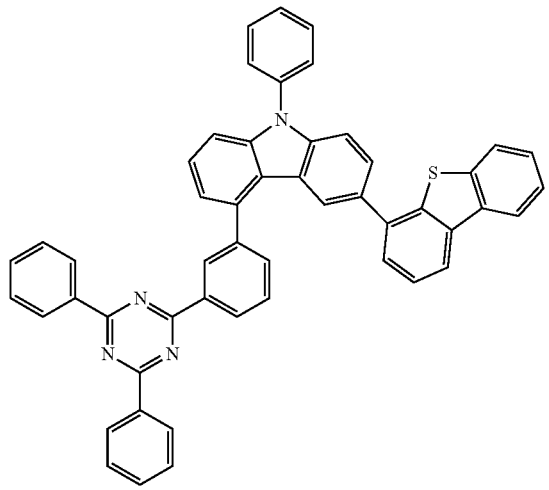
6
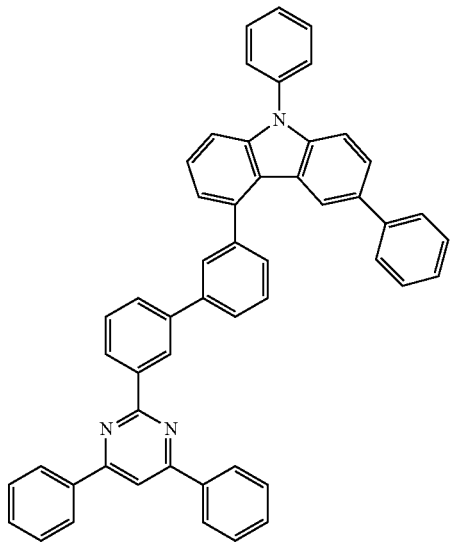
7
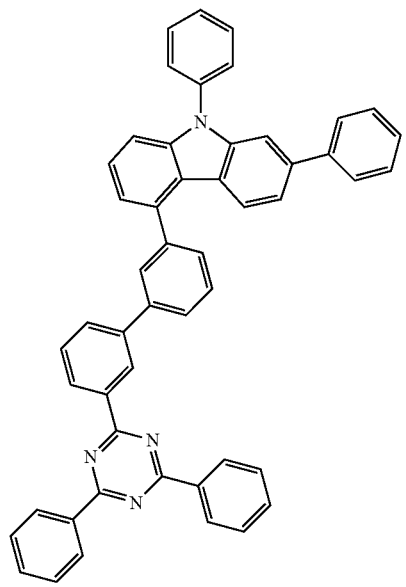
8
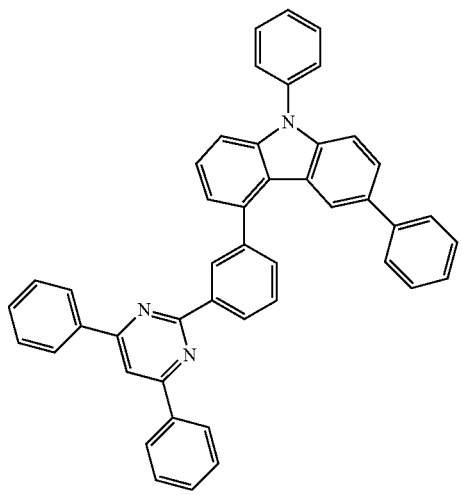

-continued
9
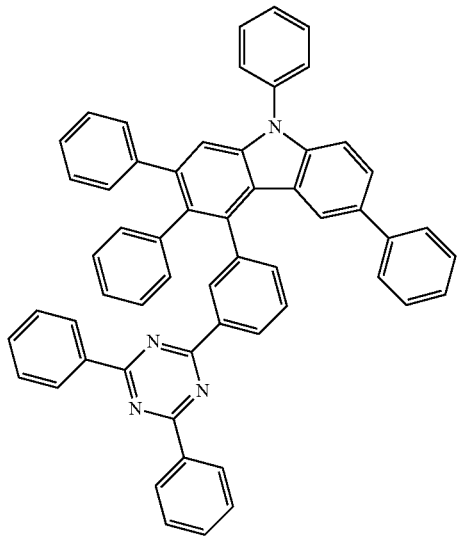
10
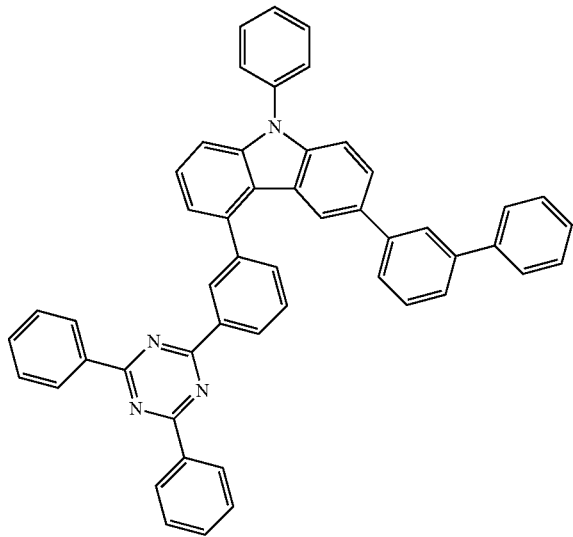
11
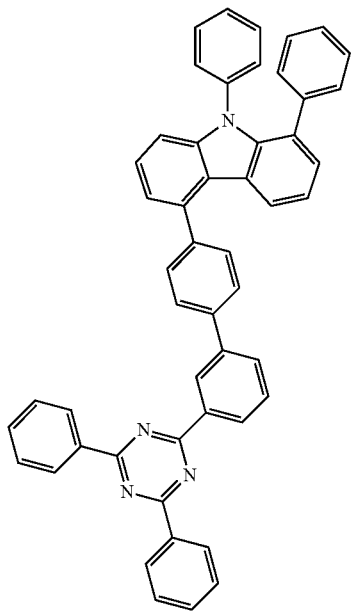
12
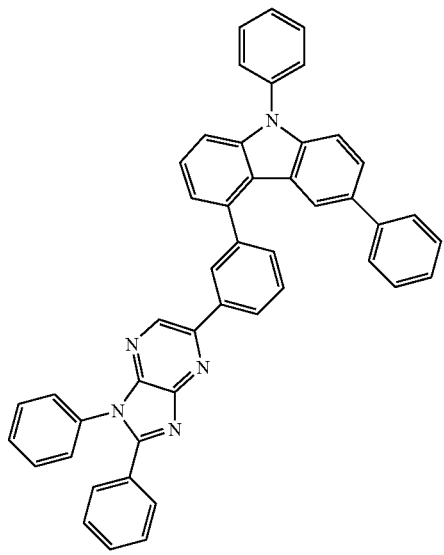

-continued
13
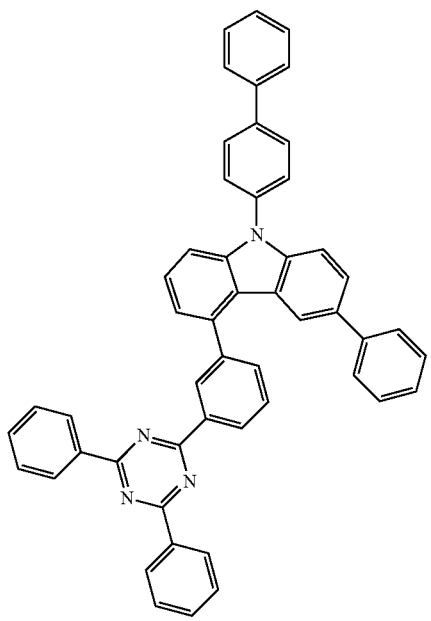
14
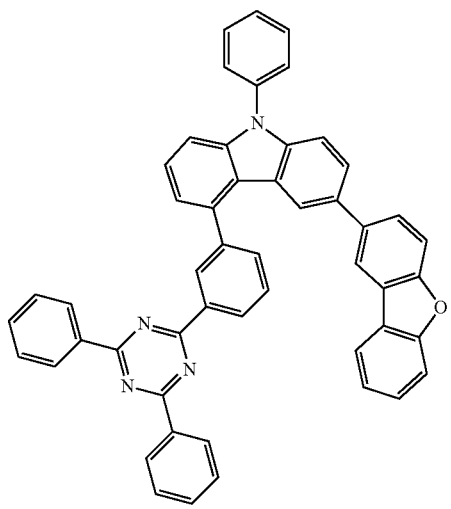
15
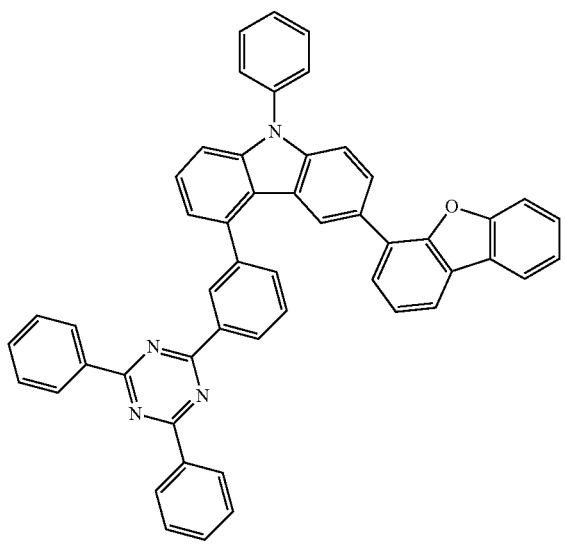
16
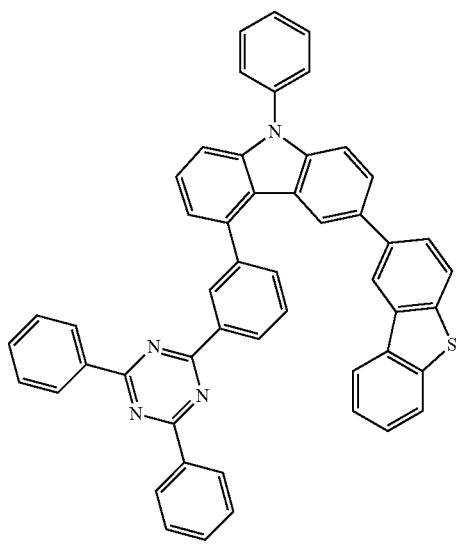

-continued
17
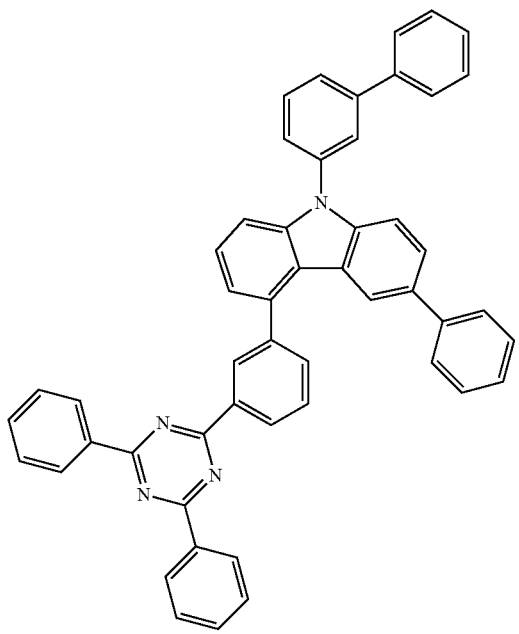
18
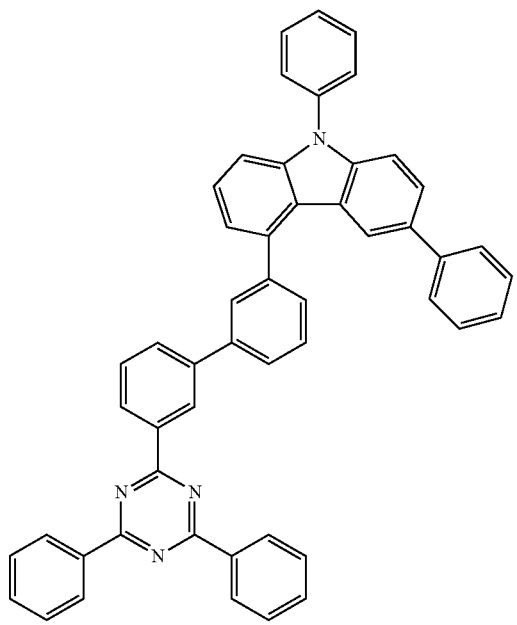
19
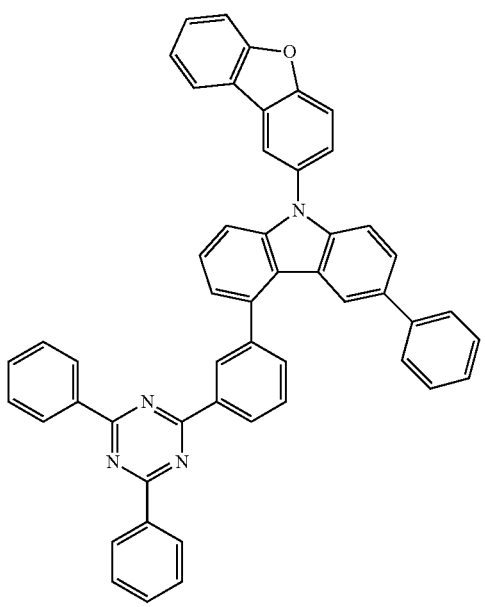
20
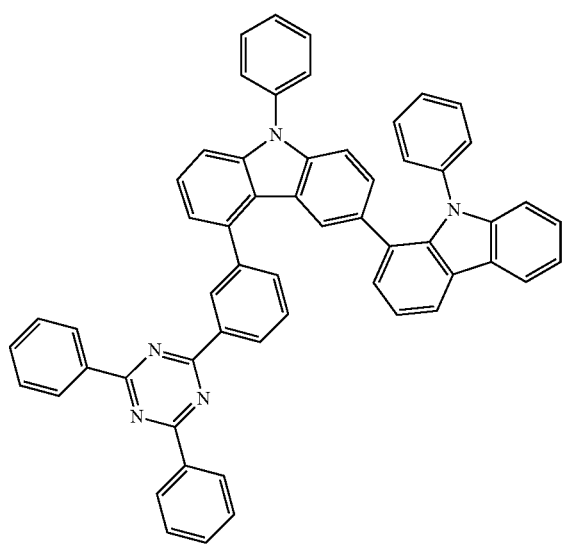

-continued
21
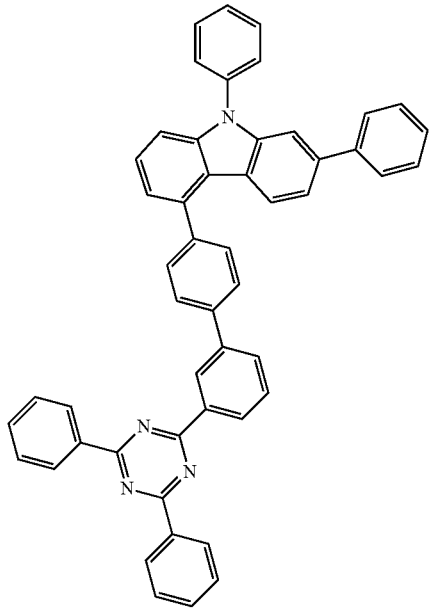
22
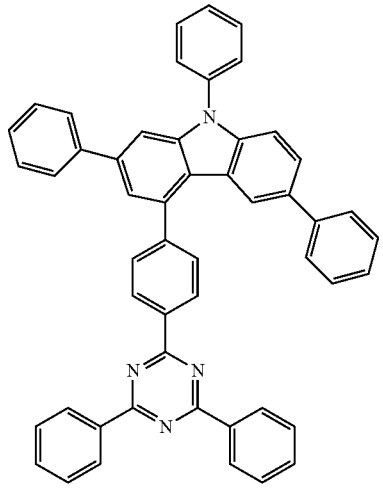
23
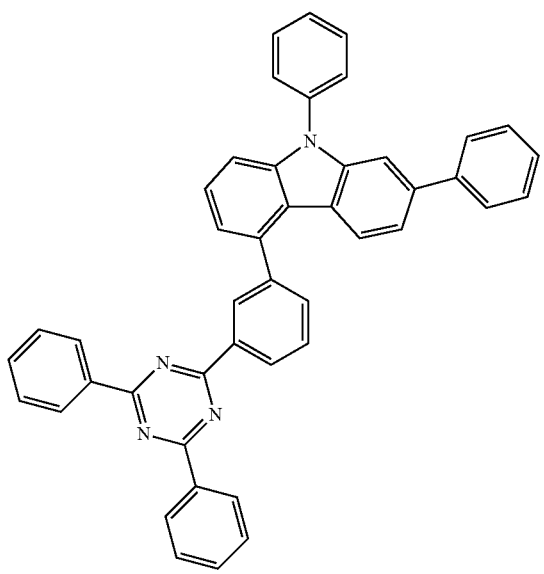
24
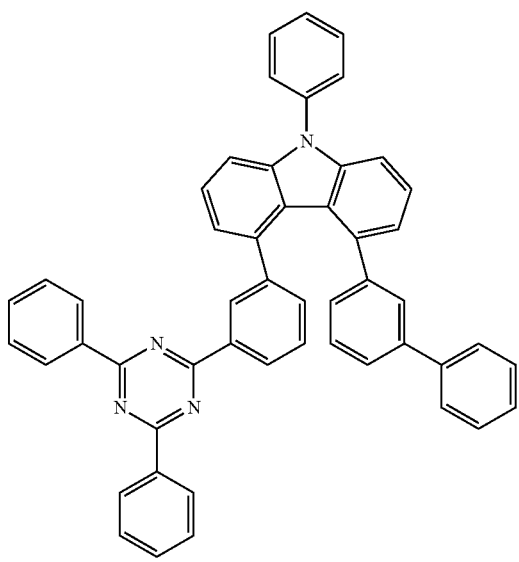

-continued
25
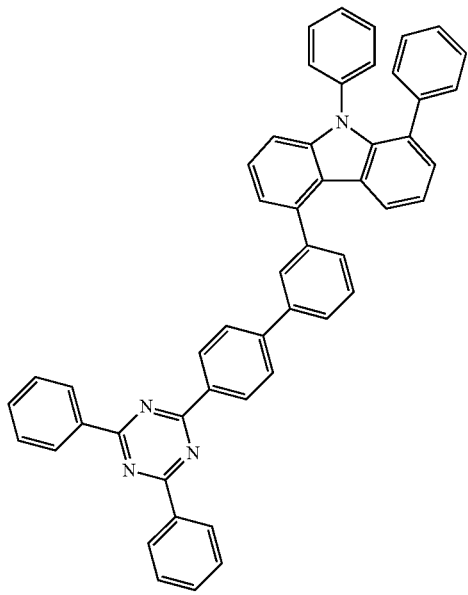
26
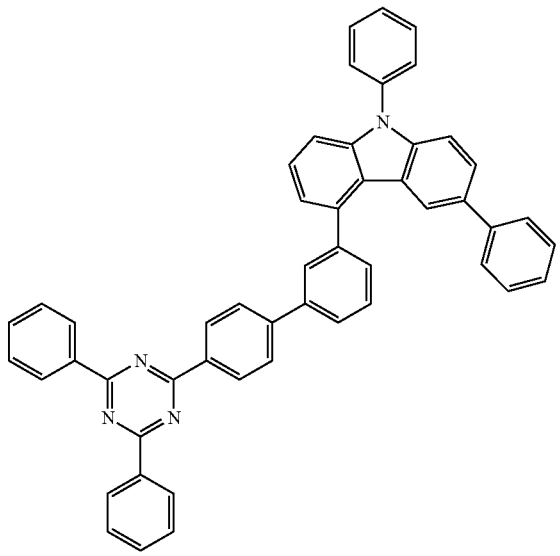
27
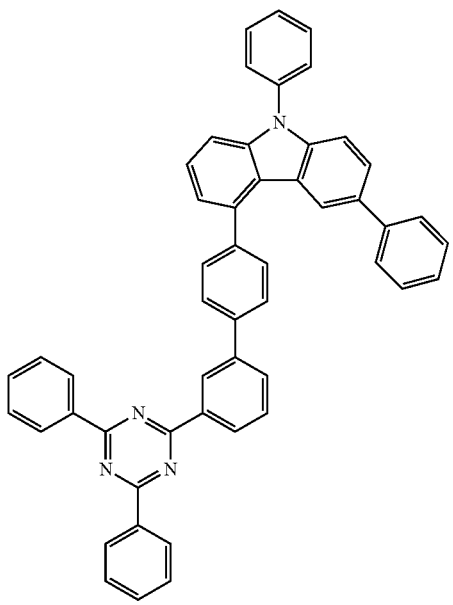
28
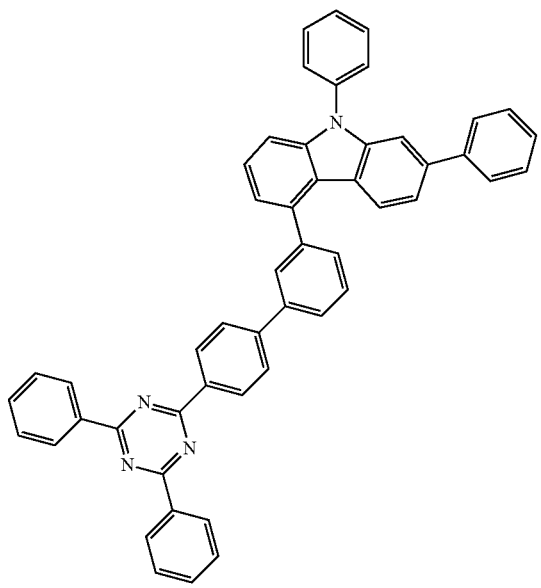

-continued
29
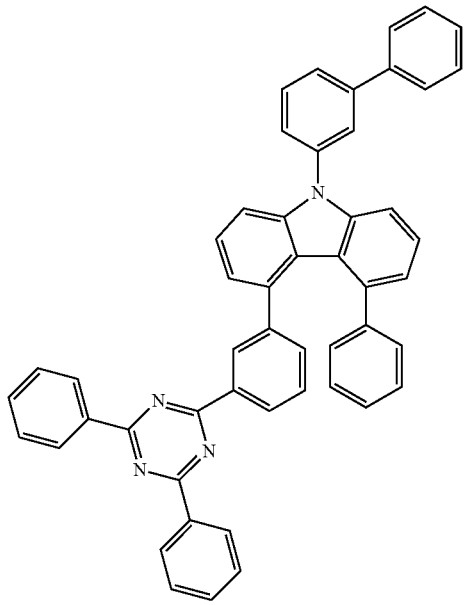
30
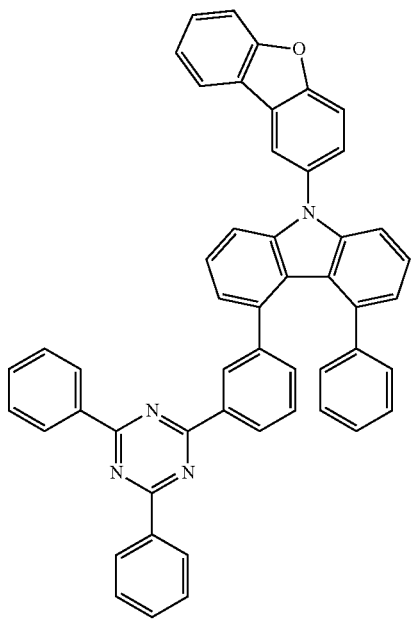
31
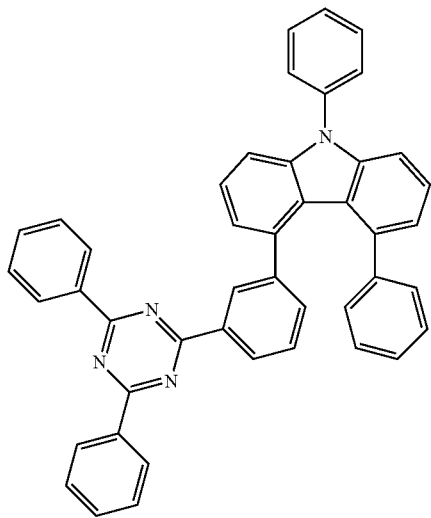
32
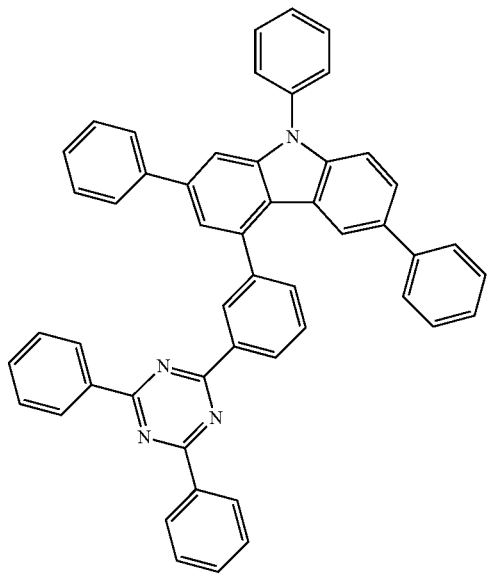

33
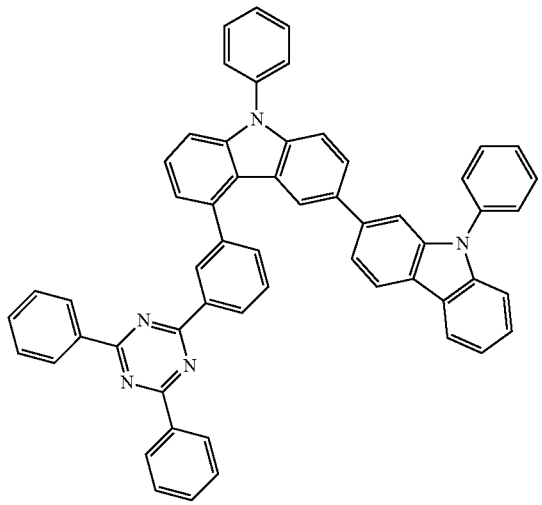
34
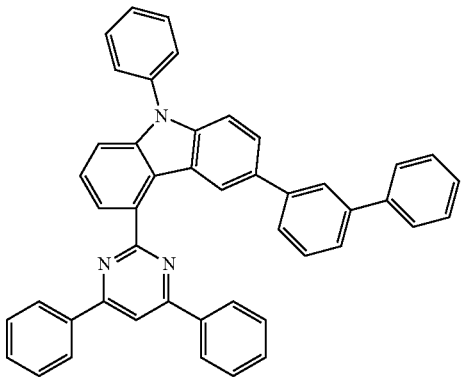
35
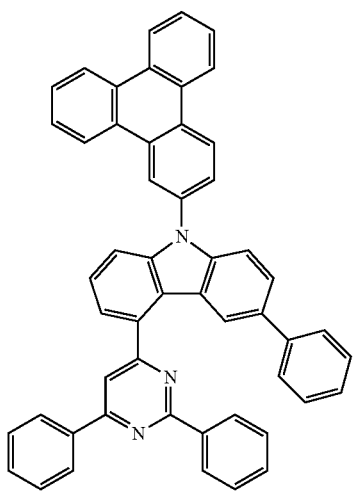
36
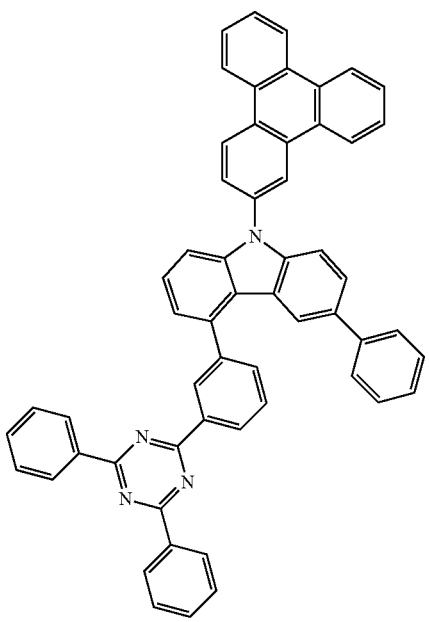

37
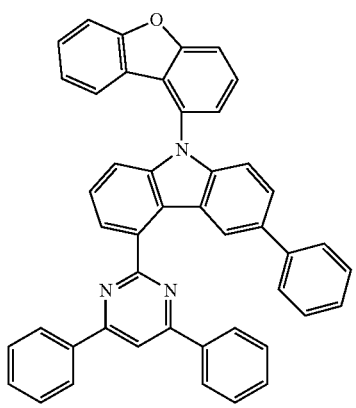
38
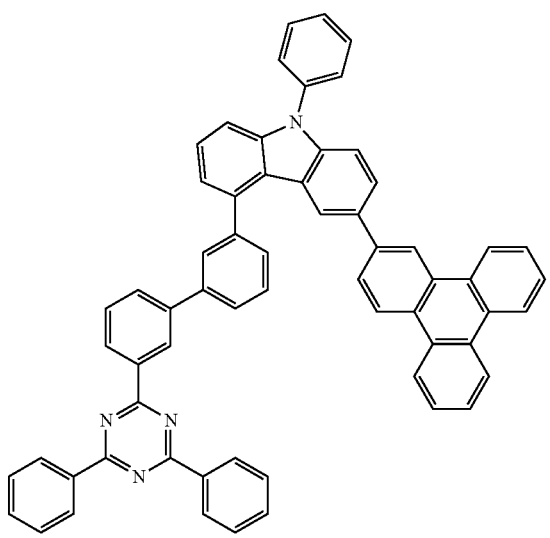
39
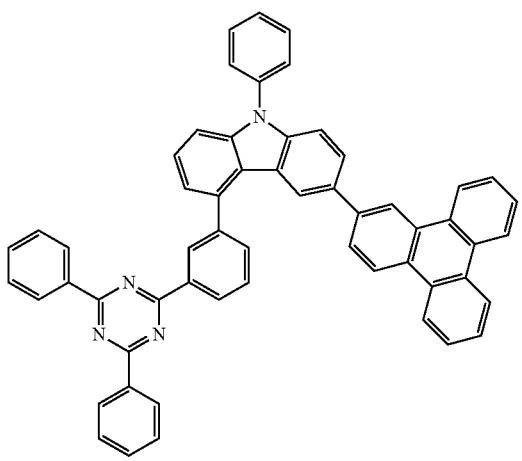
40
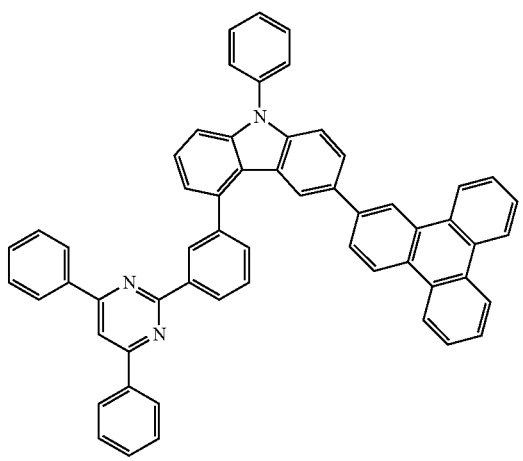
41
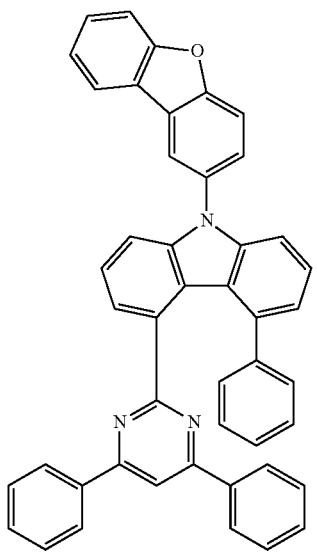
42
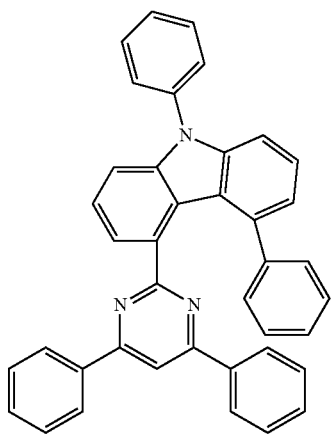

-continued
43
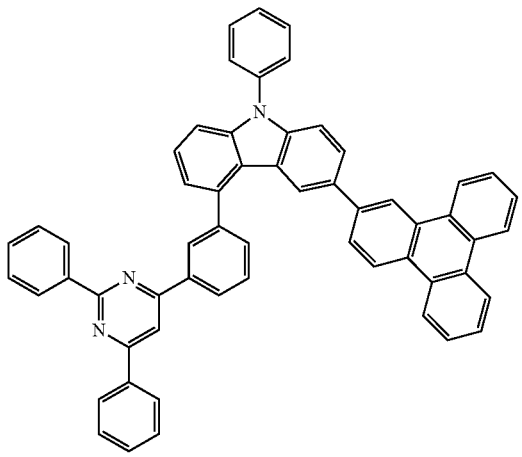
44
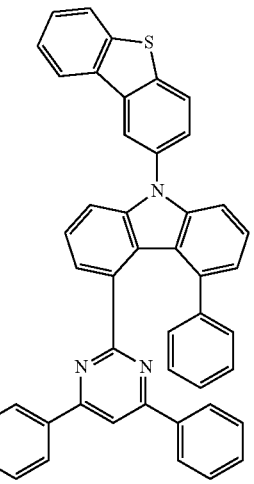
45
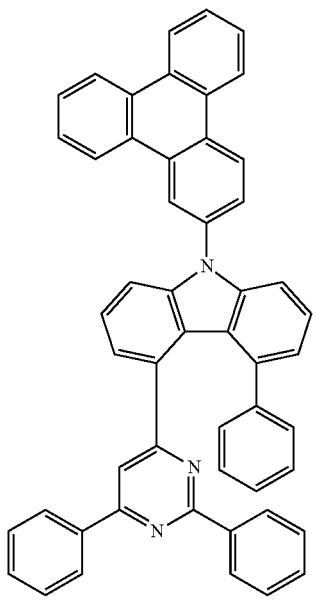
46
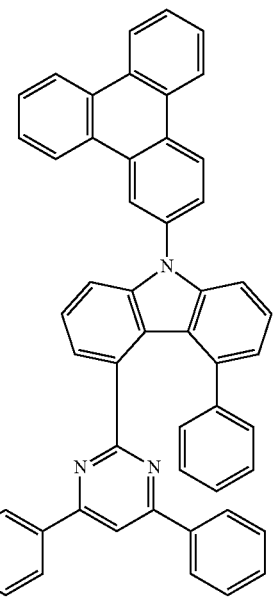
47
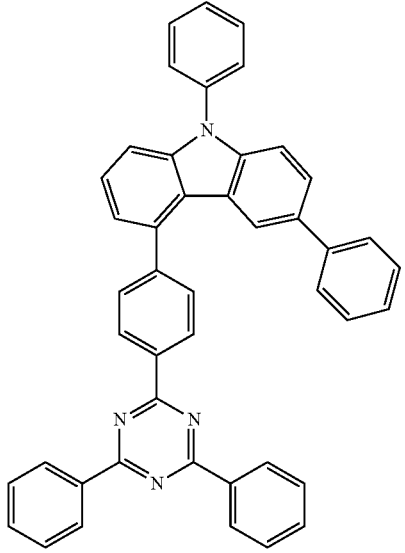
48
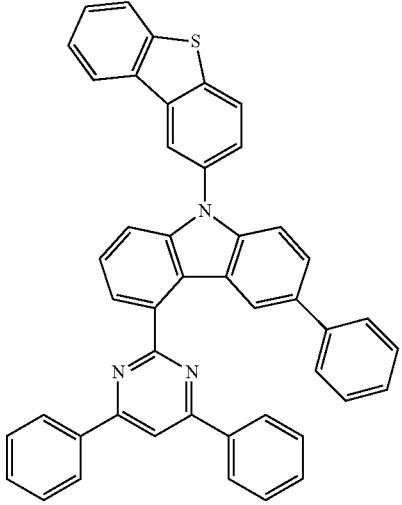

-continued
49
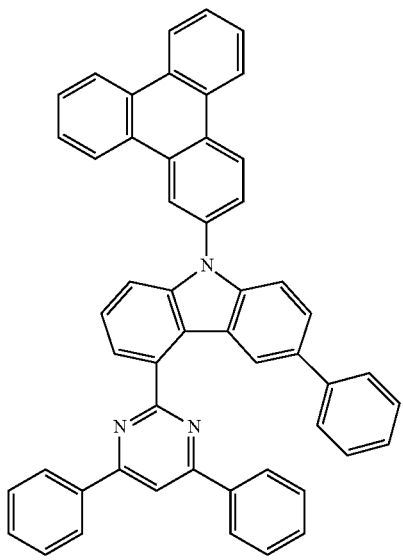
50
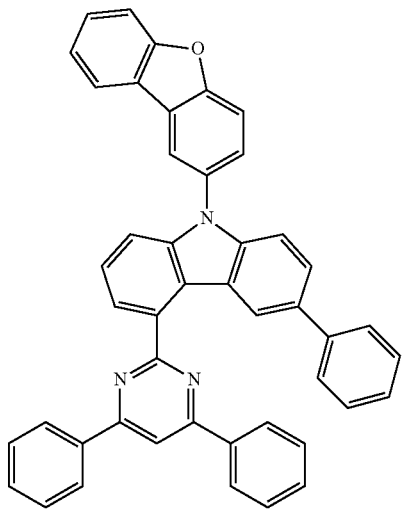
51
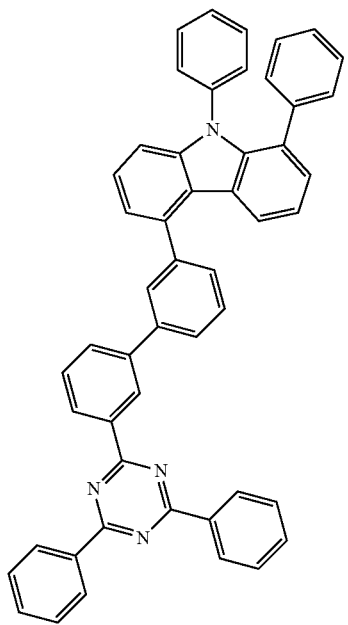
52
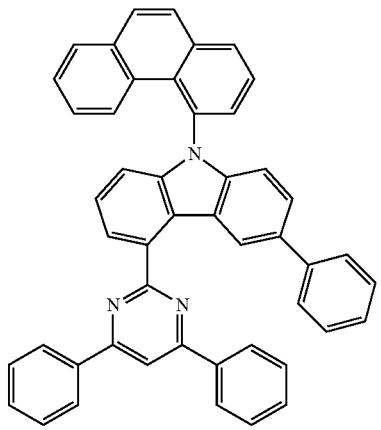

-continued
53
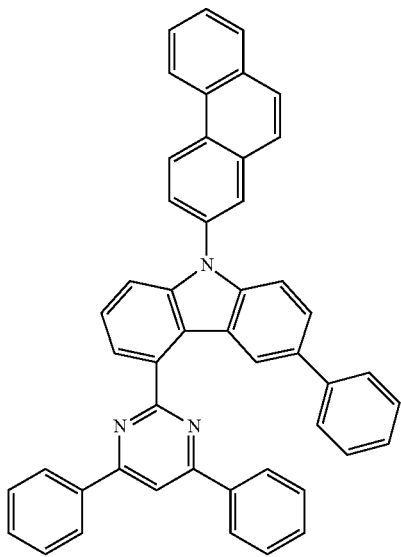
54
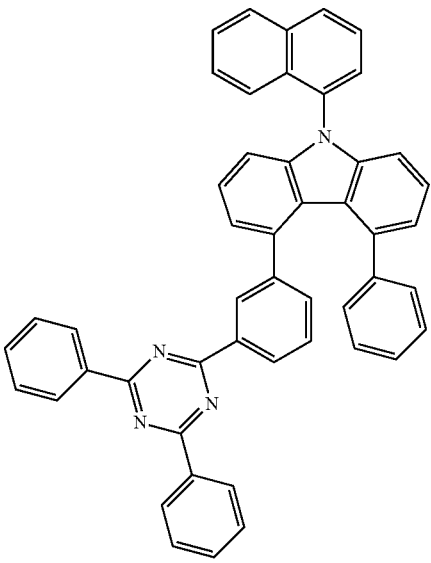
55
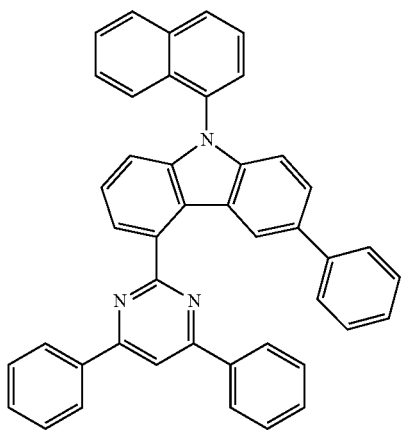
56
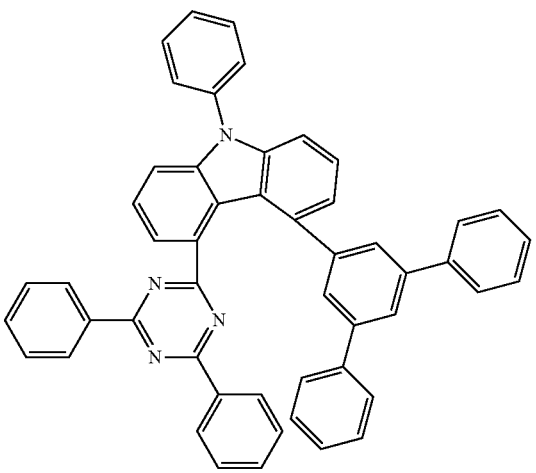
57
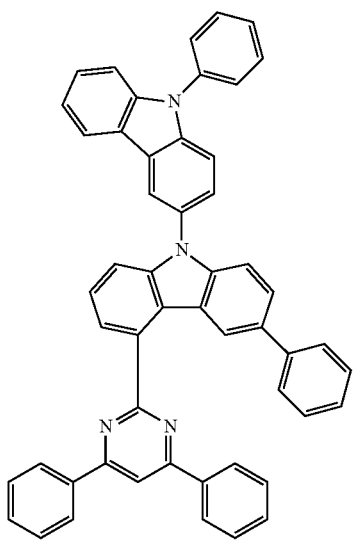
58
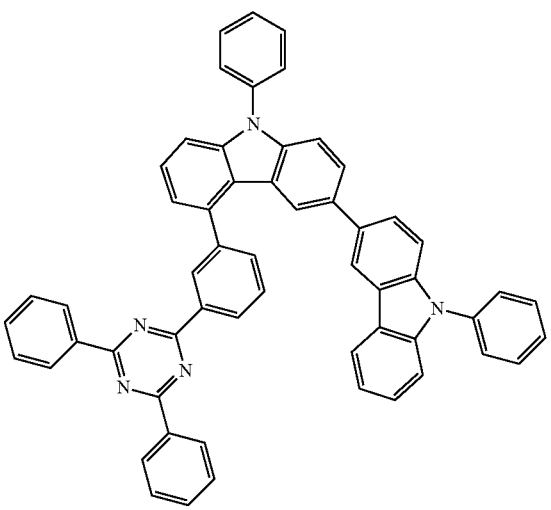

59
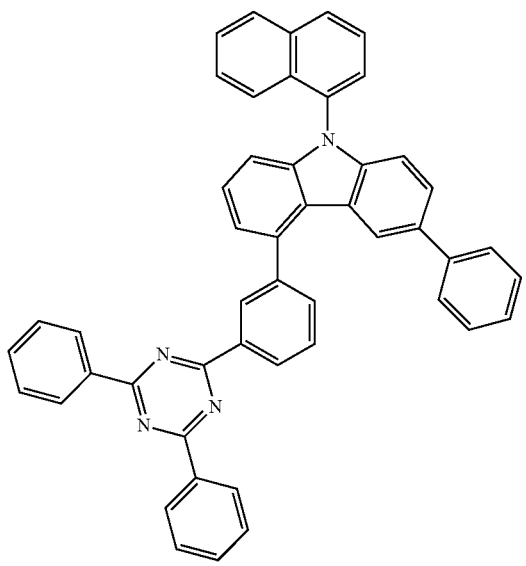
60
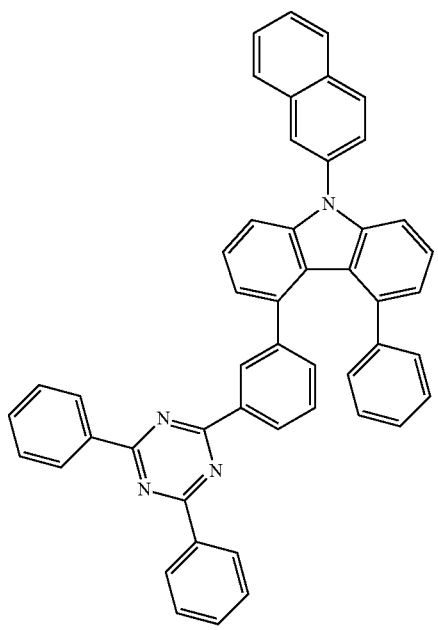
61
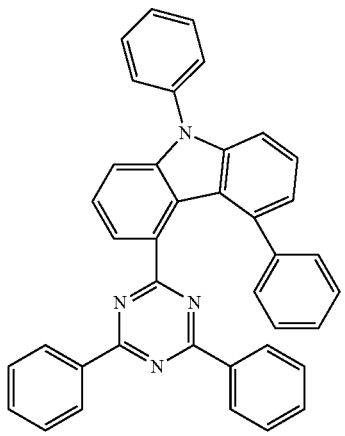
62
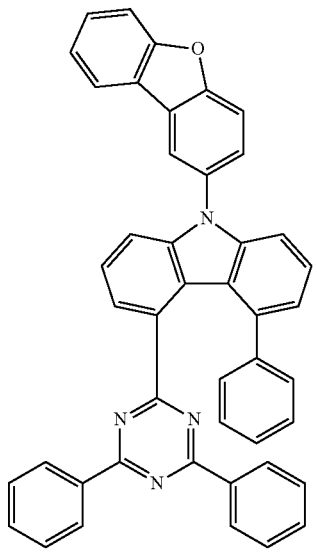

63
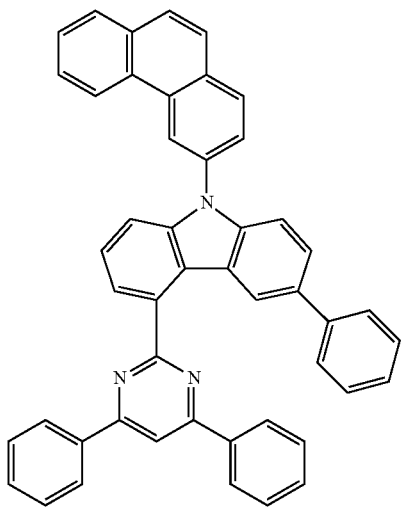
64
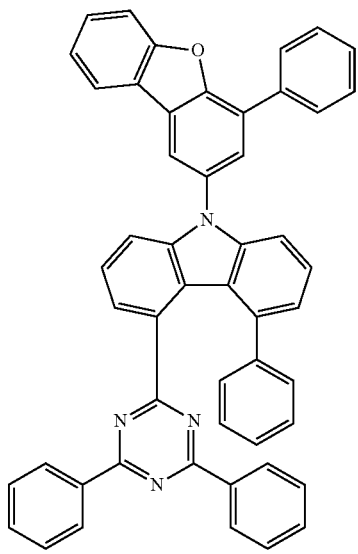
65
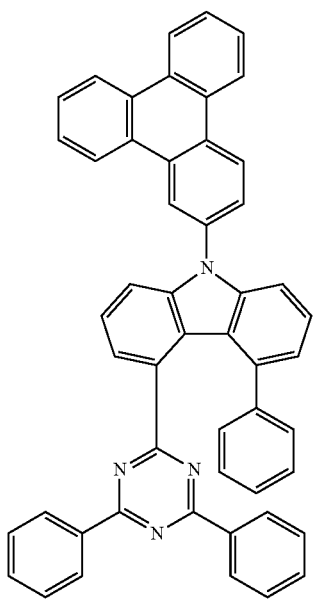
66
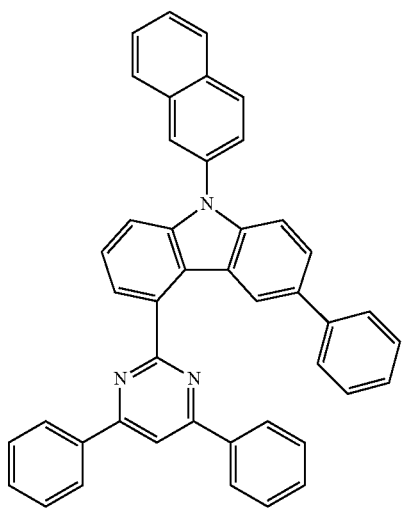

67
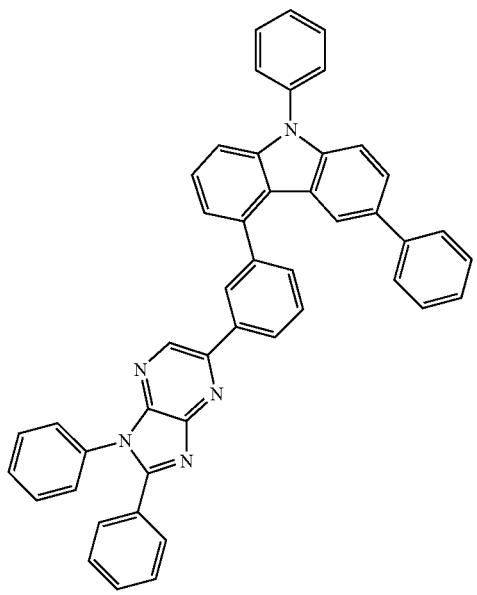
68
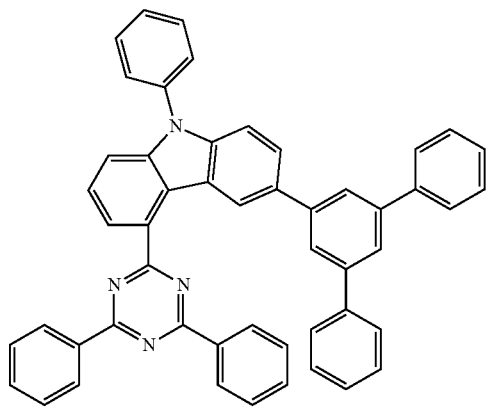
69
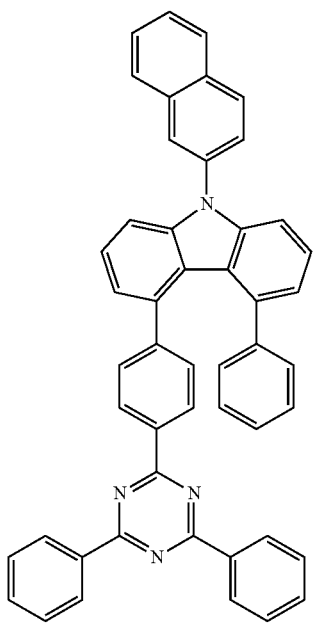
70
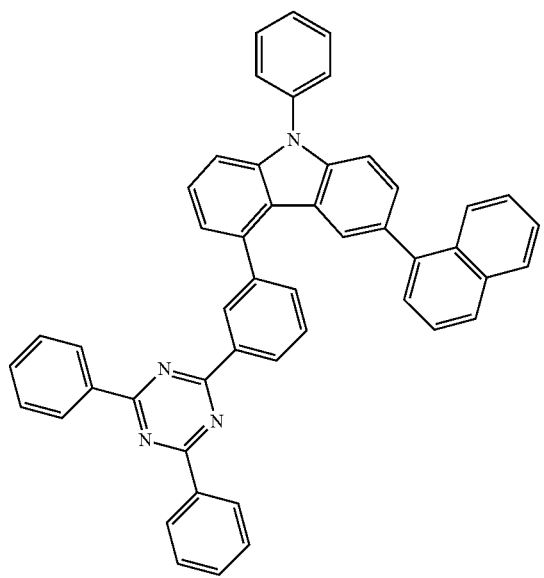

-continued
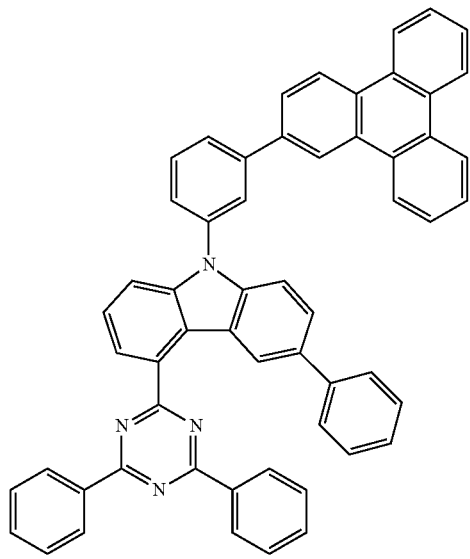
71
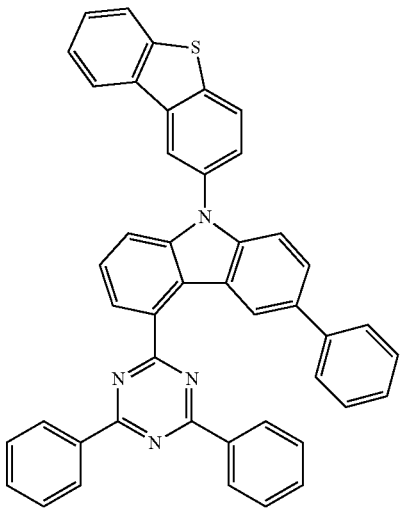
72
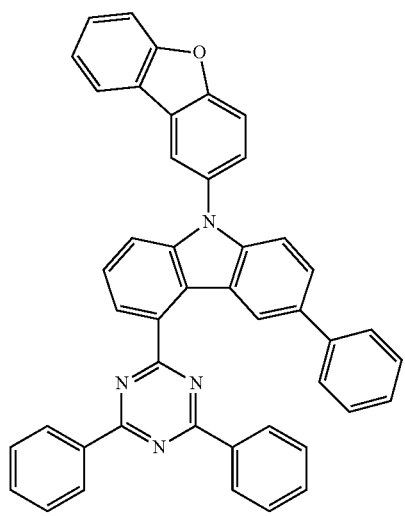
73
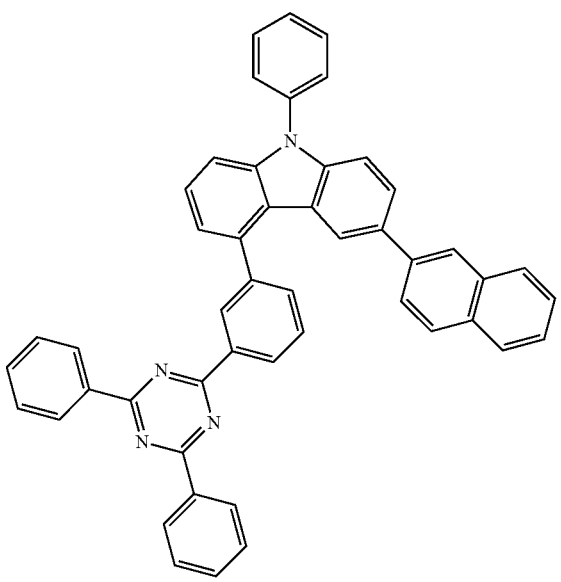
74
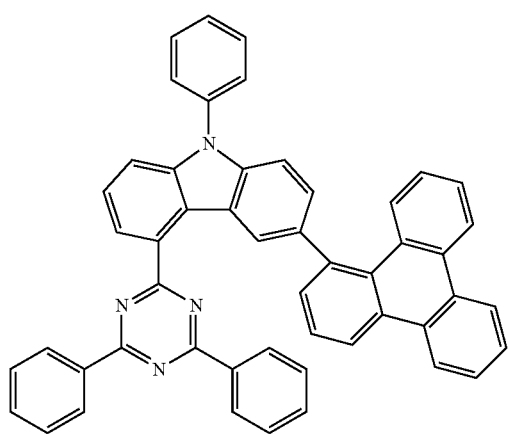
75
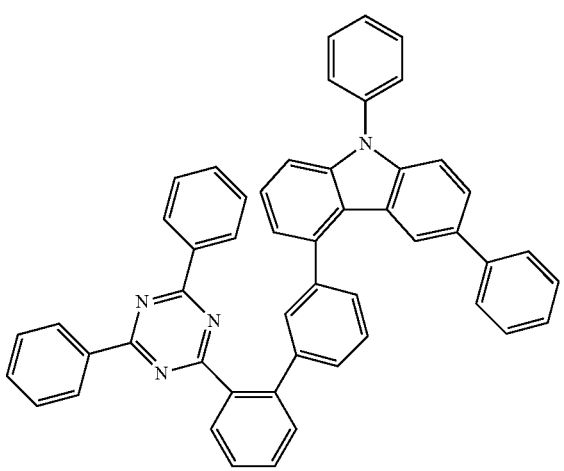
76

-continued
77
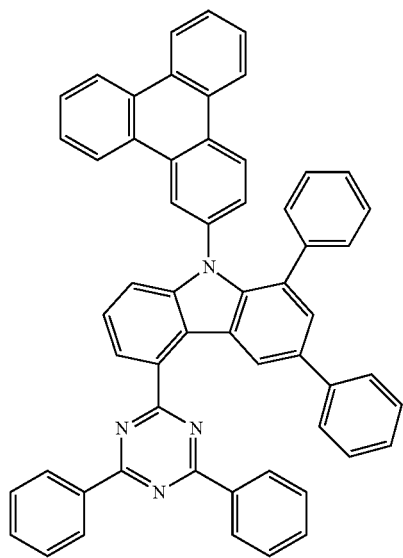
78
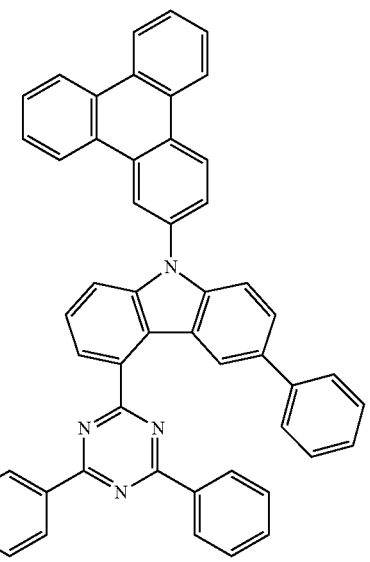
79
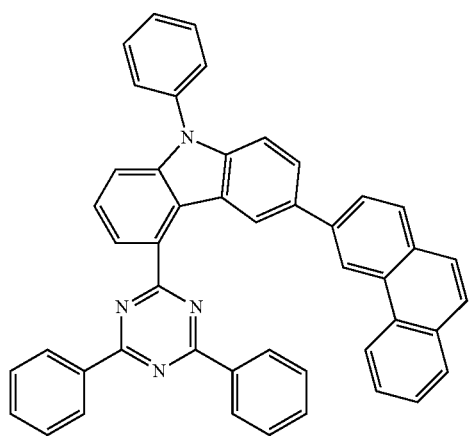
80
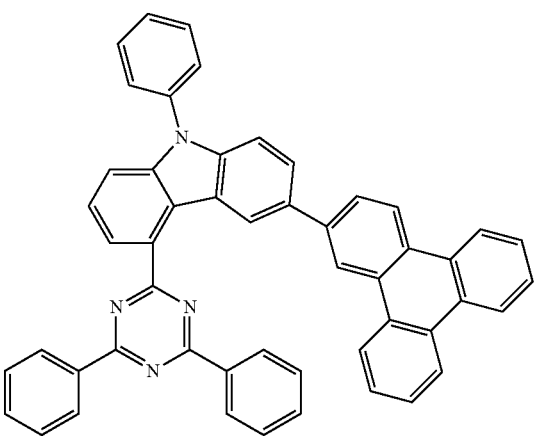
81
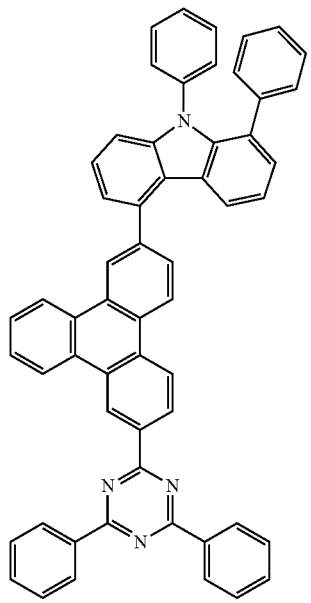
82
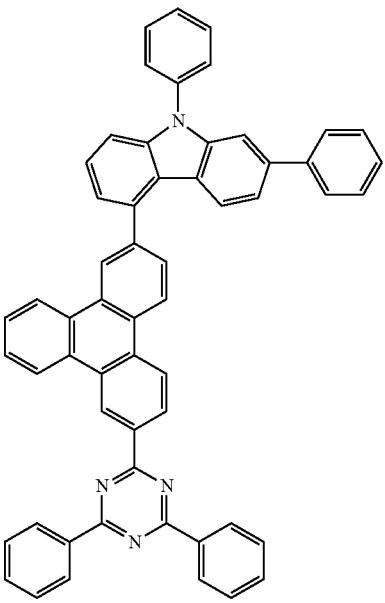

83
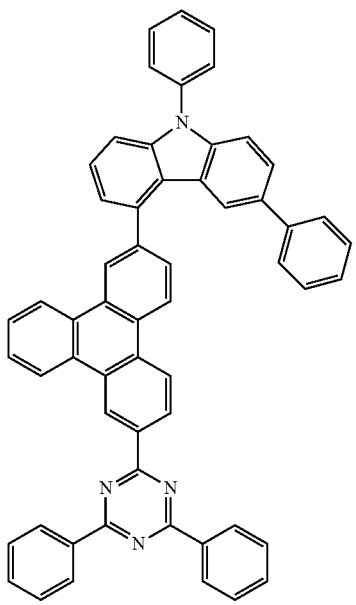
84
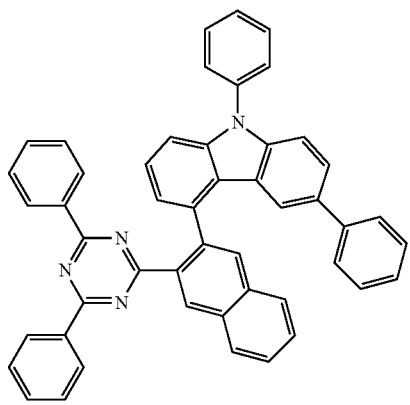
85
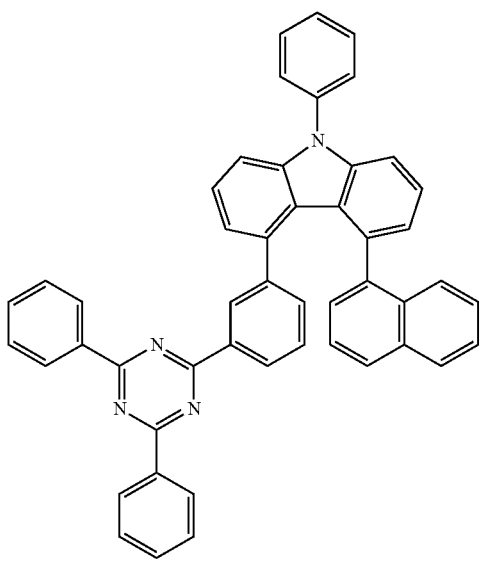
86
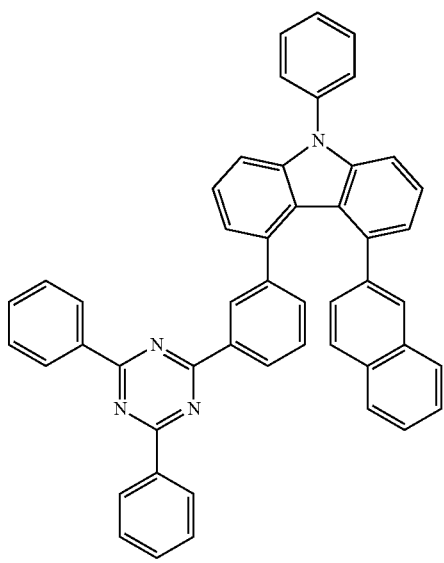
87
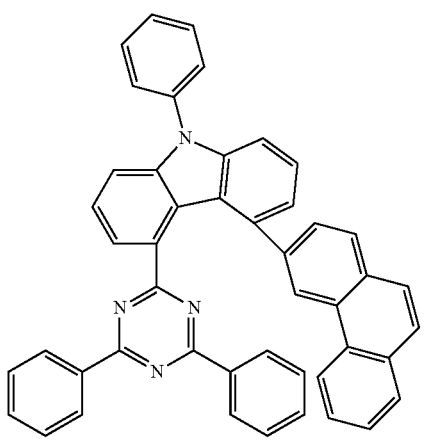
88
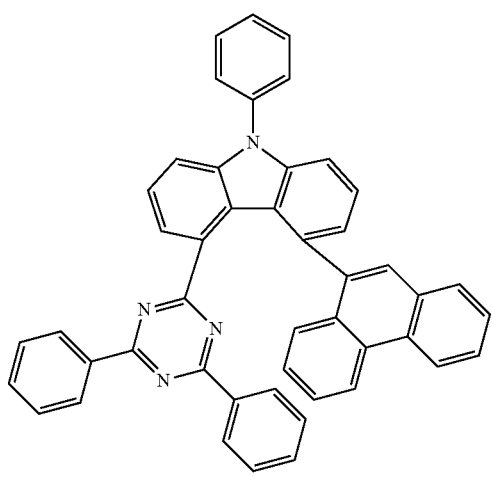

-continued
89
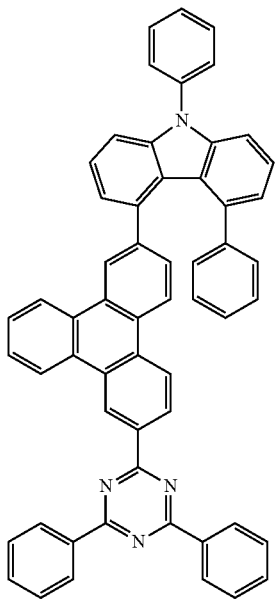
90
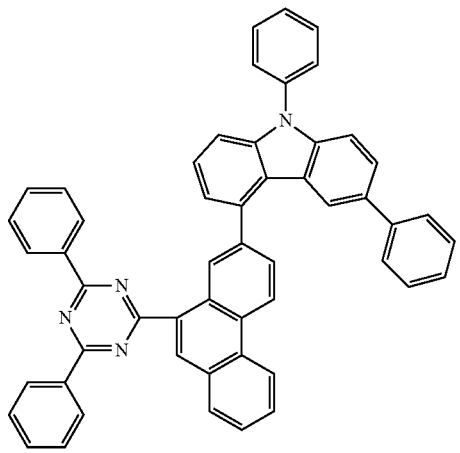
91
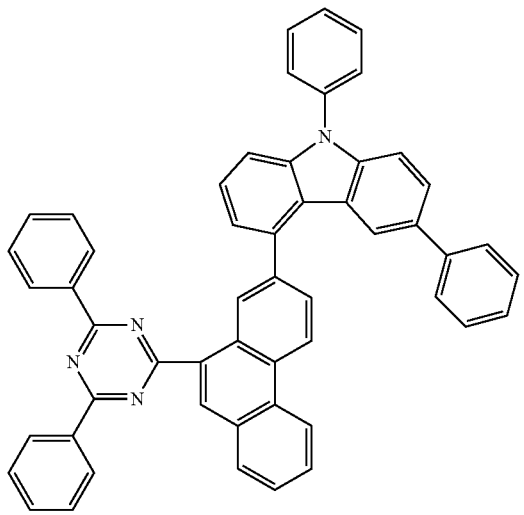
92
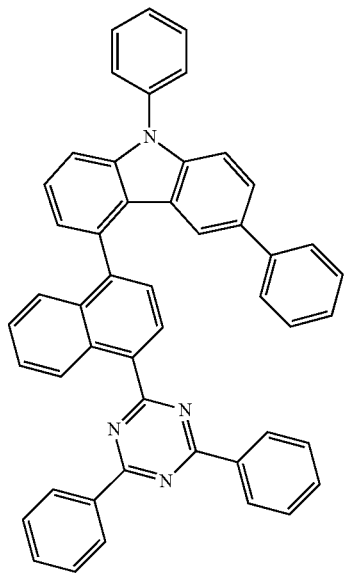

93
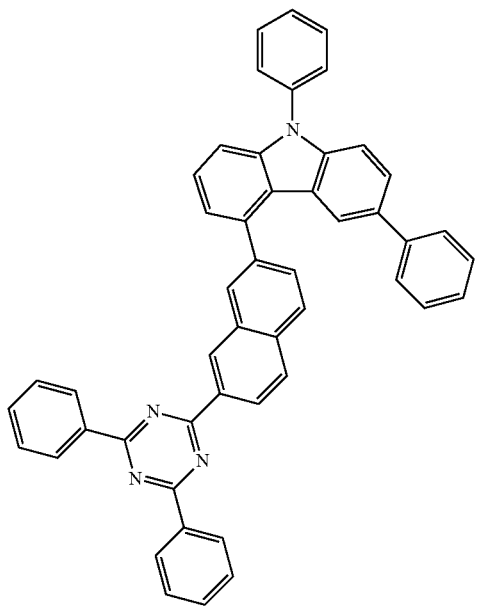
94
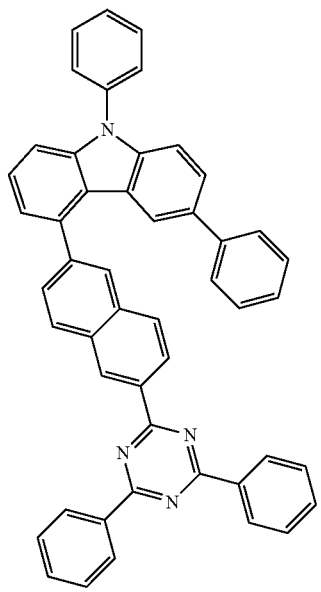
95
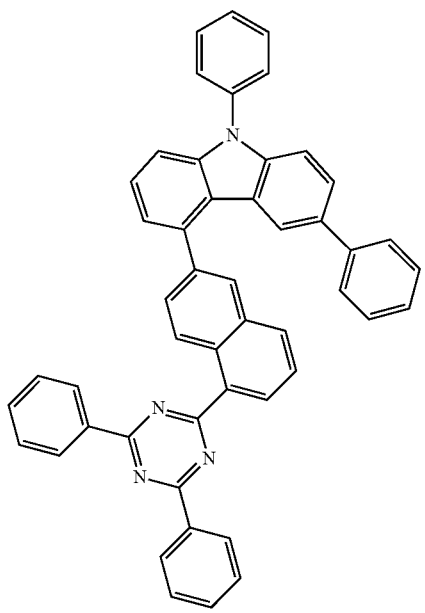
96
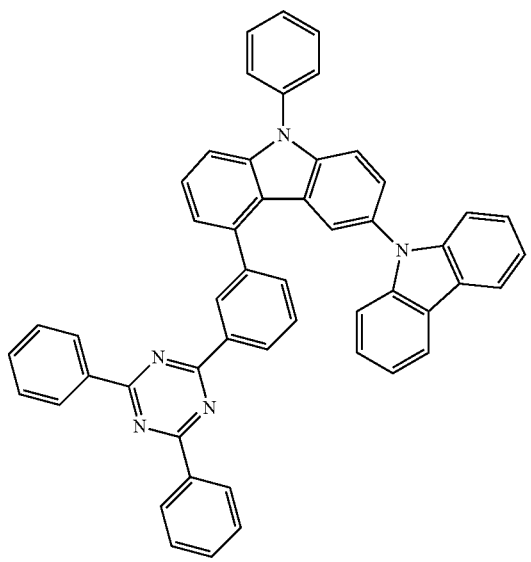

-continued
97
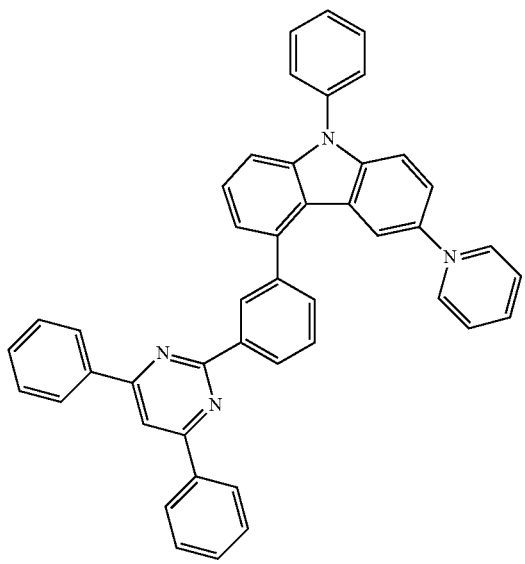
98
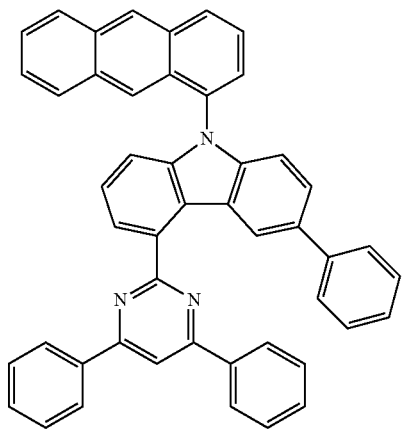
99
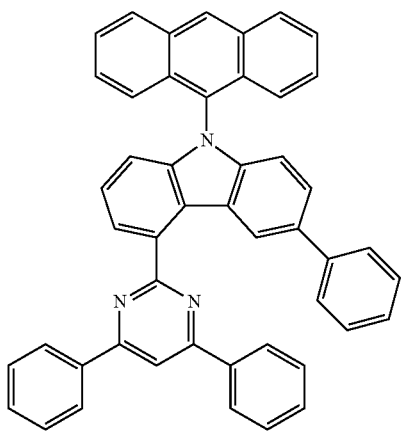
100
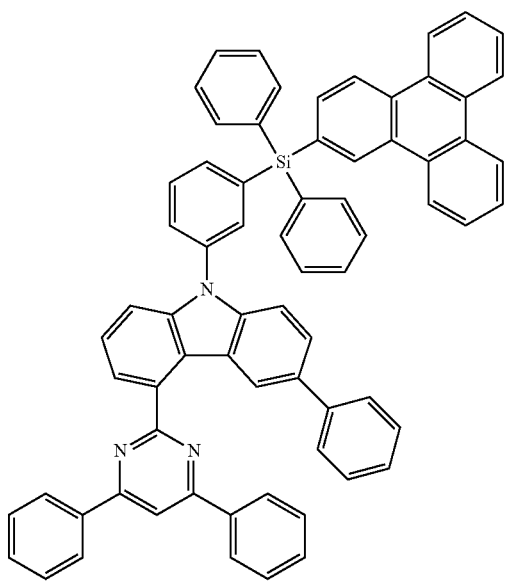

-continued
101 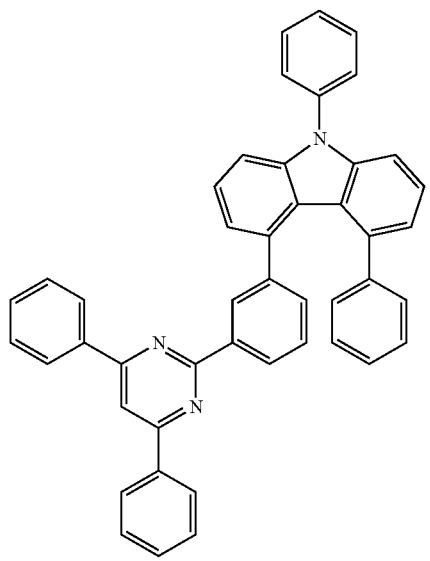
102 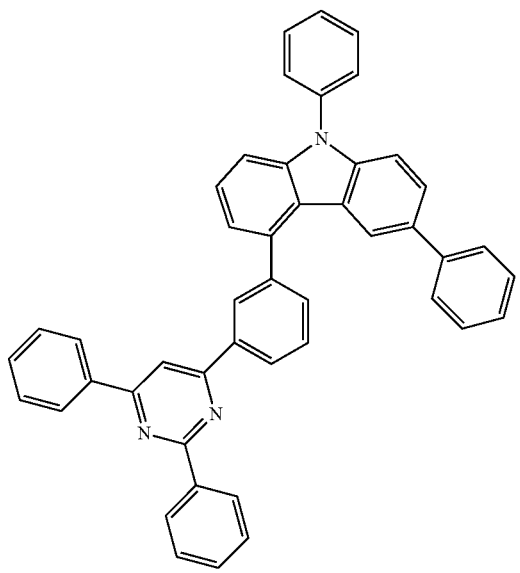
103 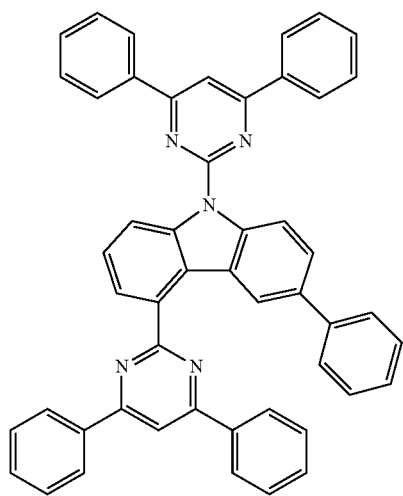
104 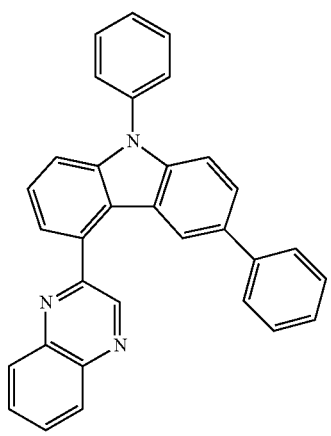
105 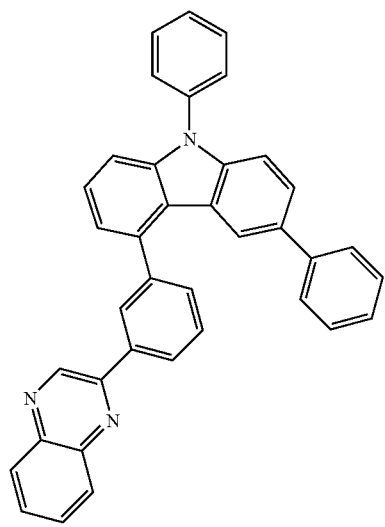
106 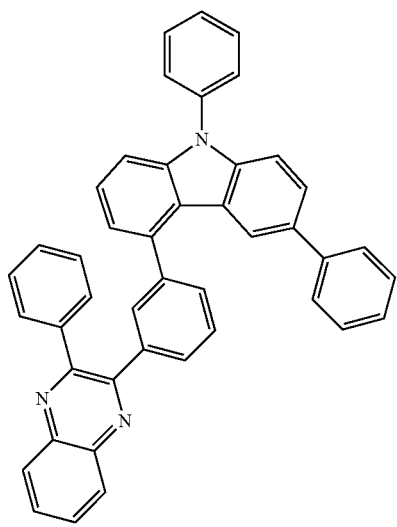

-continued
107 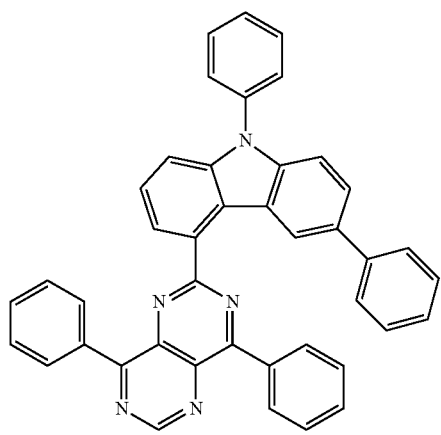
108 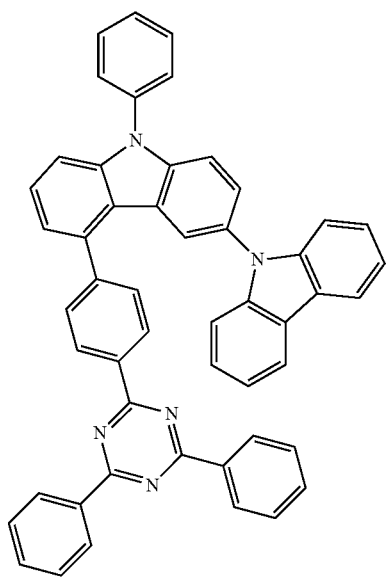
109 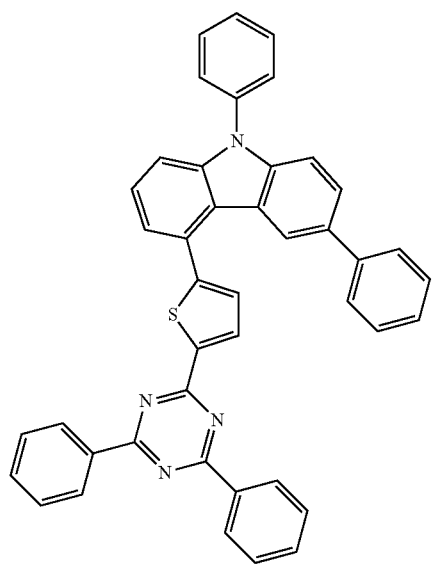
110 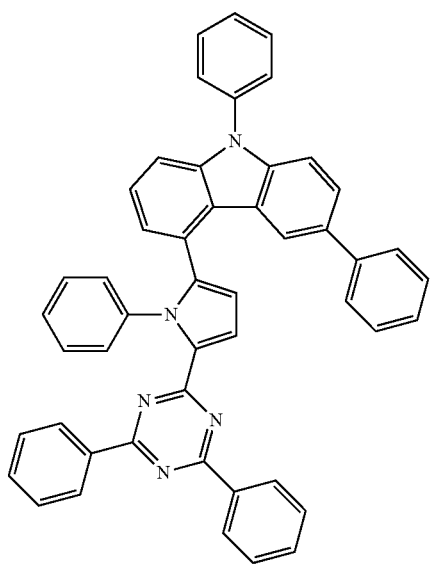

-continued
111
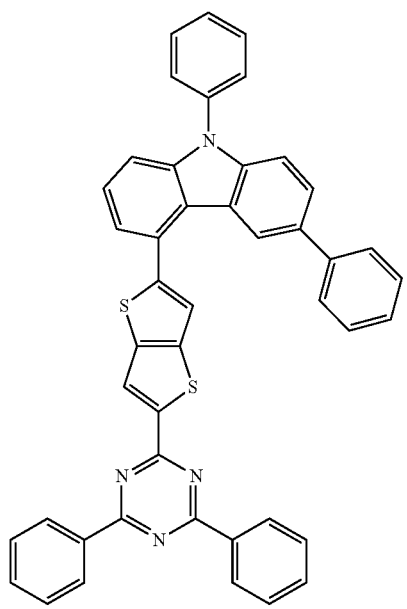
112
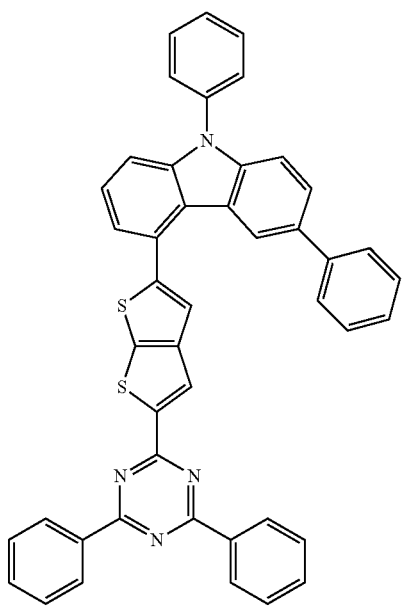
113
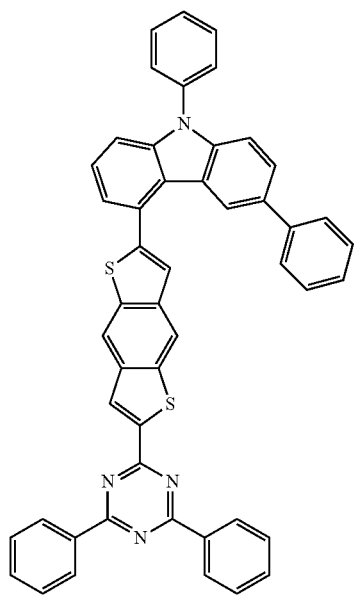
114
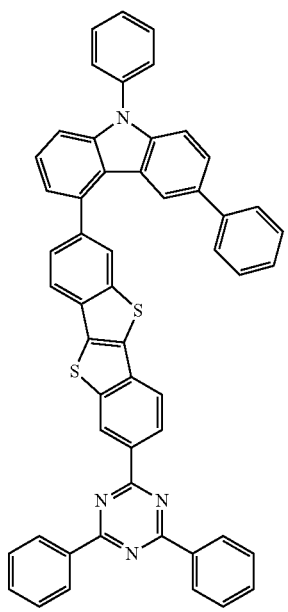

115
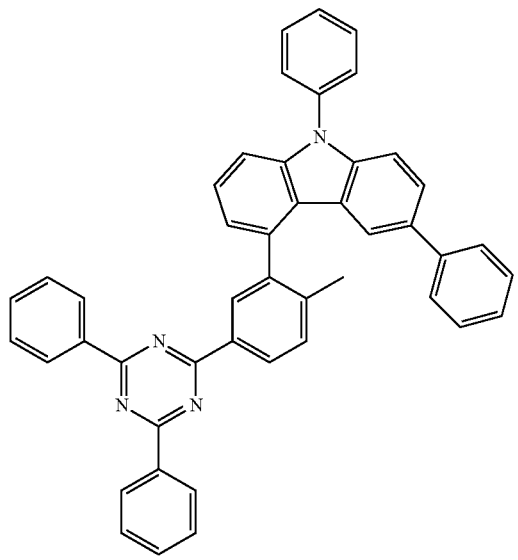
116
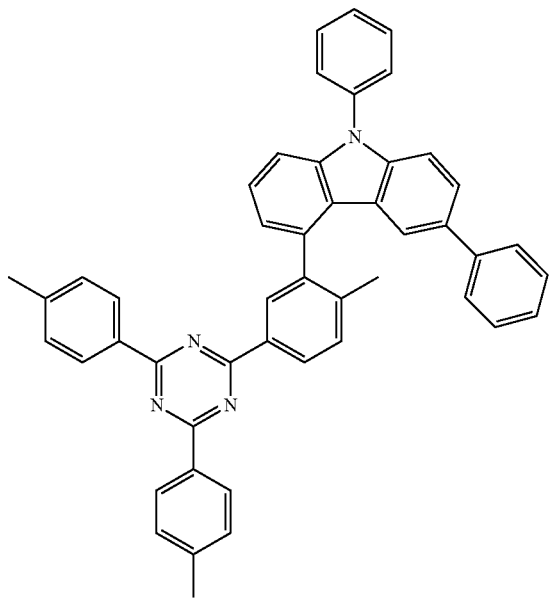
117
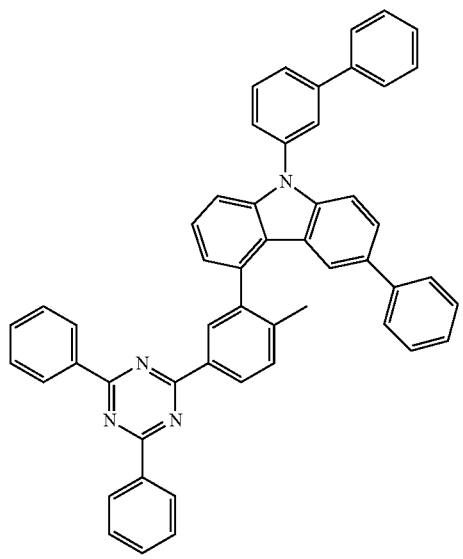
118
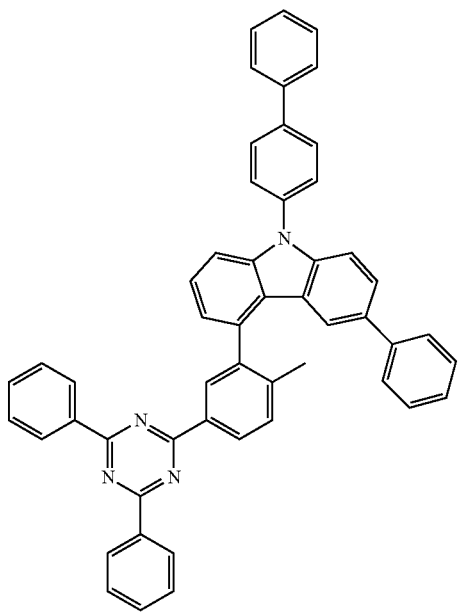

-continued
119
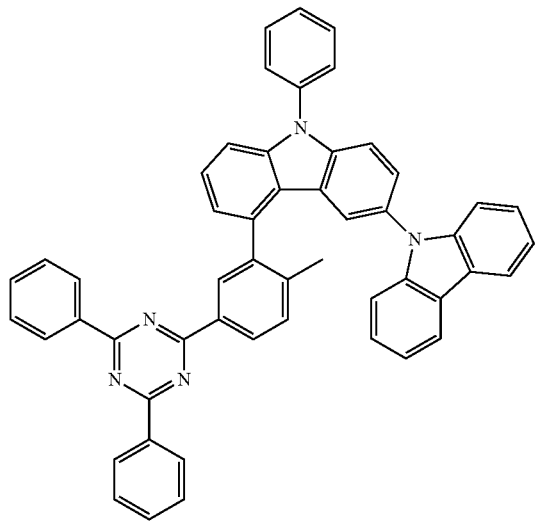
120
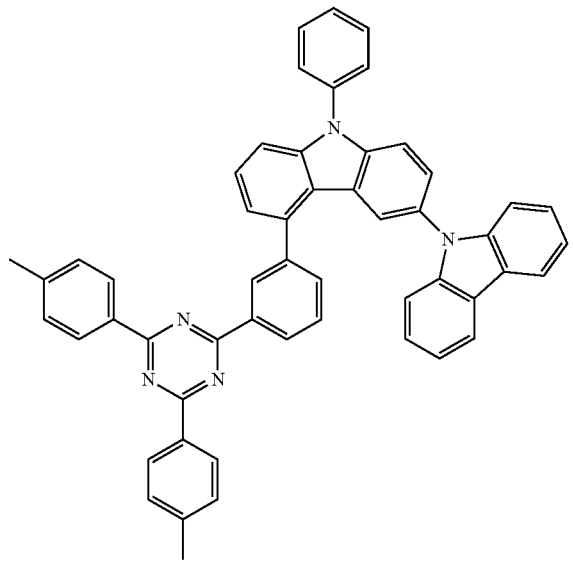
121
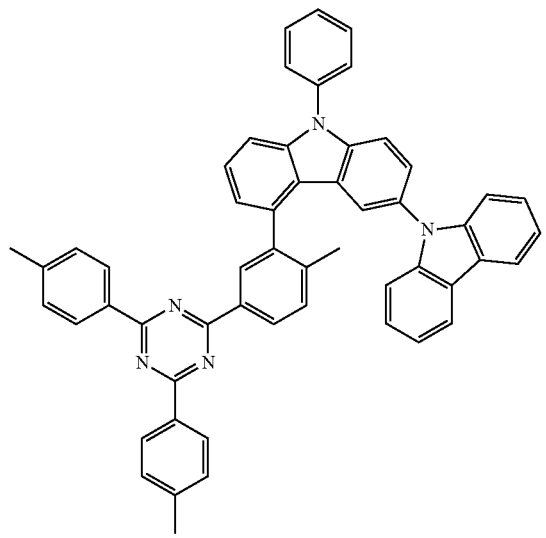
122
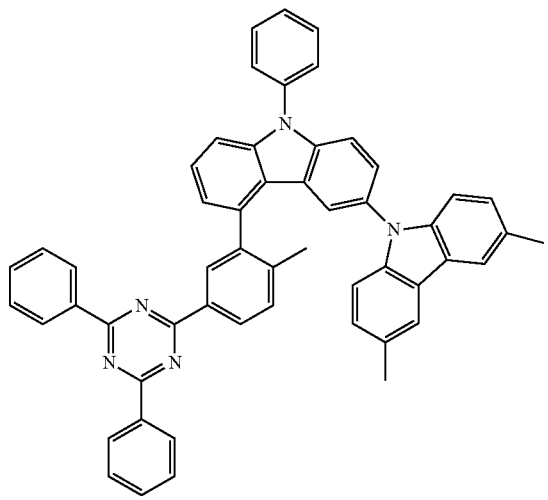
123
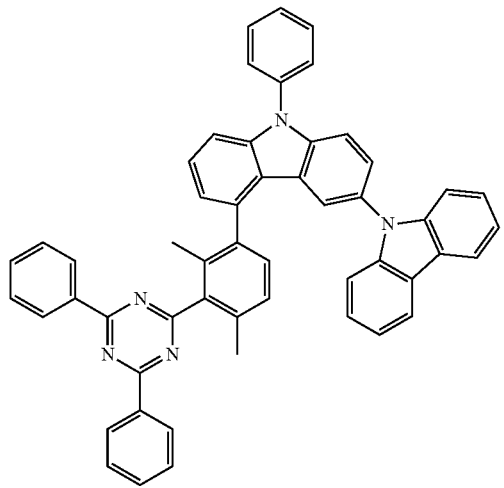
124
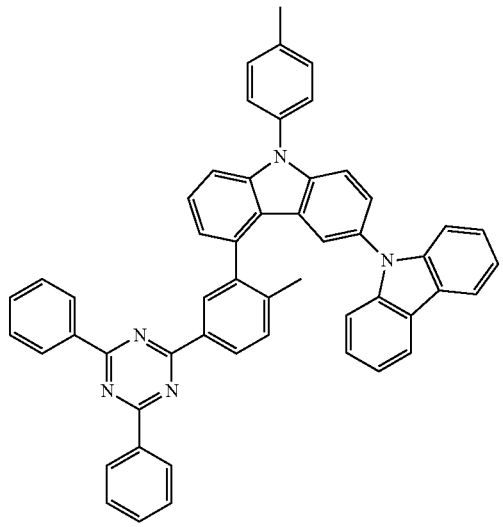

125
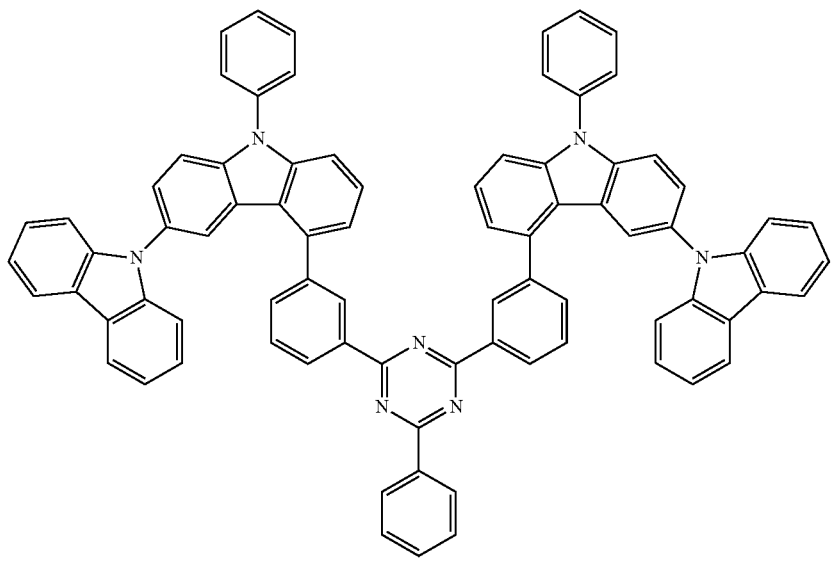
126
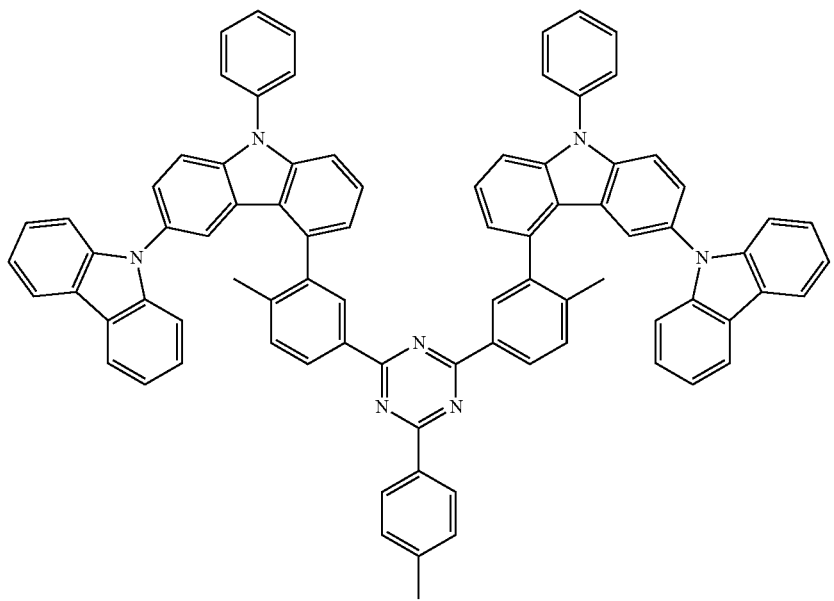

127
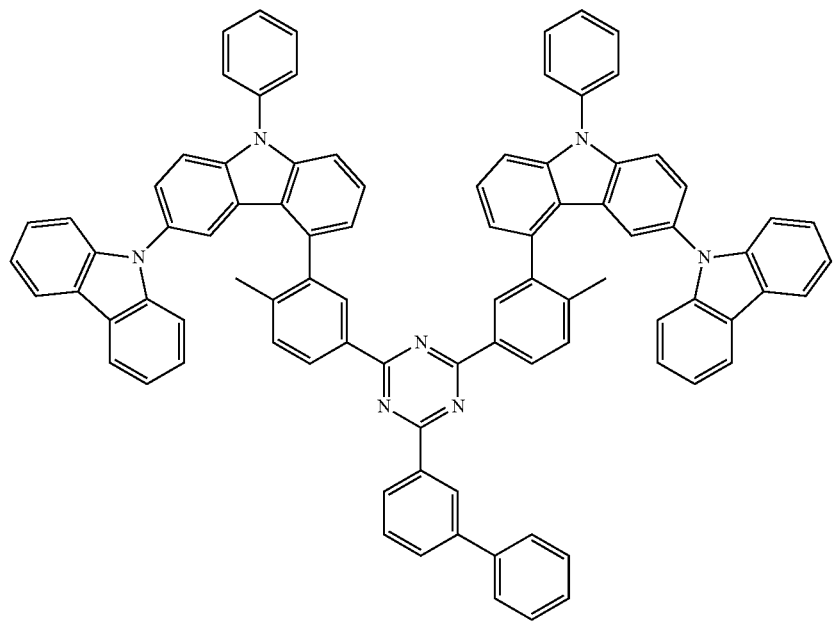
128
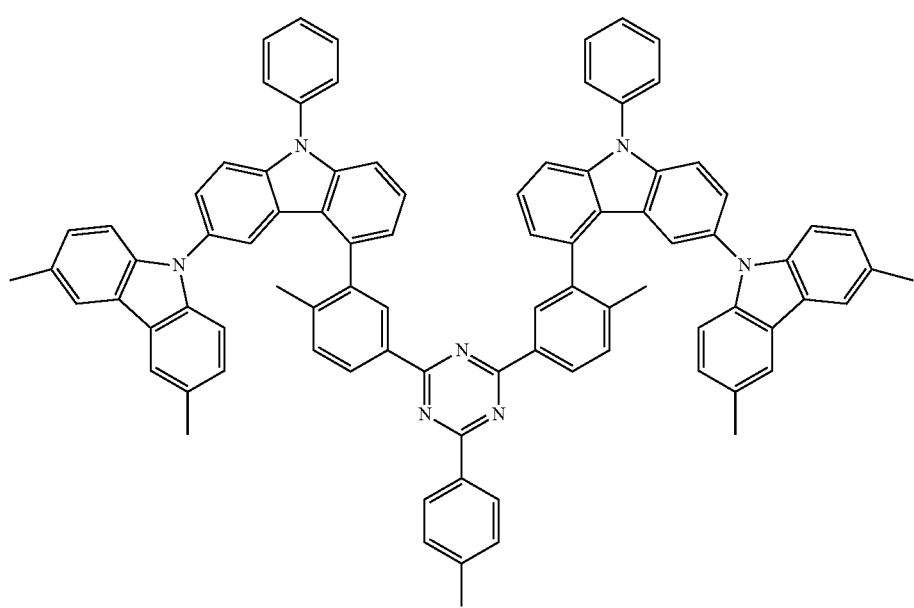

129

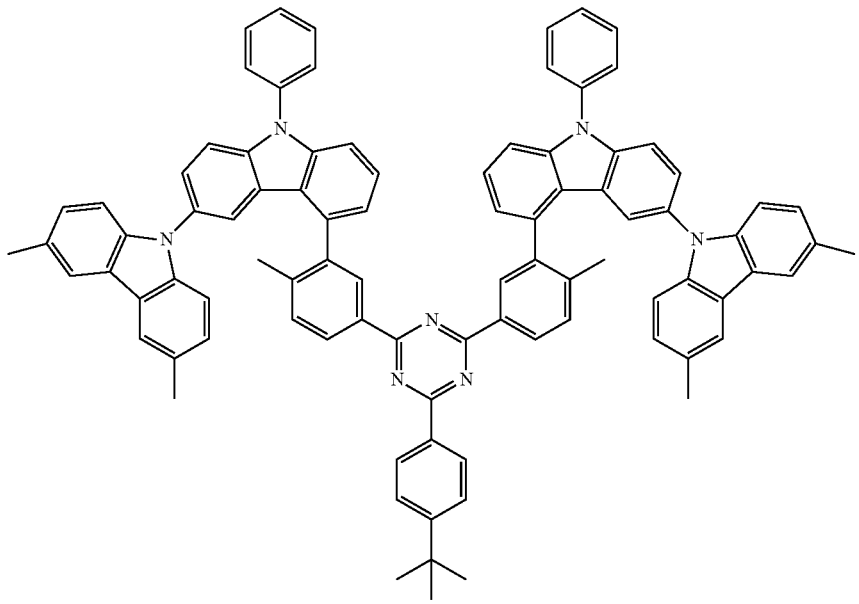

130

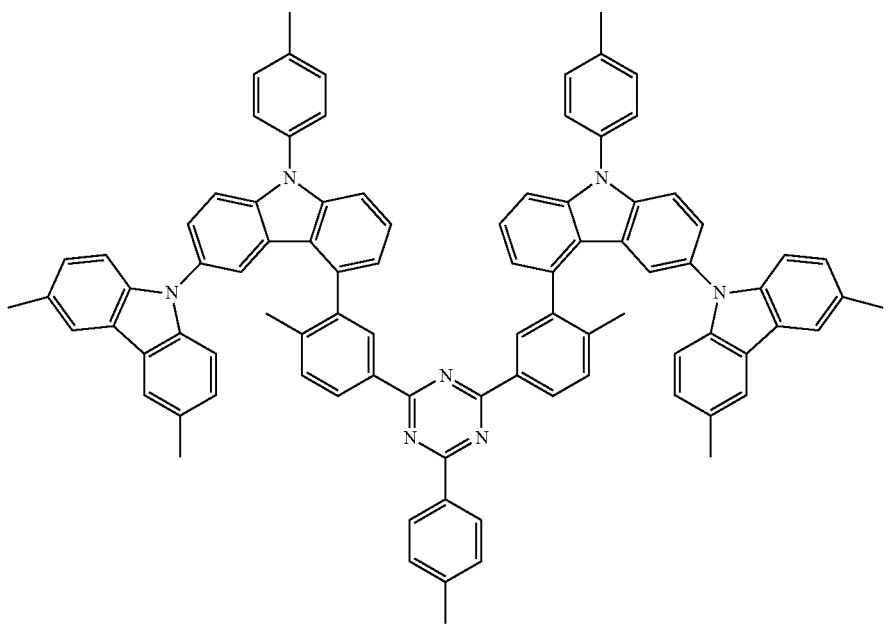

For example, in Formulae 1A and 1B, at least one of $R_5$ to $R_8$ may be selected from a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent nonaromatic condensed polycyclic group, and a substituted or unsubstituted monovalent nonaromatic condensed heteropolycyclic group. This may provide an enhanced steric hindrance effect to the carbazole-based compound of Formula 1A or 1B, and consequently suppress agglomeration of the carbazole-based compound. Thus, an organic light-emitting device including the carbazole-based compound of Formula 1A or 1B may have improved emission efficiency.

The carbazole-based compound of Formula 1A or 1B includes a "carbazole-based ring" (see Formula 1A'), and thus may have an energy band gap suitable for use as a material of an organic light-emitting device (for example, a host material of an emission layer).

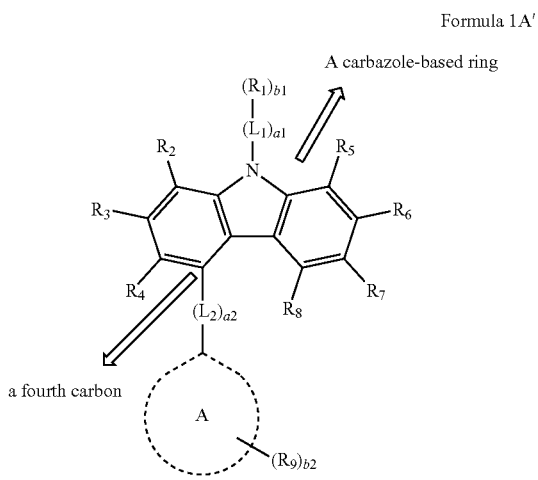

Formula 1A'

A carbazole-based ring a fourth carbon

The carbazole-based compound of Formula 1A or 1B does not include an amino group and a derivative thereof. An amino group and a derivative thereof may have poor thermal stability and poor electrical stability against migration of electrons, and may hinder controlling an energy level of the carbazole-based compound for use as a host material of an organic light-emitting device, and consequentially lower emission efficiency of the organic light-emitting device. However, the carbazole-based compound of Formula 1A or 1B is designed to exclude "an amino group and a derivative thereof" in molecules, and thus may have an energy band gap range appropriate for use as a material (for example, a host material of an emission layer) of an organic light-emitting device.

Furthermore, "the ring A" in the carbazole-based compound of Formula 1A or 1B is linked to a "fourth carbon" (refer to Formula 1A') of the carbazole-based ring in Formulae 1A and 1B, so that a highest occupied molecular orbital (HOMO) region and a lowest unoccupied molecular orbital (LUMO) region may be effectively separated from each other in the carbazole-based compound of Formula 1A or 1B. Thus, the carbazole-based compound of Formula 1A or 1b may have a high triplet (T1) energy level.

A synthesis method of the carbazole-based compound of Formula 1A or 1B may be understood by those of ordinary skill in the art based on synthesis examples to be described below.

The carbazole-based compound of Formula 1A or 1B is suitable for use in an organic layer, for example, as a host in an emission layer of an organic light-emitting device. According to another embodiment of the present disclosure, an organic light-emitting device includes a first electrode, a second electrode, and an organic layer disposed between the first electrode and the second electrode, wherein the organic layer includes an emission layer and at least one of the carbazole-based compounds of Formula 1A or 1B.

The organic light-emitting device, which includes the organic layer including the at least one of the carbazole-based compound of Formula 1A or 1B, may have a low driving voltage, a high efficiency, a high luminance, and a long lifetime.

The carbazole-based compound of Formula 1A or 1B may be used between a pair of electrodes of an organic light-emitting device, For example, the carbazole-based compound of Formula 1A or 1B may be included in at least one of the emission layer, a hole transport region between the first electrode and the emission layer (for example, including at least one of a hole injection layer, a hole transport layer, and an electron blocking layer), and an electron transport region between the emission layer and the second electrode (for example, including at least one of a hole blocking layer, an electron transport layer, and an electron injection layer). For example, the carbazole-based compound of Formula 1A or 1B may be included in the emission layer. In this regard, the emission layer may further include a dopant, and the carbazole-based compound of Formula 1A or 1B in the emission layer may serve as a host. The emission layer may be a blue emission layer emitting blue light, or a green emission layer emitting green light. The dopant may be a phosphorescent dopant.

As used herein, "(for example, the organic layer) including at least one of the carbazole-based compounds means that "(the organic layer) including one of the carbazole-based compounds of Formula 1A or 1B, or at least two different carbazole-based compounds of Formula 1A or 1B".

In some embodiments, the organic layer may include only Compound 1 above as the carbazole-based compound of Formula 1A or 1B. Compound 1 may be situated in the emission layer of the organic light-emitting device. In some embodiments, the organic layer may include Compounds 1 and 2 as the carbazole-based compound of Formula 1A or 1B. In this regard, Compounds 1 and 2 may be present in the same layer (for example, in the emission layer) or may be present in different layers.

For example, the first electrode may be an anode as a hole injection electrode, and the second electrode may be a cathode as an electron injection electrode, or vice versa. That is, the first electrode may be a cathode as an electron injection electrode, and the second electrode may be an anode as a hole injection electrode.

For example, the first electrode may be an anode, the second electrode may be a cathode, and the organic layer may include i) a hole transport region disposed between the first electrode and the emission layer and including at least one of a hole injection layer, a hole transport layer, and an electron blocking layer; and ii) an electron transport region disposed between the emission layer and the second electrode and including at least one of a hole blocking layer, an electron transport layer, and an electron injection layer.

The term "organic layer" as used herein refers to a single layer and/or a plurality of layers disposed between the first and second electrodes of the organic light-emitting device. The "organic layer" may include an organic compound, and/or an organometallic complex including a metal.

FIG. 1 is a schematic view of an organic light-emitting device 10 according to an embodiment of the present disclosure. Hereinafter, a structure of an organic light-emitting device according to an embodiment of the present disclosure and a method of manufacturing the same will now be described with reference to FIG. 1. Referring to FIG. 1, the organic light-emitting device 10 has a structure in which a substrate 11, a first electrode 11, an organic layer 15, and a second electrode 19 are sequentially stacked in this order.

A substrate (not shown) may be disposed under the first electrode 11 or on the second electrode 190 in FIG. 1. The substrate may be any substrate that is used in conventional organic light emitting devices. In some embodiments the substrate may be a glass substrate or a transparent plastic substrate with strong mechanical strength, thermal stability, transparency, surface smoothness, ease of handling, and water resistance.

The first electrode 11 may be formed by depositing or sputtering a first electrode-forming material on the substrate 11. The first electrode 11 may be an anode. A material having a high work function may be selected as a material for the first electrode to facilitate hole injection. The first electrode 11 may be a reflective electrode, a semi-transmissive electrode, or a transmissive electrode. For example, the material for the first electrode 13 may be indium tin oxide (ITO), indium zinc oxide (IZO), tin oxide ($SnO_2$), or zinc oxide (ZnO). In some embodiments, the material for the first electrode 13 may be metals, for example, magnesium (Mg), aluminum (Al), aluminum-lithium (Al—Li), calcium (Ca), magnesium-indium (Mg—In), magnesium-silver (Mg—Ag), or the like.

The first electrode 11 may have a single-layer structure or a multi-layer structure including at least two layers.

The organic layer 15 may be disposed on the first electrode 11.

The organic layer 15 may include a hole transport region; an EMI, and an electron transport region.

The hole transport region may be disposed between the first electrode 11 and the EML.

The hole transport region may include at least one of a hole injection layer (HIL), a hole transport layer (HTL), an electron blocking layer (EBL), and a buffer layer.

The hole transport region may include exclusively the HIL or the HTL. In some embodiments, the electron transport region may have a structure including a HIL/HTL or a HIL/HTL/EBL, wherein the layers forming the structure of the electron transport region may be sequentially stacked on the first electrode 10 in the stated order.

When the hole transport region includes the HIL, the HIL may be formed on the first electrode 11 by any of a variety of methods, for example, vacuum deposition, spin coating, casting, Langmuir-Blodgett (LB) deposition, or the like.

When the HIL is formed using vacuum deposition, vacuum deposition conditions may vary depending on the material that is used to form the HIL, and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 to about 100 Å/sec. However, the deposition conditions are not limited thereto.

When the HIL is formed using spin coating, the coating conditions may vary depending on the material that is used to form the HIL, and the desired structure and thermal properties of the HIL to be formed. For example, the coating rate may be in the range of about 2,000 revolutions per minute (rpm) to about 5,000 rpm, and a temperature at which heat treatment is performed to remove a solvent after coating may be in a range of about 80° C. to about 200° C. However, the coating conditions are not limited thereto.

Conditions for forming the HTL and the EBL may be the same as those for the HIL described above.

In some embodiments, the hole transport region may include at least one of m-MTDATA, TDATA, 2-TNATA, NPB, β-NPB, TPD, Spiro-TPD, Spiro-NPB, α-NPB, TAPC, HMTPD, 4,4',4"-tris(N-carbazolyl)triphenylamine (TCTA), polyaniline/dodecylbenzene sulfonic acid (Pani/DBSA), poly(3,4-ethylenedioxythiophene)/poly(4-styrenesulfonate) (PEDOT/PSS), polyaniline/camphor sulfonic acid (Pani/CSA), polyaniline/poly(4-styrenesulfonate) (PANI/PSS), a compound represented by Formula 201 below, and a compound represented by Formula 202 below.

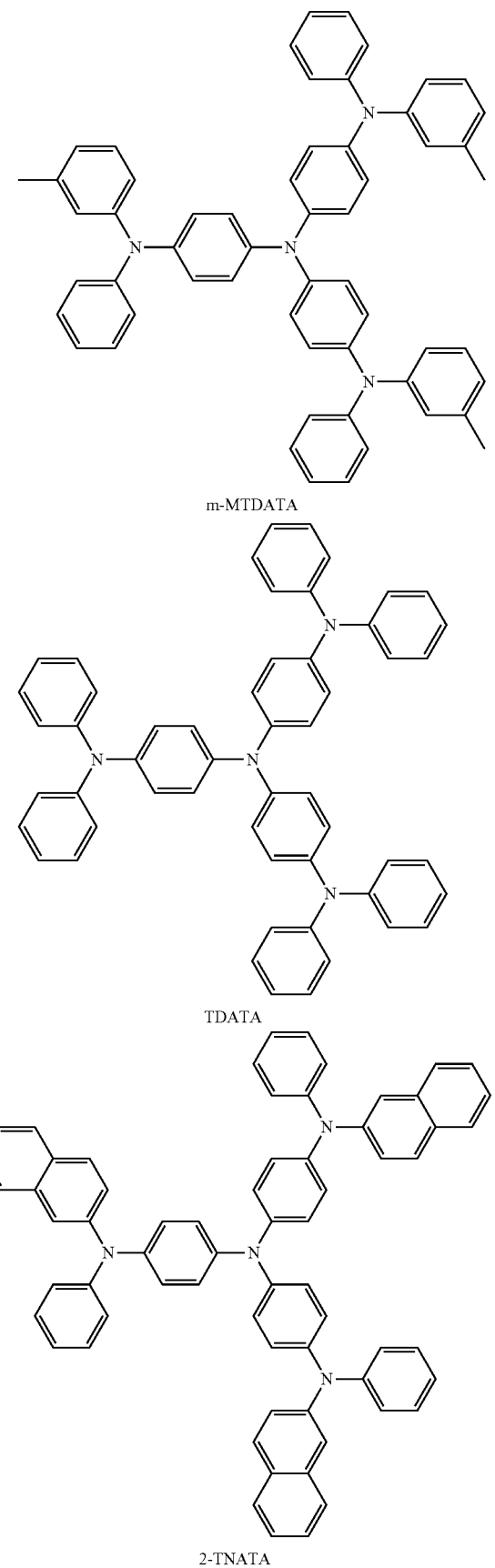

m-MTDATA

TDATA

2-TNATA

-continued

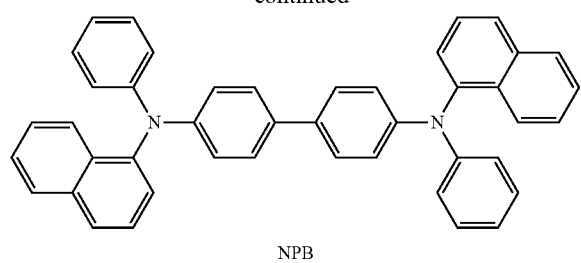

NPB

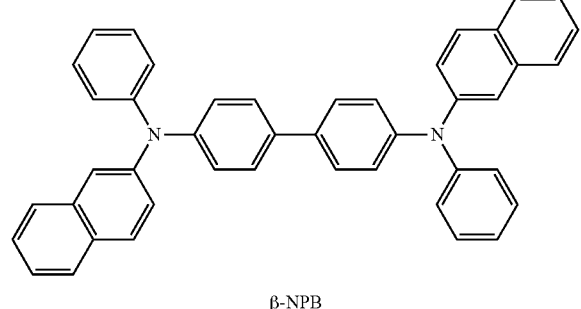

β-NPB

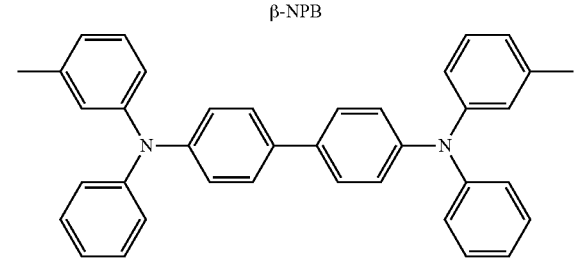

TPD

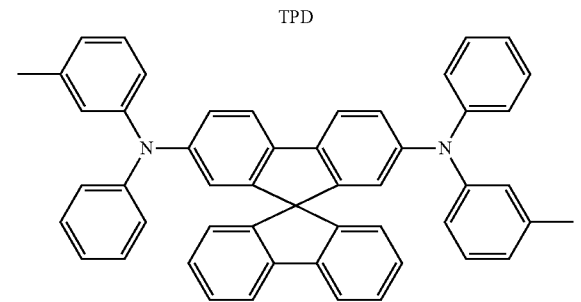

Spiro-TPD

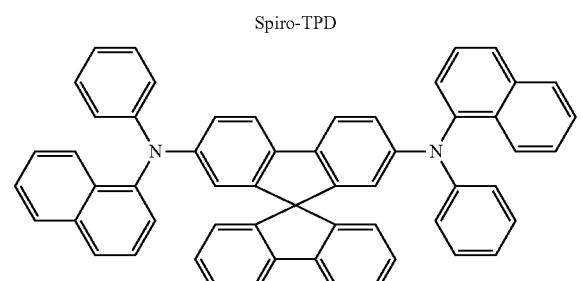

Spiro-NPB

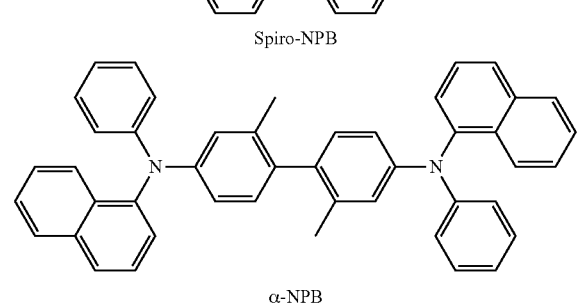

α-NPB

-continued

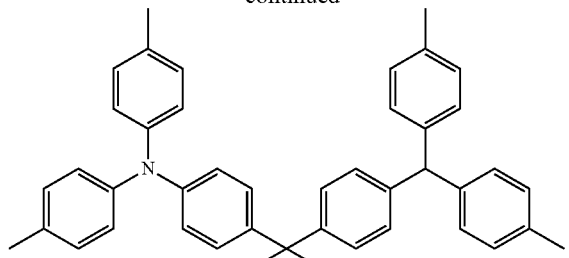

TAPC

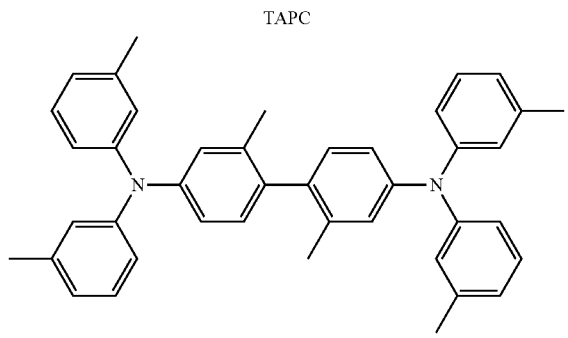

HMTPD

Formula 201

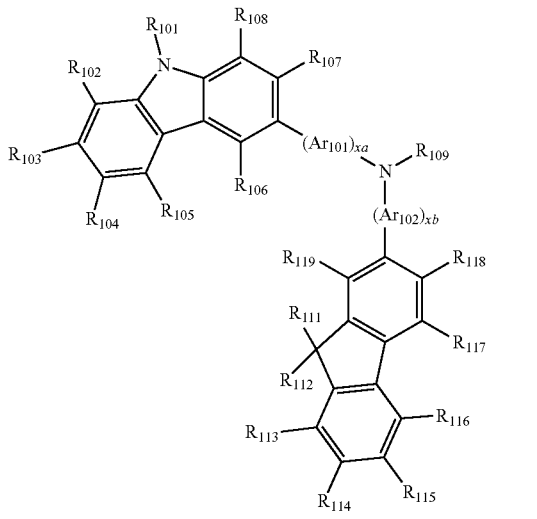

Formula 202

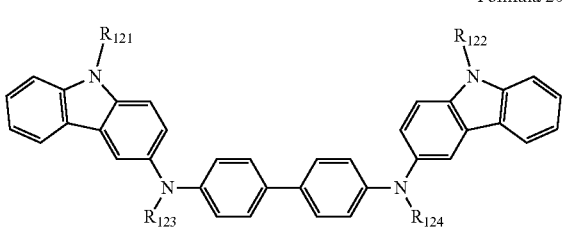

In Formula 201 above, $Ar_{101}$ and $Ar_{102}$ may be each independently selected from:

a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, and a pentacenylene group, and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, and a pentacenylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_2$-$C_{10}$ heterocycloalkyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group.

In Formula 201, xa and xb may be each independently an integer from 0 to 5, for example, may be 0, 1, or 2. For example, xa may be 1, and xb may be 0, but are not limited thereto.

In Formulae 201 and 202, $R_{101}$ to $R_{108}$, $R_{111}$ to $R_{119}$, and $R_{121}$ to $R_{124}$ may be each independently one of:

a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, a hexyl group, or the like), and a $C_1$-$C_{10}$ alkoxy group (for example, a methoxy group, an ethoxy group, a propoxy group, a butoxy group, a pentoxy group, or the like), a $C_1$-$C_{10}$ alkyl group and a $C_1$-$C_{10}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof, a phenyl group, a naphthyl group, an anthracenyl group, a fluorenyl group, and a pyrenyl group, and a phenyl group, a naphthyl group, an anthracenyl group, a fluorenyl group, and a pyrenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group. However, embodiments of the present disclosure are not limited thereto.

In Formula 201 above, $R_{109}$ may be one of:

a phenyl group, a naphthyl group, an anthracenyl group, and a pyridinyl group, and a phenyl group, a naphthyl group, an anthracenyl group, and a pyridinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group.

In some embodiments, the compound of Formula 201 may be represented by Formula 201A, but is not limited thereto:

Formula 201A

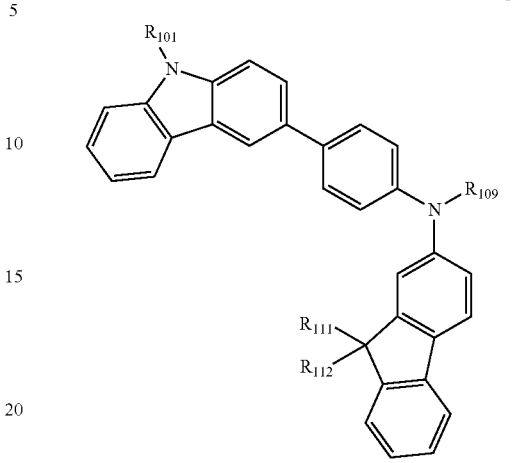

In Formula 201A, $R_{101}$, $R_{111}$, $R_{112}$, and $R_{109}$ may be the same as those defined above.

For example, the compound of Formula 201 and the compound of Formula 202 may include Compounds HT1 to HT20 below, but are not limited thereto:

HT1

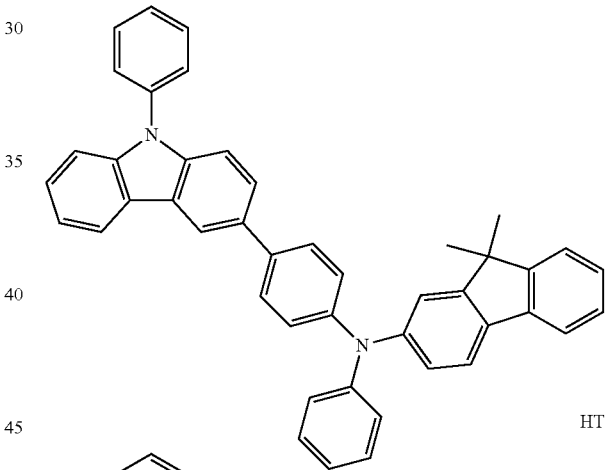

HT2

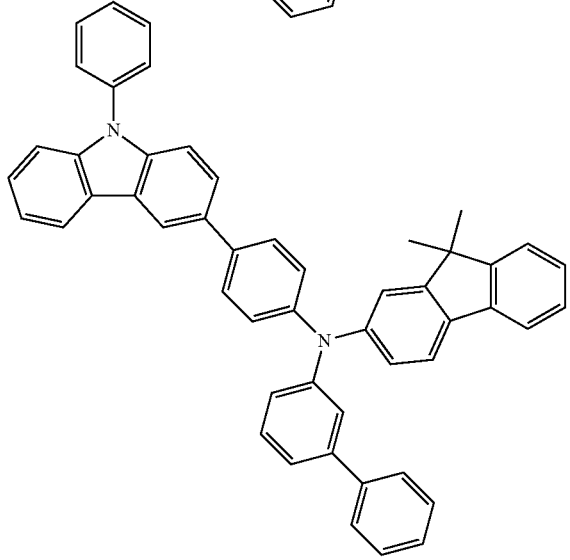

HT3
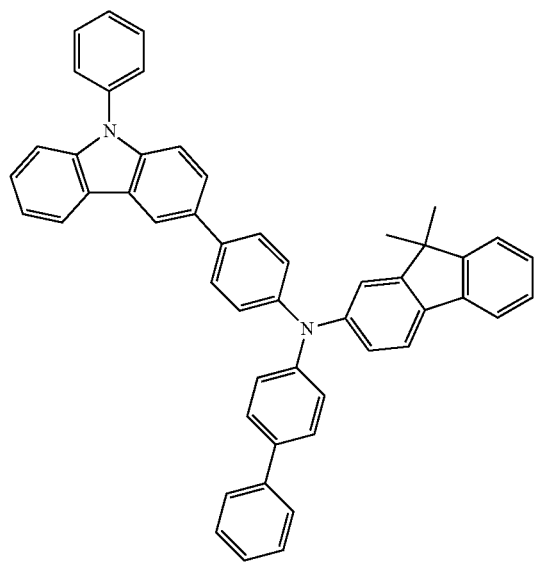
HT4
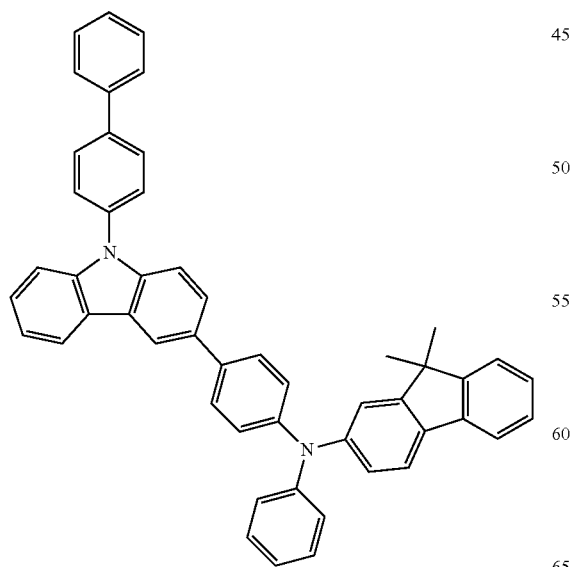
HT5
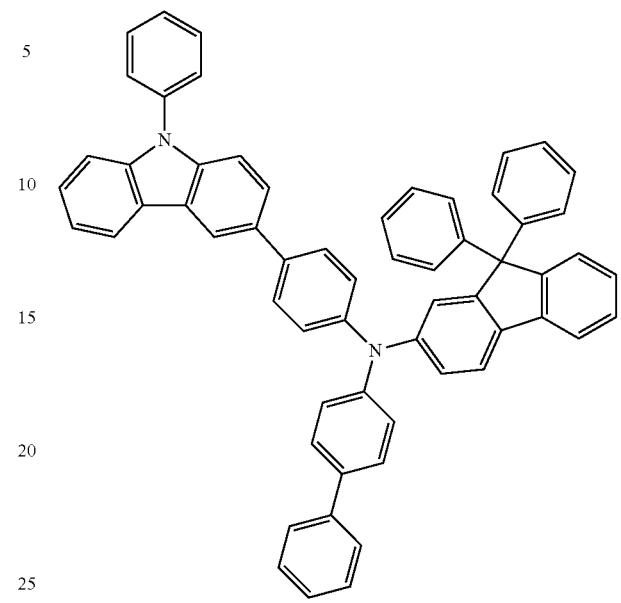
HT6
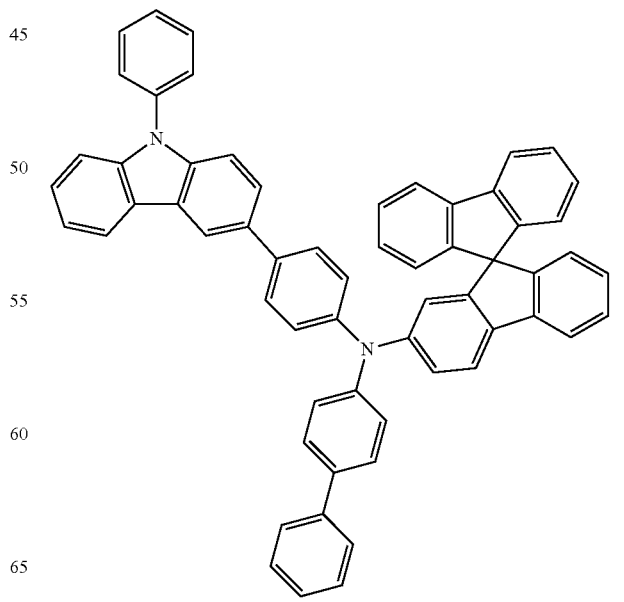

95
-continued
HT7
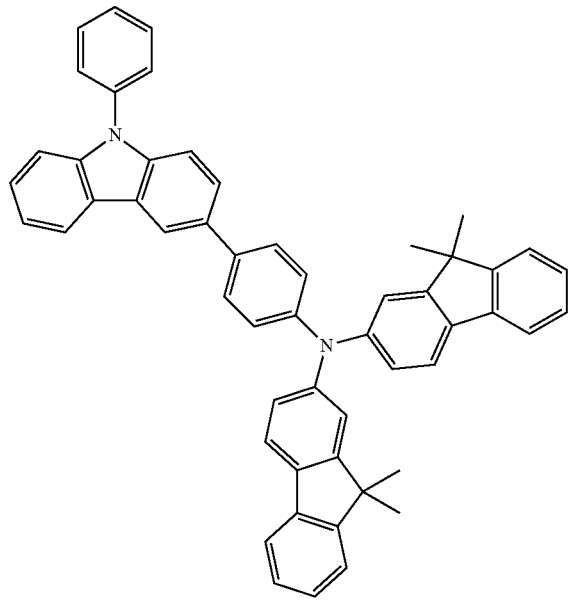
96
-continued
HT9
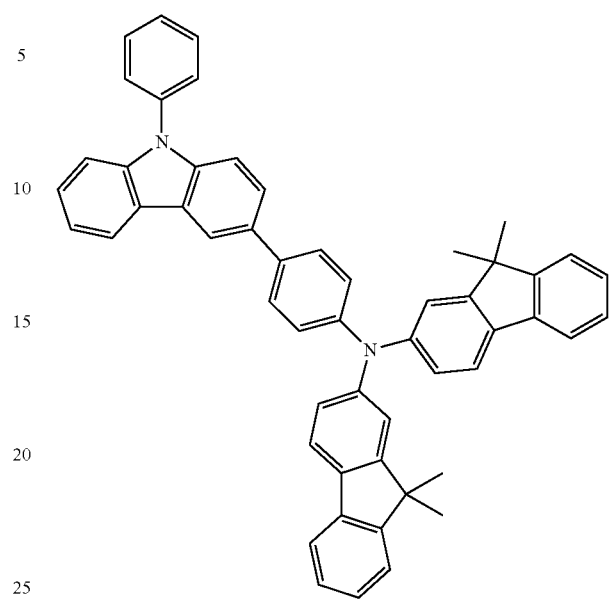
HT8
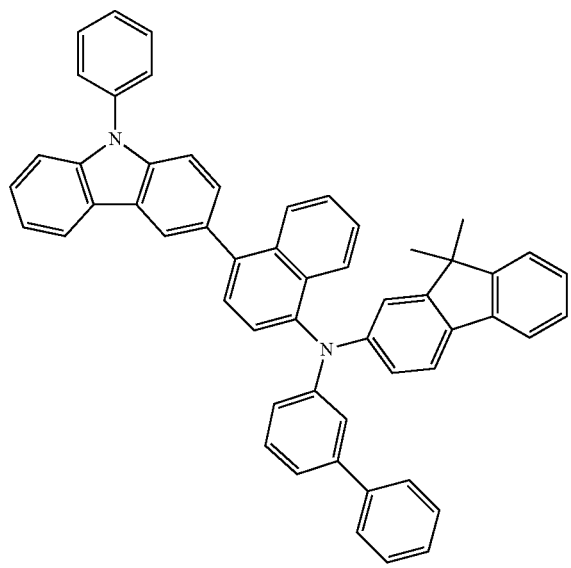
HT10
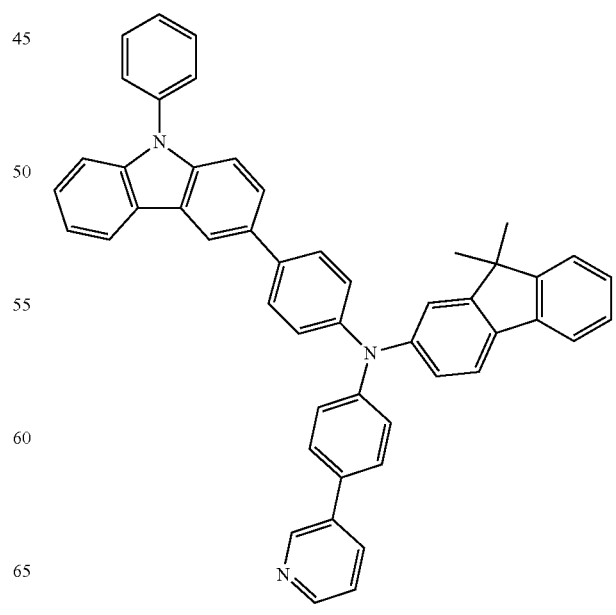

HT11
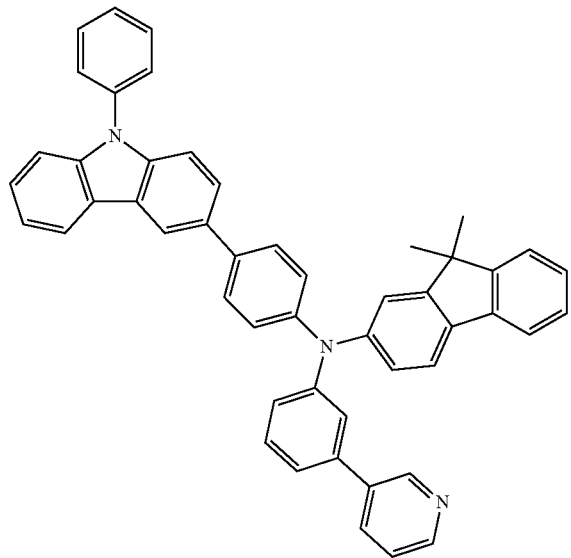
HT12
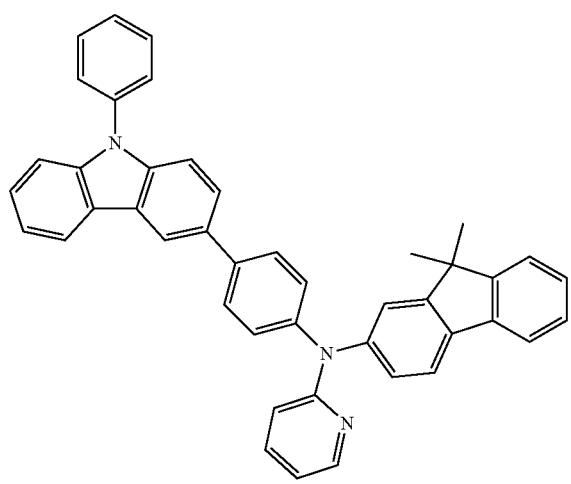
HT13
HT14
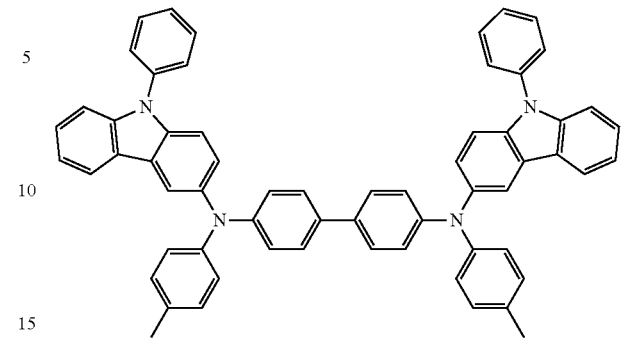
HT15
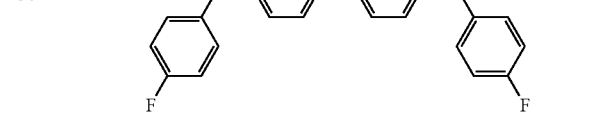
HT16
HT-17
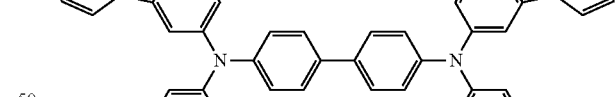

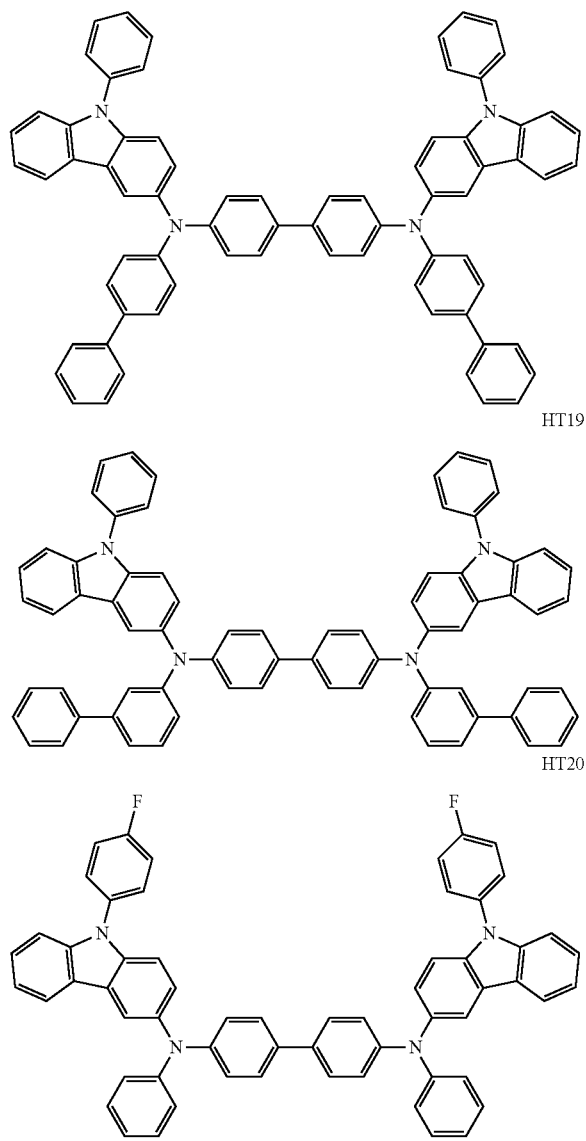

HT18

HT19

HT20

A thickness of the hole transport region may be from about 100 Angstrom (Å) to about 10,000 Å, and in some embodiments, from about 100 Å to about 1,000 Å. When the hole transport region includes a HIL and a HTL, a thickness of the HIL may be from about 100 Å to about 10,000 Å, and in some embodiments, from about 100 Å to about 1,000 Å, and a thickness of the HTL may be from about 50 Å to about 2,000 Å, and in some embodiments, from about 100 Å to about 1,500 Å. When the thicknesses of the hole transport region, the HIL, and the HTL are within these ranges, satisfactory hole transport characteristics may be obtained without a substantial increase in driving voltage.

The hole transport region may further include a charge-generating material to improve conductivity, in addition to the materials as described above. The charge-generating material may be homogeneously or non-homogeneously dispersed in the hole transport region.

The charge-generating material may be, for example, a p-dopant. The p-dopant may be one of a quinine derivative, a metal oxide, and a cyano group-containing compound, but is not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and cyano-containing compounds such as Compound 200 below.

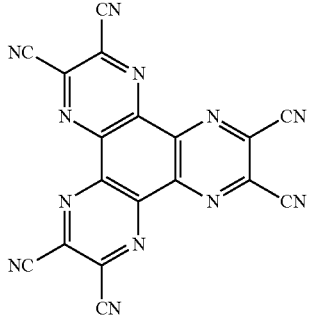

Compound HT-D1

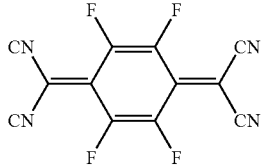

F4-TCNQ

The hole transport region may further include a buffer layer.

The buffer layer may compensate for an optical resonance distance of light according to a wavelength of the light emitted from the EML, and thus may increase efficiency.

The EML may be formed on the hole transport region by using vacuum deposition, spin coating, casting, LB deposition, or the like. When the EML is formed using vacuum deposition or spin coating, the conditions for deposition and coating may be similar to those for the formation of the HIL, though the conditions for the deposition and coating may vary depending on the material that is used to form the EML.

The EML may include a host and a dopant. The host may include at least one of the carbazole-based compounds represented by Formula 1A or 1B above.

The host may further include at least one of TPBi, TBADN, ADN (also referred to as "DNA"), CBP, CDBP, and TCP, in addition to the carbazole-based compound of Formula 1A or 1B:

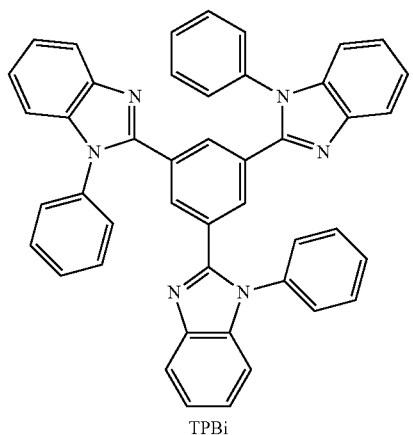

TPBi

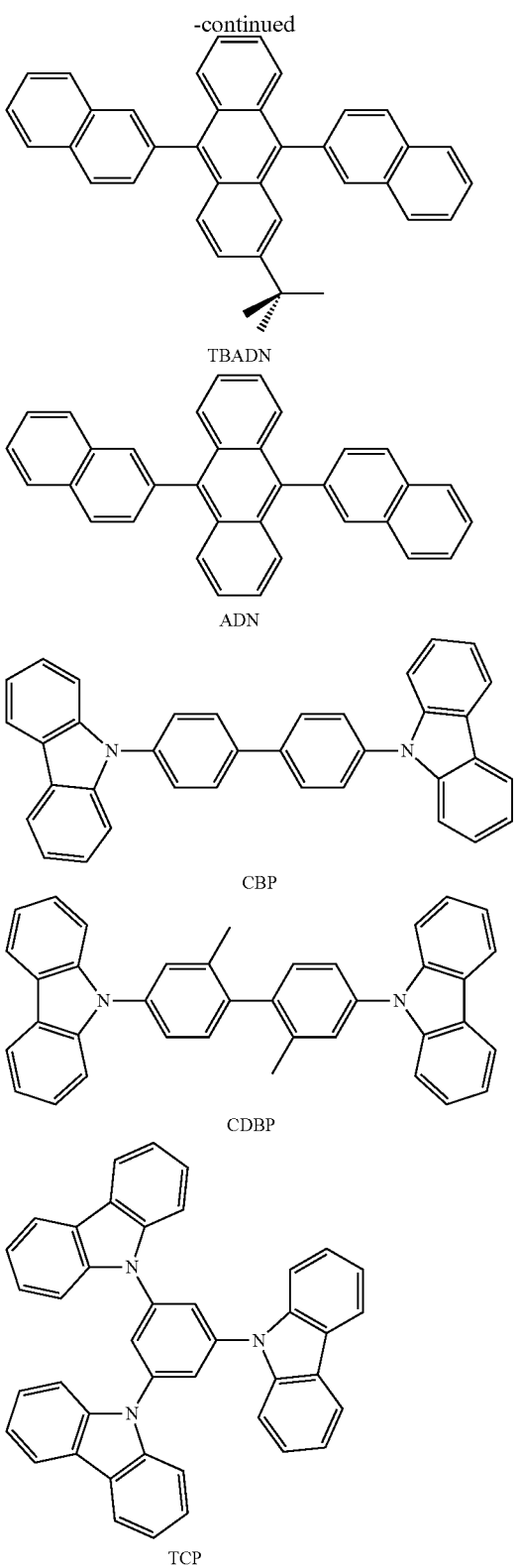

TBADN

ADN

CBP

CDBP

TCP

When the organic light-emitting device is a full color organic light-emitting device, the emission layer may be patterned into a red emission layer, a green emission layer, and a blue emission layer. In some embodiments, the EML may have a stack structure including a red emission layer, a green emission layer, and/or a blue emission layer that are stacked upon one another to emit white light, but is not limited thereto. A host of at least one of the red emission layer, the green emission layer, and the blue emission layer may include the carbazole-based compounds of Formula 1A or 1B. For example, the host of the green emission layer may include the carbazole-based compounds of Formula 1A or 1B.

The EML of the light-emitting device may include a dopant, which may be a fluorescent dopant emitting light based on fluorescence mechanism, or a phosphorescent dopant emitting light based on phosphorescence mechanism.

In some embodiments, the EML may include a host including the carbazole-based compounds of Formula 1A or 1B, and a phosphorescent dopant. The phosphorescent dopant may include an organometallic complex including a transition metal, for example, iridium (Ir), platinum (Pt), osmium (Os), or rhodium (Rh).

For example, the phosphorescent dopant may include an organometallic compound represented by Formula 81 below, but is not limited thereto:

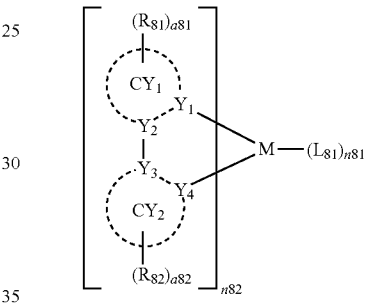

Formula 81

In Formula 81,

M may be iridium (Ir), platinum (Pt), osmium (Os), titanium (Ti), zirconium (Zr), hafnium (Hf), europium (Eu), terbium (Tb), or thulium (Tm);

$Y_1$ to $Y_4$ may be each independently a carbon (C) or a nitrogen (N);

$Y_1$ and $Y_2$ may be linked to each other via a single bond or a double bond, and $Y_3$ and $Y_4$ may be linked to each other via a single bond or a double bond;

$CY_1$ and $CY_2$ may be each independently a benzene, a naphthalene, a fluorene, a spiro-fluorene, an indene, a pyrrole, a thiophene, a furan, an imidazole, a pyrazole, a thiazole, an isothiazole, an oxazole, an isooxazole, a pyridine, a pyrazine, a pyrimidine, a pyridazine, a quinoline, an isoquinoline, a benzoquinoline, a quinoxaline, a quinazoline, a carbazole, a benzoimidazole, a benzofuran, a benzothiophene, an isobenzothiophene, a benzooxazole, an isobenzooxazole, a triazole, a tetrazole, an oxadiazole, a triazine, a dibenzofuran, or a dibenzothiophene, wherein $CY_1$ and $CY_2$ may be optionally linked to each other via a single bond or an organic linking group;

$R_{81}$ and $R_{82}$ may be each independently a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent nonaromatic condensed polycyclic group, a substituted or unsubstituted monovalent nonaromatic condensed heteropolycyclic group, —N($Q_1$)($Q_2$), —Si($Q_3$)($Q_4$)($Q_5$), or —B($Q_6$)($Q_7$);

a81 and a82 may be each independently an integer selected from 1 to 5;

n81 may be an integer selected from 0 to 4;

n82 may be 1, 2, or 3;

$L_{81}$ may be a monovalent organic ligand, a divalent organic ligand, or a trivalent organic ligand.

Substituents $R_{81}$ and $R_{82}$ in Formula 81 are the same as described above with reference to $R_1$.

The phosphorescent dopant may include at least one of Compounds PD1 to PD74, but is not limited thereto:

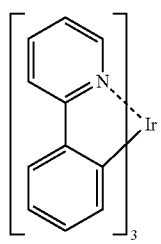

PD1

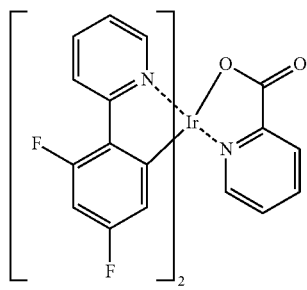

PD2

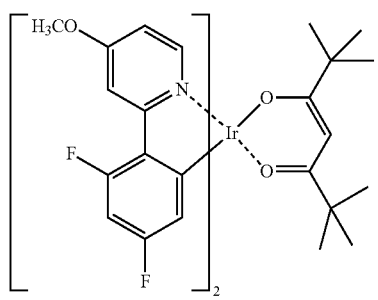

PD3

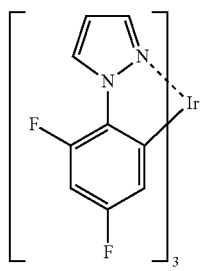

PD4

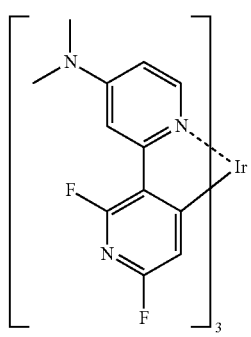

PD5

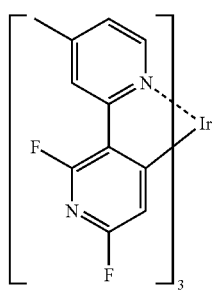

PD6

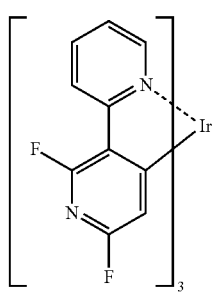

PD7

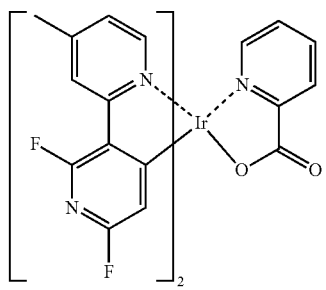

PD8

-continued
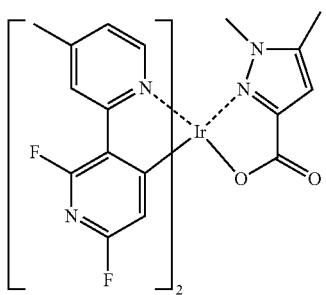
PD9
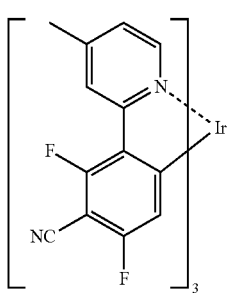
PD10
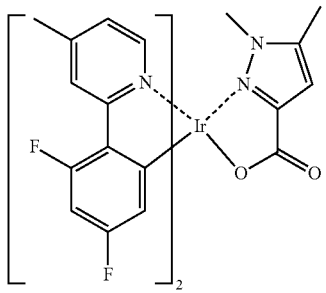
PD11
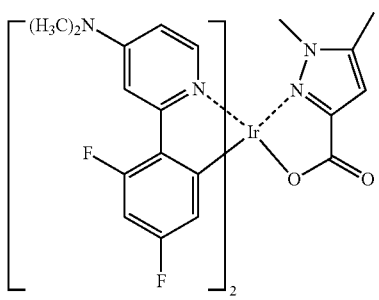
PD12
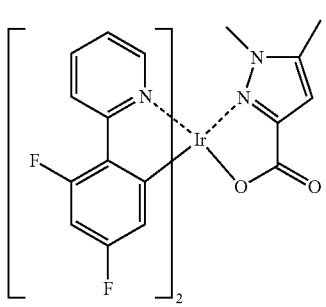
PD13
-continued
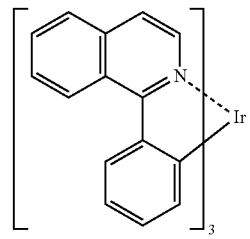
PD14
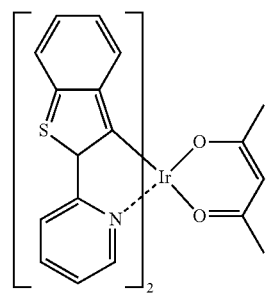
PD15
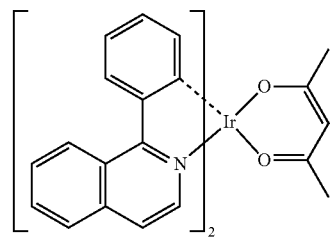
PD16
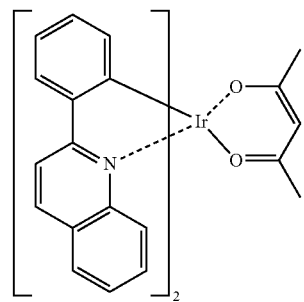
PD17
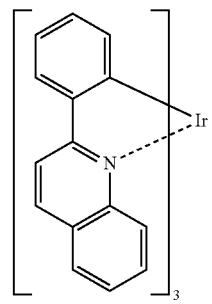
PD18

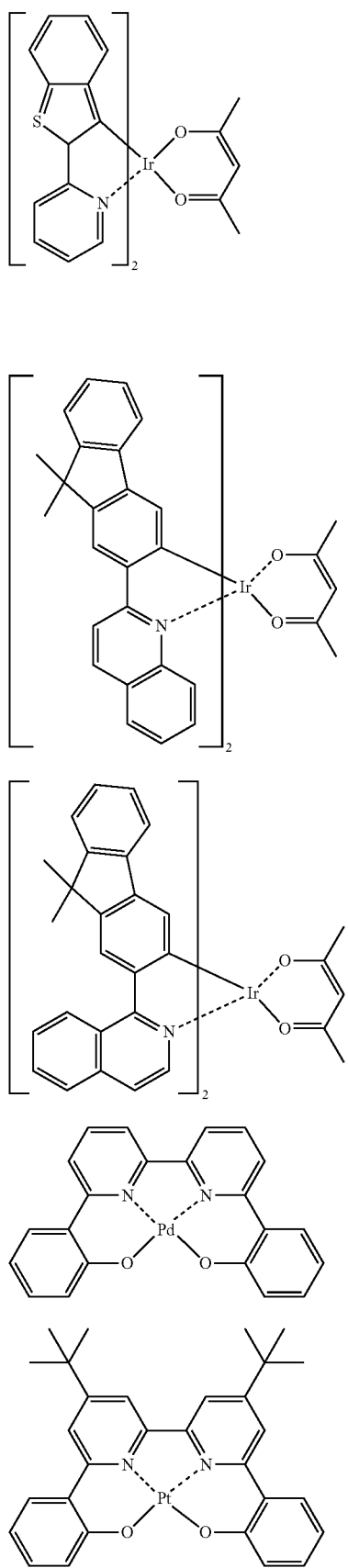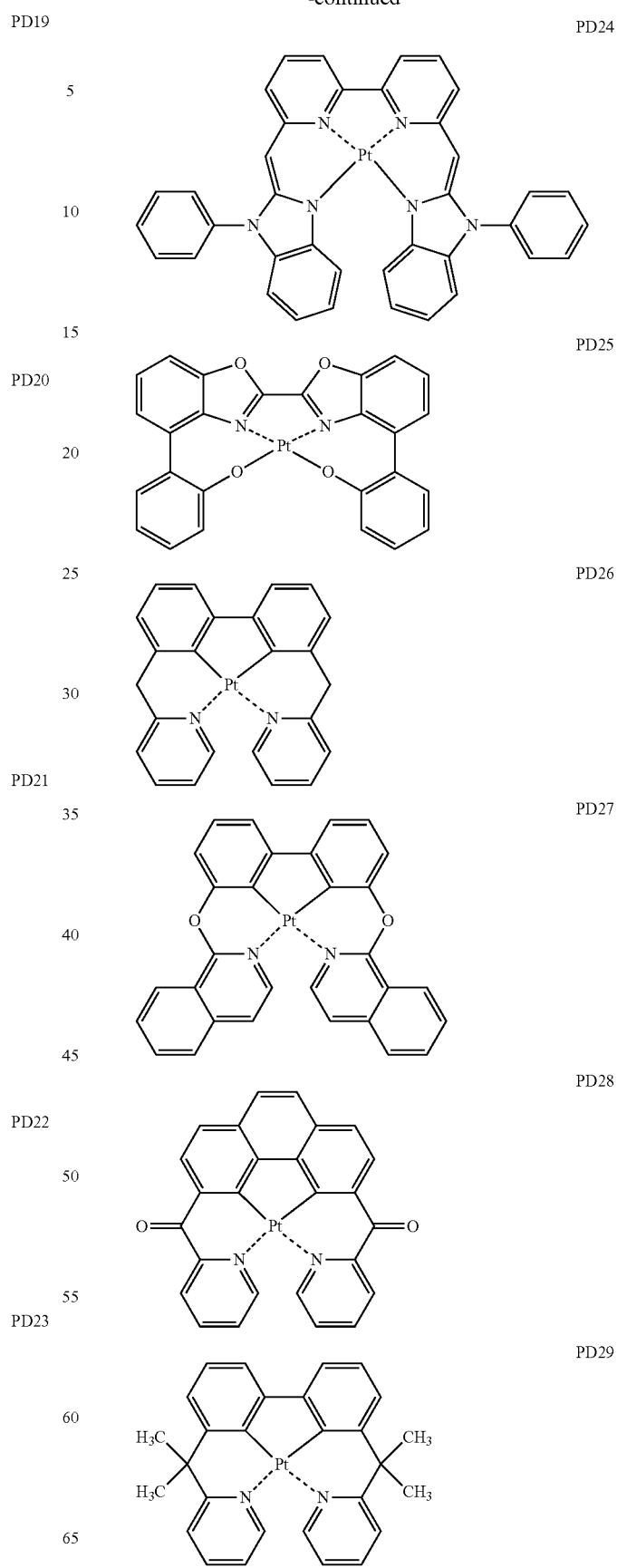

-continued
PD30 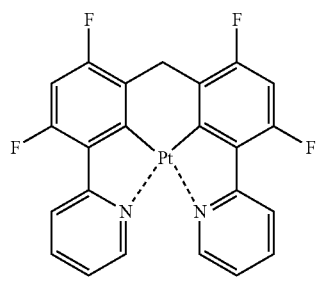
PD31 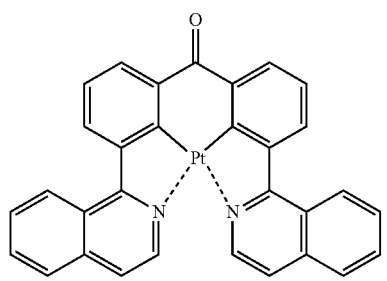
PD32 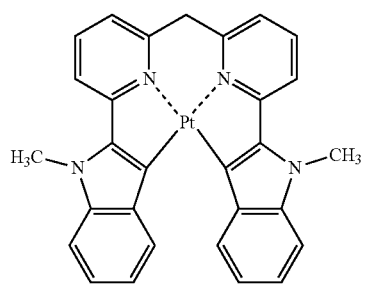
PD33 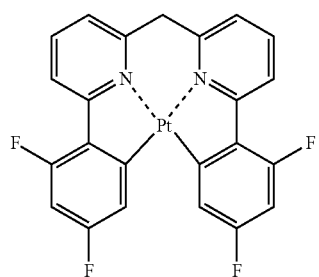
PD34 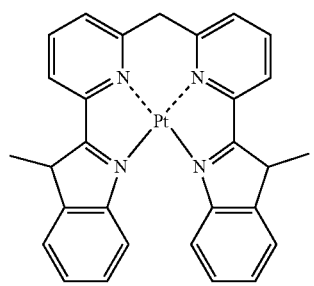
-continued
PD35 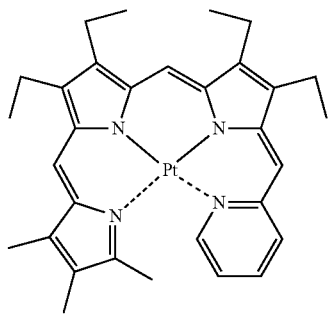
PD36 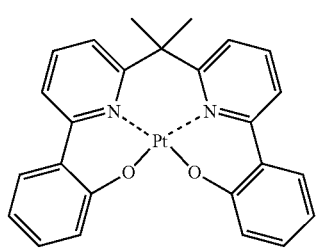
PD37 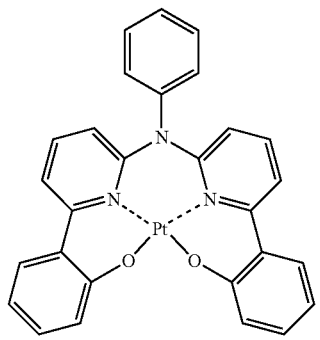
PD38 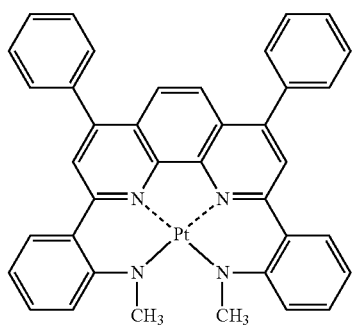
PD39 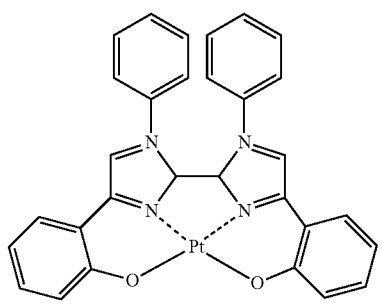

-continued
PD40
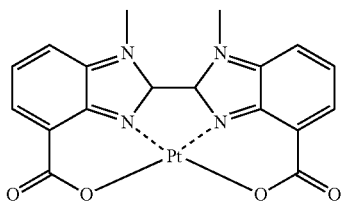
PD41
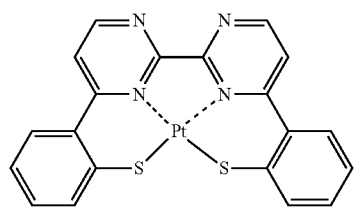
PD42
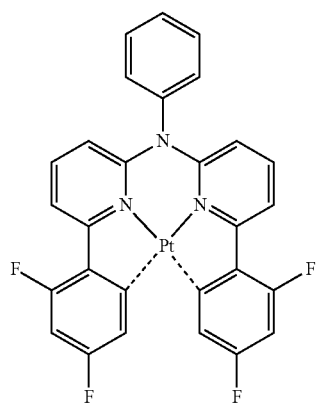
PD43
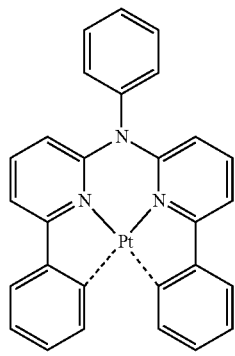
PD44
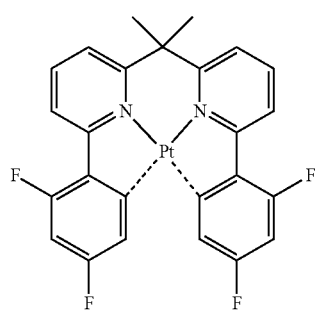
-continued
PD45
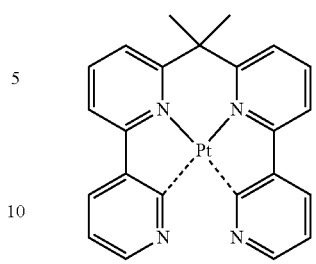
PD46
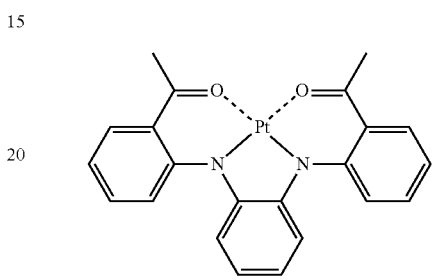
PD47
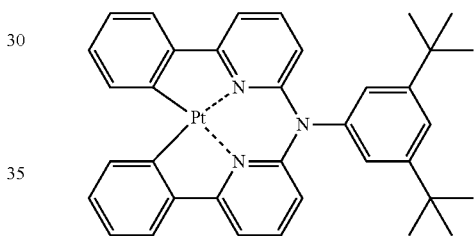
PD48
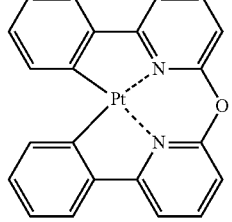
PD49
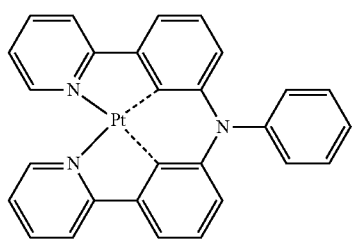
PD50
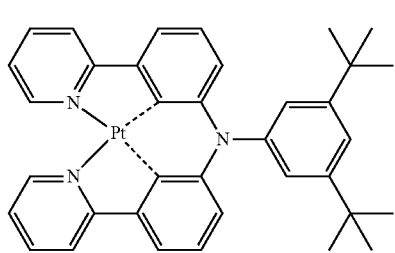

PD51 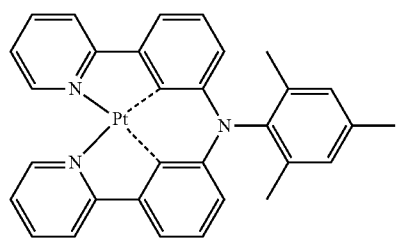
PD57 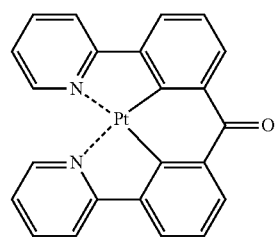
PD52 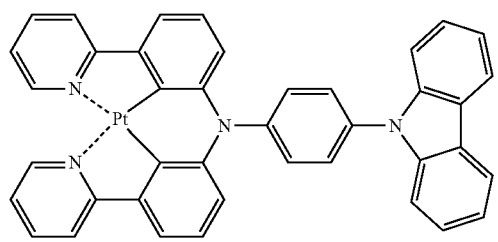
PD53 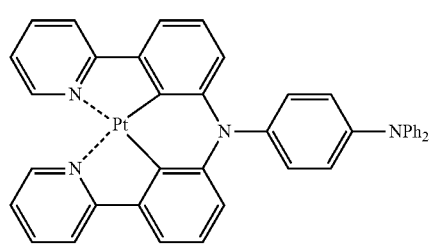
PD58 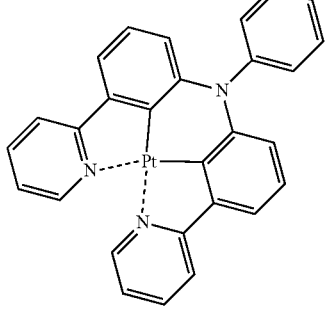
PD54 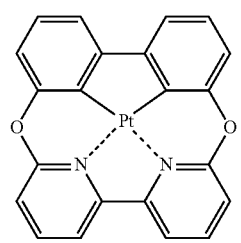
PD55 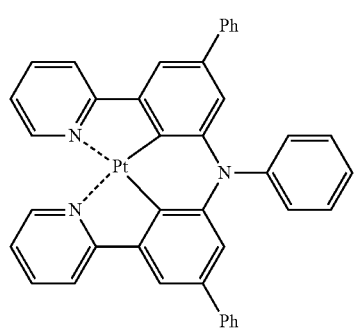
PD59 
PD60 
PD56 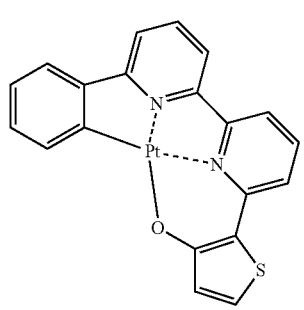
PD61 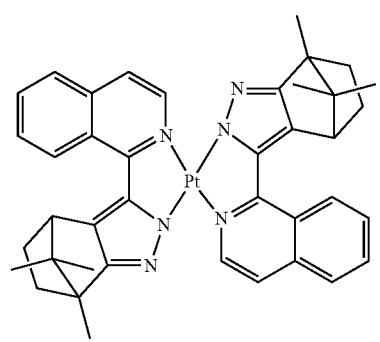

PD62 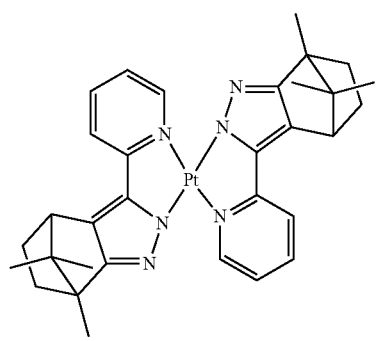
PD63 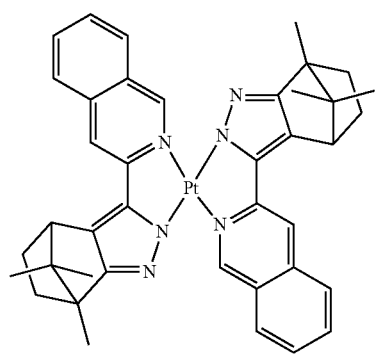
PD64 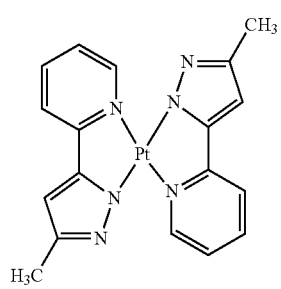
PD65 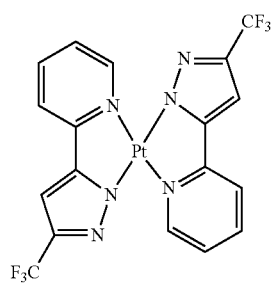
PD66 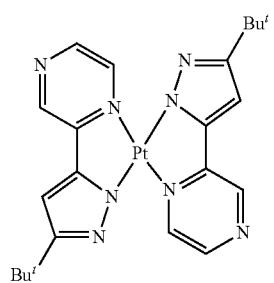
PD67 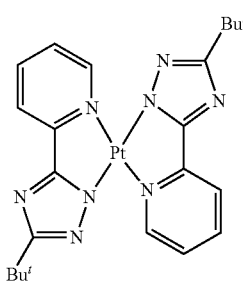
PD68 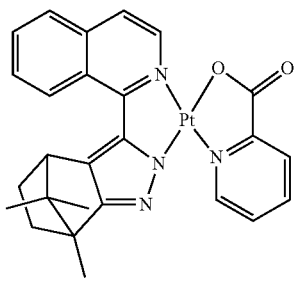
PD69 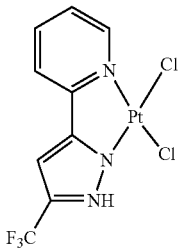
PD70 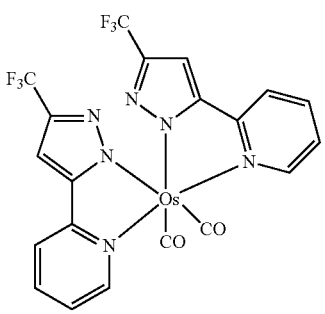
PD71 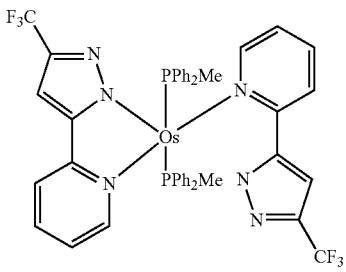

-continued
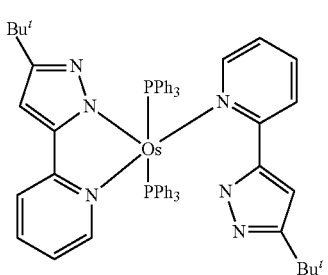
PD72
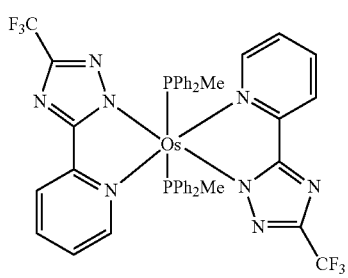
PD73
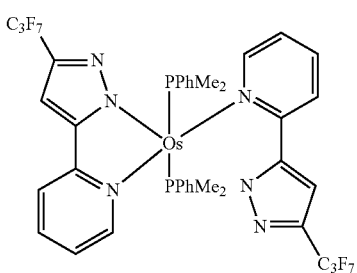
PD74
Compound PD 1 is Ir(ppy)$_3$.
In some embodiments, the phosphorescent dopant may include PtOEP or Compound PhGD represented below:
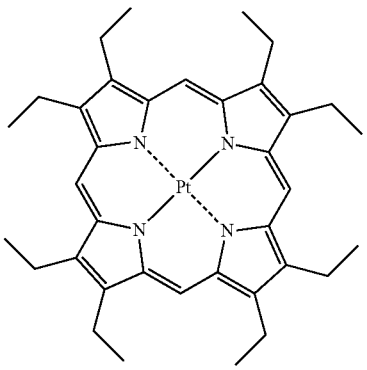
PtOEP
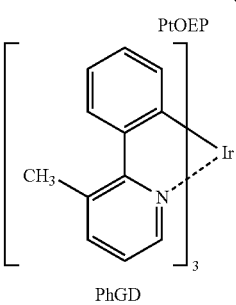
PhGD
In some other embodiments, the phosphorescent dopant may include at least one of DPAVBi, BDAVBi, TBPe, DCM, DCJTB, Coumarin 6, and C545T represented below.
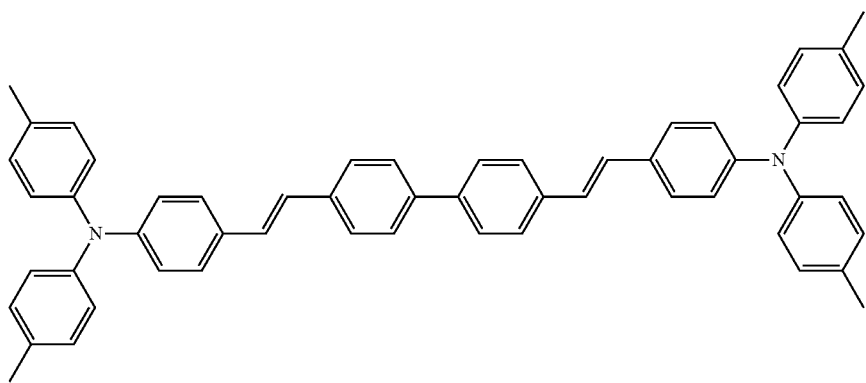
DPAVBi
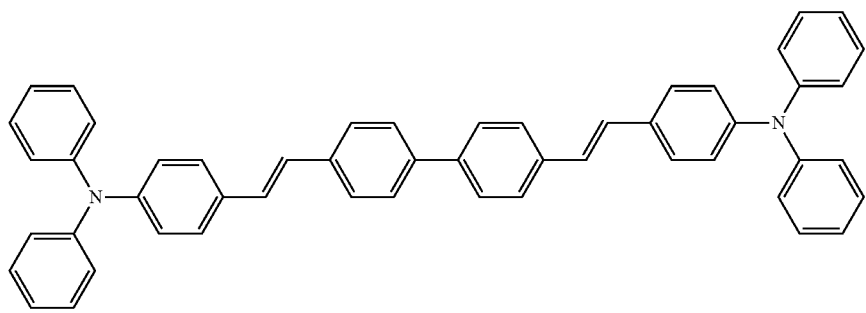
BDAVBi -continued

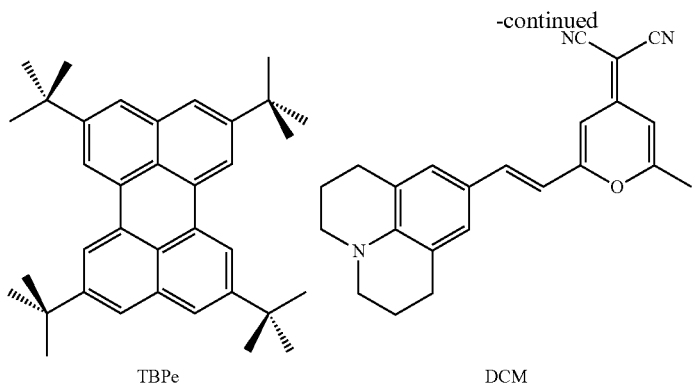

TBPe                    DCM

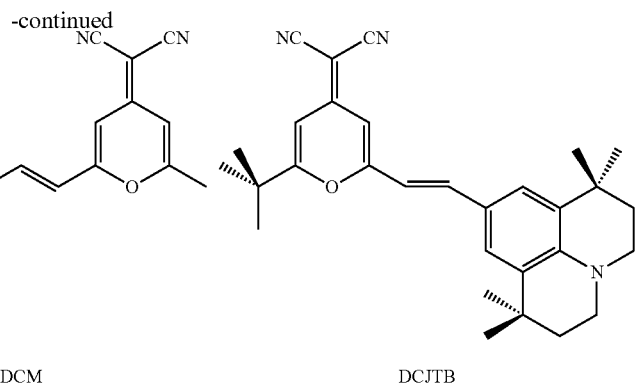

DCJTB

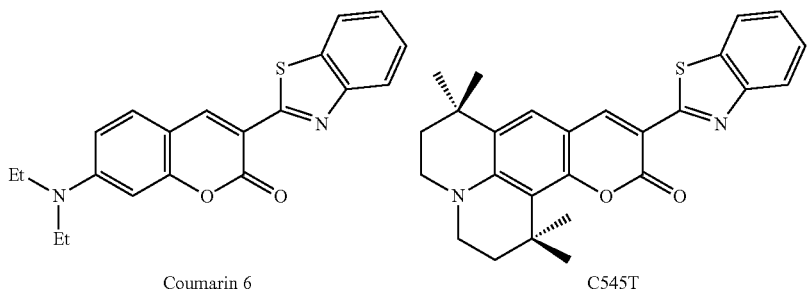

Coumarin 6              C545T

When the EML includes both a host and a dopant, the amount of the dopant may be from about 0.01 to about 15 parts by weight based on 100 parts by weight of the host. However, the amount of the dopant is not limited to this range.

The thickness of the EML may be about 100 Å to about 1,000 Å, and in some embodiments, may be from about 200 Å to about 600 Å. When the thickness of the EML is within these ranges, the EML may have improved light emitting ability without a substantial increase in driving voltage.

Next, the electron transport region may be disposed on the EML.

The electron transport region may include at least one of a HBL, an ETL, and an EIL.

In some embodiments, the electron transport region may have a structure including a HBL/ETL/EIL or a ETL/EIL, wherein the layers forming the structure of the electron transport region may be sequentially stacked on the EML in the stated order. However, embodiments of the present disclosure are not limited thereto. The ETL may have a single-layer structure or a multi-layer structure including at least two different layers.

Conditions for forming the HBL, ETL, and EIL of the electron transport region may be defined based on the above-described formation conditions for the HIL.

When the electron transport region includes the HBL, the HBL may include at least one of BCP, Bphen, BAlq represented below. However, embodiments of the present disclosure are not limited thereto.

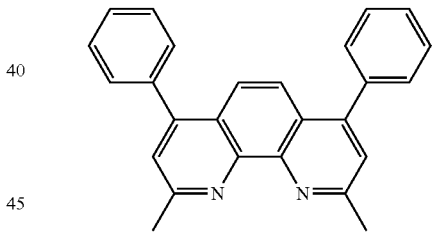

BCP

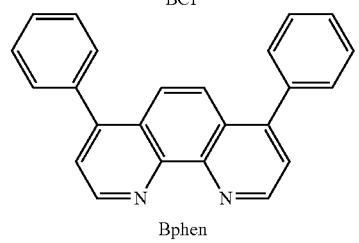

Bphen

A thickness of the HBL may be from about 20 Å to about 1,000 Å, and in some embodiments, from about 30 Å to about 300 Å. When the thickness of the HBL is within these ranges, the HBL may have improved hole blocking ability without a substantial increase in driving voltage.

The ETL may further include at least one of $Alq_3$, Balq, TAZ, and NTAZ below, in addition to BCP and Bphen described above.

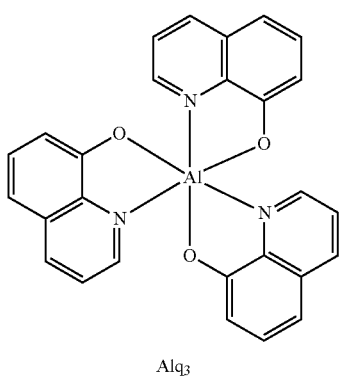

Alq₃

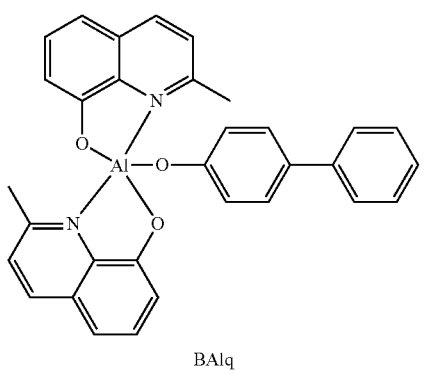

BAlq

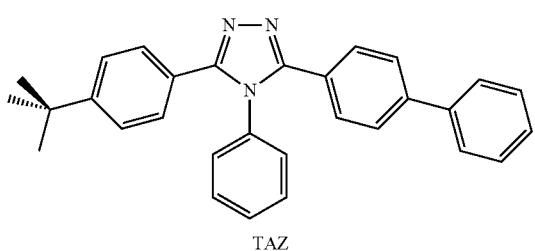

TAZ

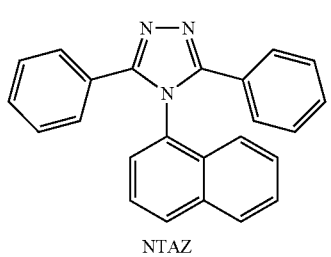

NTAZ

In some embodiments, the ETL may include at least one of Compounds ET1 and ET2 represented below, but is not limited thereto.

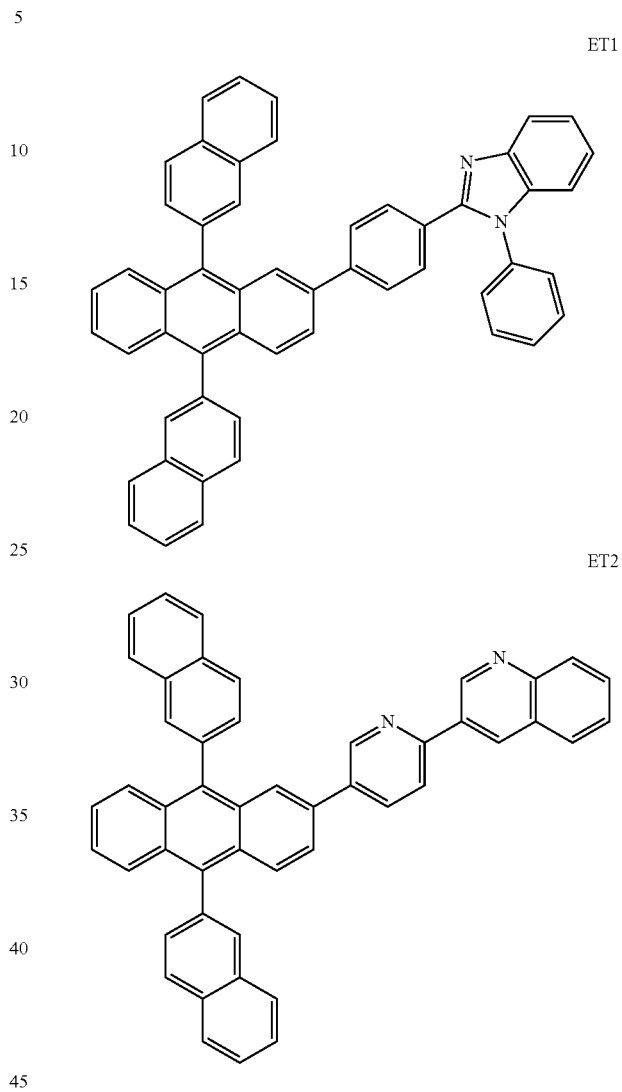

ET1

ET2

A thickness of the ETL may be from about 100 Å to about 1,000 Å, and in some embodiments, from about 150 Å to about 500 Å. When the thickness of the ETL is within these ranges, the ETL may have satisfactory electron transporting ability without a substantial increase in driving voltage.

In some embodiments the ETL may further include a metal-containing material, in addition to the above-described materials.

The metal-containing material may include a lithium (Li) complex. Non-limiting examples of the Li complex are compound ET-D1 below (lithium quinolate (LiQ)), or compound ET-D2 below.

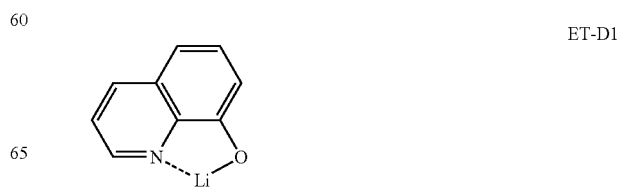

ET-D1

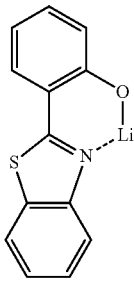

ET-D2

The electron transport region may include an EIL that may facilitate injection of electrons from the second electrode 19. The EIL may include at least one selected from LiF, NaCl, CsF, Li$_2$O, and BaO. The thickness of the EIL may be from about 1 Å to about 100 Å, and in some embodiments, from about 3 Å to about 90 Å. When the thickness of the EIL is within these ranges, the EIL may have satisfactory electron injection ability without a substantial increase in driving voltage.

The second electrode 19 is disposed on the organic layer 15. The second electrode 19 may be a cathode. A material for the second electrode 19 may be a metal, an alloy, or an electrically conductive compound that have a low work function, or a combination thereof. Non-limiting examples of the material for the second electrode 19 are lithium (Li), magnesium (Mg), aluminum (Al), aluminum (Al)-lithium (Li), calcium (Ca), magnesium (Mg)-indium (In), and magnesium (Mg)-silver (Ag), or the like. In some embodiments, to manufacture a top-emission light-emitting device, the second electrode 19 may be formed as a transmissive electrode from, for example, indium tin oxide (ITO) or indium zinc oxide (IZO).

Although the organic light-emitting device of FIG. 1 is described above, embodiments of the present disclosure are not limited thereto.

As used herein, a $C_1$-$C_{60}$ alkyl group refers to a linear or branched aliphatic hydrocarbon monovalent group having 1 to 60 carbon atoms. Non-limiting examples of the $C_1$-$C_{60}$ alkyl group a methyl group, an ethyl group, a propyl group, an isobutyl group, a sec-butyl group, a tert-butyl group, a pentyl group, an iso-amyl group, and a hexyl group. A $C_1$-$C_{60}$ alkylene group refers to a divalent group having the same structure as the $C_1$-$C_{60}$ alkyl.

As used herein, a $C_1$-$C_{60}$ alkoxy group refers to a monovalent group represented by —$OA_{101}$ (where $A_{101}$ is a $C_1$-$C_{60}$ alkyl group as described above. Non-limiting examples of the $C_1$-$C_{60}$ alkoxy group are a methoxy group, an ethoxy group, and an isopropyloxy group.

As used herein, a $C_2$-$C_{60}$ alkenyl group refers to a structure including at least one carbon double bond in the middle or at the terminal of the $C_2$-$C_{60}$ alkyl group. Non-limiting examples of the $C_2$-$C_{60}$ alkenyl group are an ethenyl group, a propenyl group, and a butenyl group. A $C_2$-$C_{60}$ alkylene group refers to a divalent group having the same structure as the $C_2$-$C_{60}$ alkenyl group.

As used herein, a $C_2$-$C_{60}$ alkynyl group refers to a structure including at least one carbon triple bond in the middle or at the terminal of the $C_2$-$C_{60}$ alkyl group. Non-limiting examples of the $C_2$-$C_{60}$ alkynyl group are an ethynyl group and a propynyl group. A $C_2$-$C_{60}$ alkynylene group used herein refers to a divalent group having the same structure as the $C_2$-$C_{60}$ alkynyl group.

As used herein, a $C_3$-$C_{10}$ cycloalkyl group refers to a monovalent, monocyclic hydrocarbon group having 3 to 10 carbon atoms. Non-limiting examples of the $C_3$-$C_{10}$ cycloalkyl group are a cyclopropyl group, a cyclobutyl group, a cyclopentyl group, a cyclohexyl group, and a cycloheptyl group. A $C_3$-$C_{10}$ cycloalkylene group refers to a divalent group having the same structure as the $C_3$-$C_{10}$ cycloalkyl group.

As used herein, a $C_2$-$C_{10}$ heterocycloalkyl group refers to a monovalent monocyclic group having 2 to 10 carbon atoms in which at least one hetero atom selected from N, O, P, and S is included as a ring-forming atom. Non-limiting examples of the $C_2$-$C_{10}$ heterocycloalkyl group are a tetrahydrofuranyl group and a tetrahydrothiophenyl group. A $C_2$-$C_{10}$ heterocycloalkylene group refers to a divalent group having the same structure as the $C_2$-$C_{10}$ heterocycloalkyl group.

As used herein, a $C_3$-$C_{10}$ cycloalkenyl group refers to a monovalent monocyclic group having 3 to 10 carbon atoms that includes at least one double bond in the ring but does not have aromaticity. Non-limiting examples of the $C_3$-$C_{10}$ cycloalkenyl group are a cyclopentenyl group, a cyclohexenyl group, and a cycloheptenyl group. A $C_3$-$C_{10}$ cycloalkenylene group refers to a divalent group having the same structure as the $C_3$-$C_{10}$ cycloalkenyl group.

As used herein, a $C_2$-$C_{10}$ heterocycloalkenyl group used herein refers to a monovalent monocyclic group having 2 to 10 carbon atoms that includes at least one double bond in the ring and in which at least one hetero atom selected from N, O, P, and S is included as a ring-forming atom. Non-limiting examples of the $C_2$-$C_{10}$ heterocycloalkenyl group are a 2,3-dihydrofuranyl group and a 2,3-dihydrothiophenyl group. A $C_2$-$C_{10}$ heterocycloalkenylene group used herein refers to a divalent group having the same structure as the $C_3$-$C_{10}$ heterocycloalkenyl group.

As used herein, a $C_6$-$C_{60}$ aryl group refers to a monovalent, aromatic carbocyclic aromatic group having 6 to 60 carbon atoms, and a $C_6$-$C_{60}$ arylene group refers to a divalent, aromatic carbocyclic group having 6 to 60 carbon atoms. Non-limiting examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group include at least two rings, the rings may be fused to each other.

As used herein, a $C_2$-$C_{60}$ heteroaryl group refers to a monovalent, aromatic carbocyclic aromatic group having 2 to 60 carbon atoms in which at least one hetero atom selected from N, O, P, and S is included as a ring-forming atom, and 2 to 60 carbon atoms. A $C_2$-$C_{60}$ heteroarylene group refers to a divalent, aromatic carbocyclic group having 2 to 60 carbon atoms in which at least one hetero atom selected from N, O, P, and S is included as a ring-forming atom. Non-limiting examples of the $C_2$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_2$-$C_{60}$ heteroaryl and the $C_2$-$C_{60}$ heteroarylene include at least two rings, the rings may be fused to each other.

As used herein, a $C_6$-$C_{60}$ aryloxy group indicates —$OA_{102}$ (where $A_{102}$ is a $C_6$-$C_{60}$ aryl group as described above), and a $C_6$-$C_{60}$ arylthio group indicates —$SA_{103}$ (where $A_{103}$ is a $C_6$-$C_{60}$ aryl group as described above).

As used herein, a monovalent non-aromatic condensed polycyclic group refers to a monovalent group having at least two rings condensed to each other, in which only carbon atoms (for example, 8 to 60 carbon atoms) are exclusively included as ring-forming atoms, and wherein the entire molecule is non-aromatic. A non-limiting example of the monovalent non-aromatic condensed polycyclic group is a fluorenyl group. A divalent non-aromatic condensed polycyclic group refers to a divalent group having the same structure as the monovalent non-aromatic condensed polycyclic group.

As used herein, a monovalent non-aromatic condensed heteropolycyclic group refers to a monovalent group having at least two rings condensed to each other, in which both carbon atoms (for example, 8 to 60 carbon atoms) and heteroatoms are included as ring-forming atoms, and wherein the entire molecule is non-aromatic. A non-limiting example of the monovalent non-aromatic condensed heteropolycyclic group is a carbazolyl group. A divalent non-aromatic condensed heteropolycyclic group refers to a divalent group having the same structure as the monovalent non-aromatic condensed heteropolycyclic group.

As used herein, at least one substituent of the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent nonaromatic condensed polycyclic group, the substituted divalent nonaromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent nonaromatic condensed polycyclic group, and the substituted monovalent nonaromatic condensed heteropolycyclic group may be selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, a monovalent nonaromatic condensed heteropolycyclic group, —Si($Q_{11}$)($Q_{12}$)($Q_{13}$), and —B($Q_{14}$)($Q_{15}$), a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, and a monovalent nonaromatic condensed heteropolycyclic group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, a monovalent nonaromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, a monovalent nonaromatic condensed heteropolycyclic group, —Si($Q_{21}$)($Q_{22}$)($Q_{23}$), and —B($Q_{24}$)($Q_{25}$), and
—Si($Q_{31}$)($Q_{32}$)($Q_{33}$), and —B($Q_{34}$)($Q_{35}$), wherein $Q_1$ to $Q_5$, $Q_{11}$ to $Q_{15}$, $Q_{21}$ to $Q_{25}$, and $Q_{31}$ to $Q_{35}$ are each independently selected from a hydrogen, $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent nonaromatic condensed polycyclic group, and a monovalent nonaromatic condensed heteropolycyclic group.

For example, at least one substituent of the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent nonaromatic condensed polycyclic group, the substituted divalent nonaromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent nonaromatic condensed polycyclic group, and the substituted monovalent nonaromatic condensed heteropolycyclic group may be selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a cyclopentyl group, a cyclohexyl group, a cycloheptyl group, a cyclooctyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, an imidazopyridinyl group, $-Si(Q_{11})(Q_{12})(Q_{13})$, and $-B(Q_{14})(Q_{15})$, a cyclopentyl group, a cyclohexyl group, a cycloheptyl group, a cyclooctyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, and an imidazopyridinyl group, a cyclopentyl group, a cyclohexyl group, a cycloheptyl group, a cyclooctyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, and an imidazopyridinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent nonaromatic condensed polycyclic group, a monovalent nonaromatic condensed heteropolycyclic group, $-Si(Q_{21})(Q_{22})(Q_{23})$, and $-B(Q_{24})(Q_{25})$, and $-Si(Q_{31})(Q_{32})(Q_{33})$, and $-B(Q_{34})(Q_{35})$, wherein $Q_1$ to $Q_5$, $Q_{11}$ to $Q_{15}$, $Q_{21}$ to $Q_{25}$, and $Q_{31}$ to $Q_{35}$ are each independently selected from a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, and an imidazopyridinyl group, each substituted with at least one of from a hydrogen, $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclooctyl group, a cyclopentenyl group, a cyclohexenyl group, a cycloheptenyl group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group. However, embodiments of the present disclosure are not limited thereto.

One or more embodiments of the present disclosure, which include condensed cyclic compounds, and organic light-emitting devices including the same, will now be described in detail with reference to the following examples.

However, these examples are only for illustrative purposes and are not intended to limit the scope of the one or more embodiments of the present disclosure. In the following synthesis example, the expression that "'B' instead of 'A' was used" means that the amounts of 'B' and 'A' were the same in equivalent amounts.

EXAMPLES

Synthesis Example 1: Synthesis of Compound 1

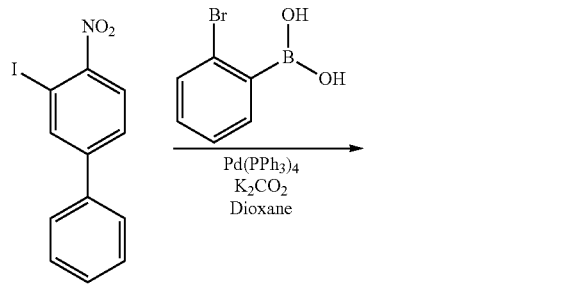

Intermediate A

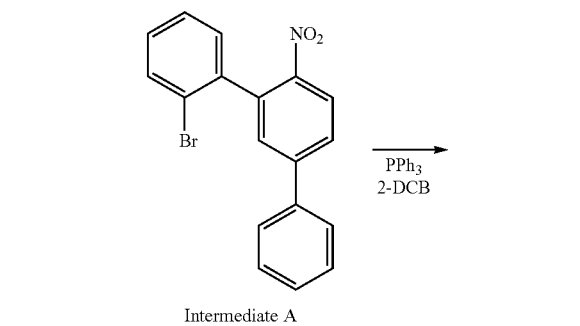

Intermediate B

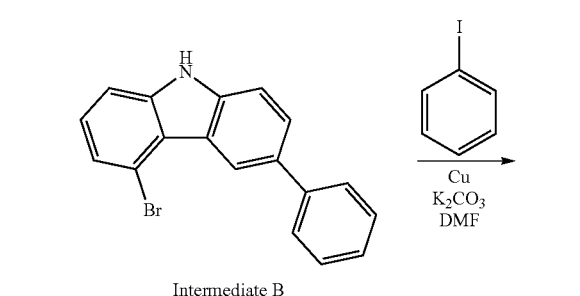

Intermediate C

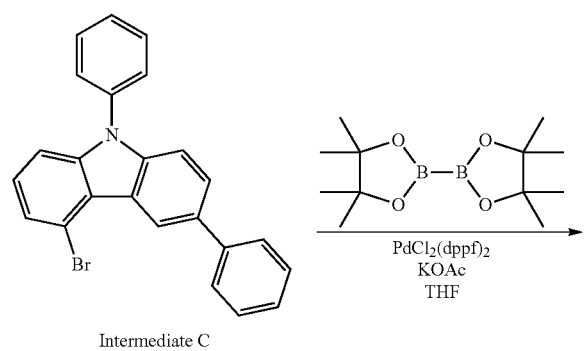

Intermediate D

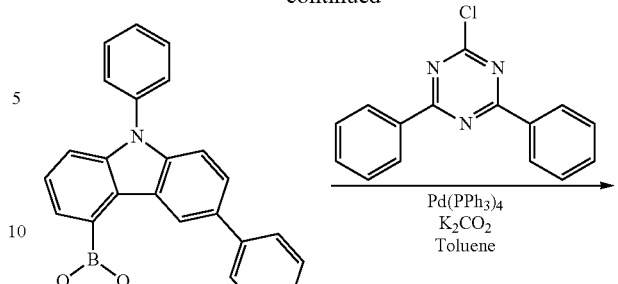

Compound 1

Synthesis of Intermediate A

After 20.1 g (61.8 mmol) of 3-iodo-4-nitro-1,1'-biphenyl, 18.6 g (92.7 mmol) of 2-bromophenyl)boronic acid, 2.4 g (9.2 mmol) of triphenylphosphine (PPh$_3$), 0.7 g (3.1 mmol) of tetrakis(triphenylphosphine)palladium(0) (Pd(PPh$_3$)$_4$), and 17.1 g (123.7 mmol) of potassium carbonate (K$_2$CO$_3$) were put into a 2-necked flask, 800 mL of toluene and 80 mL of H$_2$O were added thereto, followed by purging with argon and reflux for about 12 hours. The reaction product was cooled down to room temperature, followed by extraction with ethyl acetate (EA). An organic layer was collected, dried using magnesium sulfate (MgSO$_4$), and purified using column chromatography (hexane/EA=10/1) to obtain Intermediate A (47 g, Yield: 75%).

$^1$H NMR (CDCl$_3$, 300 MHz): 8.22 (d, 1H), 7.78 (dd, 1H), 7.70~7.64 (m, 3H), 7.56 (d, 1H), 7.52~7.39 (m, 4H), 7.33~7.26 (m, 2H).

Synthesis of Intermediate B

After 25.8 g (72.9 mmol) of Intermediate A and 57.4 g (218.8 mmol) of PPh$_3$ were put into a 1-necked flask, 80 mL of 1,2-dichlorobenzene (DCB) was added thereto, followed by purging with argon and stirring at about 150° C. for about 12 hours. After removing DCB by distillation, the resulting product was cooled down to room temperature, dissolved in a small amount of toluene, and purified using column chromatography (hexane) to obtain Intermediate B (15 g, Yield: 64%).

$^1$H NMR (CDCl$_3$, 300 MHz): 8.99 (s, 1H), 8.20 (b, 1H), 7.75~7.72 (m, 3H), 7.51~7.46 (m, 3H), 7.43~7.27 (m, 4H).

Synthesis of Intermediate C

After 32.0 g (99.3 mmol) of Intermediate B, 0.63 g (9.9 mmole) of Cu, and 27.1 g (198.6 mmol) of K$_2$CO$_3$ were put into a 2-necked flask, 320 mL of dimethylformamide (DMF) was added thereto, followed by purging with argon and addition of 22.5 mL (198.6 mmol) of iodobenzene. The resulting product was refluxed for about 12 hours, and cooled down to room temperature, followed by extraction with EA. An organic layer was collected, dried using magnesium sulfate (MgSO$_4$), and purified using column chromatography (hexane) to obtain Intermediate C in white solid form (25 g, Yield: 64%). Intermediate C was identified using $^1$H-nuclear magnetic resonance (NMR) and liquid chromatography-mass spectrometry (LC/MS).

$^1$H NMR (CDCl$_3$, 300 MHz): 9.07 (d, 1H), 7.75~7.71 (m, 3H), 7.69~7.61 (m, 2H), 7.55~7.40 (m, 7H), 7.37~7.31 (m, 2H), 7.26~7.22 (dd, 1H)

LC/MS, calcd.: C$_{24}$H$_{16}$BrN=398.29. found: m/z=398.1 (M+, 100%)

Synthesis of Intermediate D

After 33 g (83 mmol) of Intermediate C, 25 g (100 mmol) of 4,4,4',4',5,5,5',5'-octamethyl-2,2'-bi(1,3,2-dioxaborolane), 21 g (210 mmol) of potassium acetate (KOAc), and 3.4 g (4.2 mmol) of 1,1'-bis(diphenylphosphino)ferrocene-palladium(II)dichloride (PdCl$_2$(dppf)$_2$) were put into a 2-necked flask, and 200 mL of tetrahydrofuran (THF) was added thereto and stirred at about 70° C. for about 24 hours. After completion of the reaction, the reaction solution was extracted with water and EA. An organic layer was collected, dried using magnesium sulfate (MgSO$_4$), and purified using column chromatography (methylene chloride/n-hexane=3/2, Silica gel) to obtain Intermediate D in white solid form (26 g, Yield: 60%).

$^1$H NMR (CDCl$_3$, 300 MHz): 9.52 (s, 1H), 7.79~7.32 (m, 15H), 1.50 (s, 12H).

Synthesis of Compound 1

13.3 g (30 mmol) of Intermediate D, 7.3 g (27 mmol) of 2-chloro-4,6-diphenyl-1,3,5-triazine, 11 g (81 mmol) of K$_2$CO$_3$, and 1.5 g (1.3 mmol) of Pd(PPh$_3$)$_4$ were added to 50 mL of toluene and stirred at about 120° C. for about 24 hours. After completion of the reaction, water was added to the reaction product and stirred, followed by filtration to obtain a dark gray solid. This solid was dissolved in hot toluene, and then filtered. The resulting toluene solution was collected, and methanol was added thereto to obtain a precipitate. This precipitate was filtered to obtain a solid, which was then recrystallized with 1-chlorobenzene to obtain Compound 1 in yellow crystal form (11.0 g, Yield: 73%). Compound 1 was identified using LC/MS.

LC/MS, calcd.: C$_{39}$H$_{26}$N$_4$=550.65. found: m/z=550.2 (M+, 100%)

Synthesis Example 2: Synthesis of Compound 2

Compound 2 (yellow crystal, Yield: 67%) was synthesized in the same manner as in the synthesis of Compound 1 of Synthesis Example 1, except that 2-chloro-4,6-diphenylpyrimidine, instead of 2-chloro-4,6-diphenyl-1,3,5-triazine, was used.

Compound 2 was identified using LC/MS.

LC/MS, calcd.: C$_{40}$H$_{27}$N$_3$=549.66. found: m/z=549.2 (M+, 100%)

Synthesis Example 3: Synthesis of Compound 3

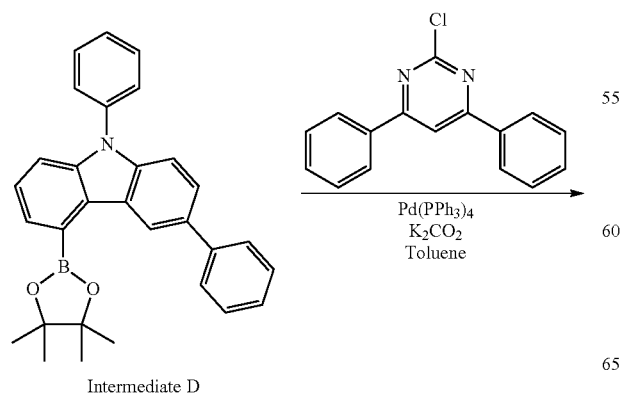

17.5 g (42 mmol) of Intermediate C, 20.0 g (46 mmol) of 2,4-diphenyl-6-(3-(4,4,5,5-tetramethyl-1,3,2-dioxaborolan-2-yl)phenyl)-1,3,5-triazine, 14 g (104 mmol) of K$_2$CO$_3$, and 2.4 g (2.1 mmol) of Pd(PPh$_3$)$_4$ were added to 80 mL of toluene and stirred at about 120° C. for about 48 hours. After completion of the reaction, water was added to the reaction product and stirred, followed by filtration to obtain a dark gray solid. This solid was dissolved in hot toluene, and then filtered. The resulting toluene solution was collected, and methanol was added thereto to obtain a precipitate. This precipitate was filtered to obtain a solid, which was then recrystallized with 1-chlorobenzene to obtain Compound 3 in white powder (18.0 g, Yield: 70%). Compound 3 was identified using 1H-NMR and LC/MS.

$^1$H NMR (CDCl$_3$, 300 MHz): 9.17 (s, 1H), 8.92 (d, 1H), 8.77 (dd, 4H), 7.95~7.68 (m, 7H), 7.66~7.40 (m, 14H), 7.27~7.19 (m, 3H).

LC/MS, calcd.: C$_{45}$H$_{30}$N$_4$=626.75. found: m/z=626.2 (M+, 100%)

Synthesis Example 4: Synthesis of Compound 18

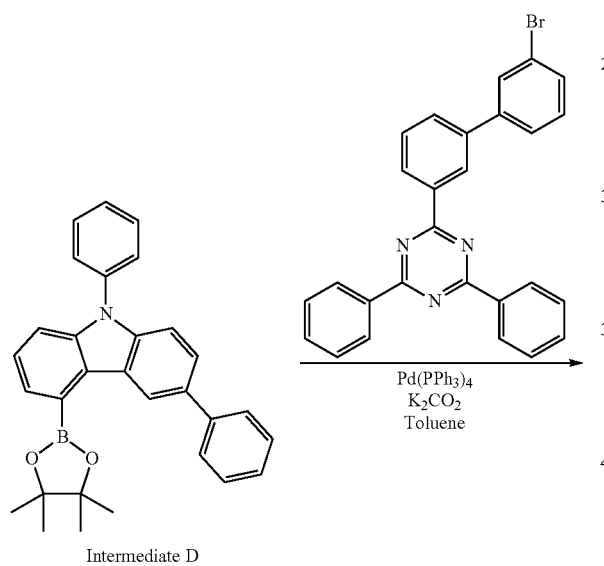

Intermediate D

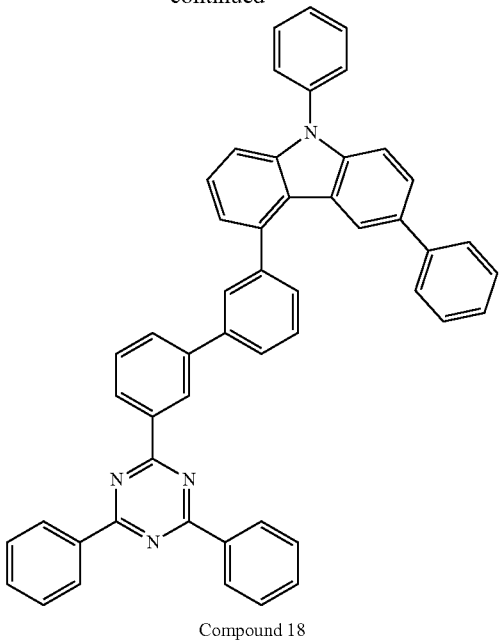

Compound 18

Compound 18 (white solid, Yield: 76%) was synthesized in the same manner as in the synthesis of Compound 1 of Synthesis Example 1, except that 2-(3'-bromo-[1,1'-biphenyl]-3-yl)-4,6-diphenyl-1,3,5-triazine, instead of 2-chloro-4,6-diphenyl-1,3,5-triazine, was used. Compound 18 was identified using LC/MS.

LC/MS, calcd.: C$_{51}$H$_{34}$N$_4$=702.84. found: m/z=702.2 (M+, 100%)

Synthesis Example 5: Synthesis of Compound 32

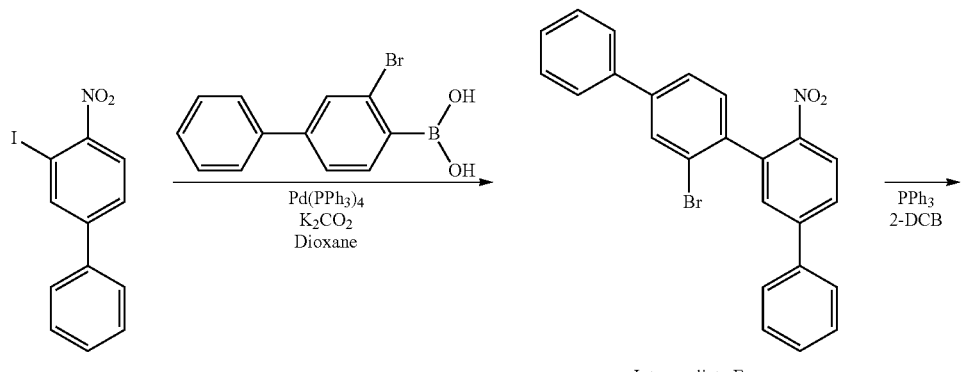

Intermediate E

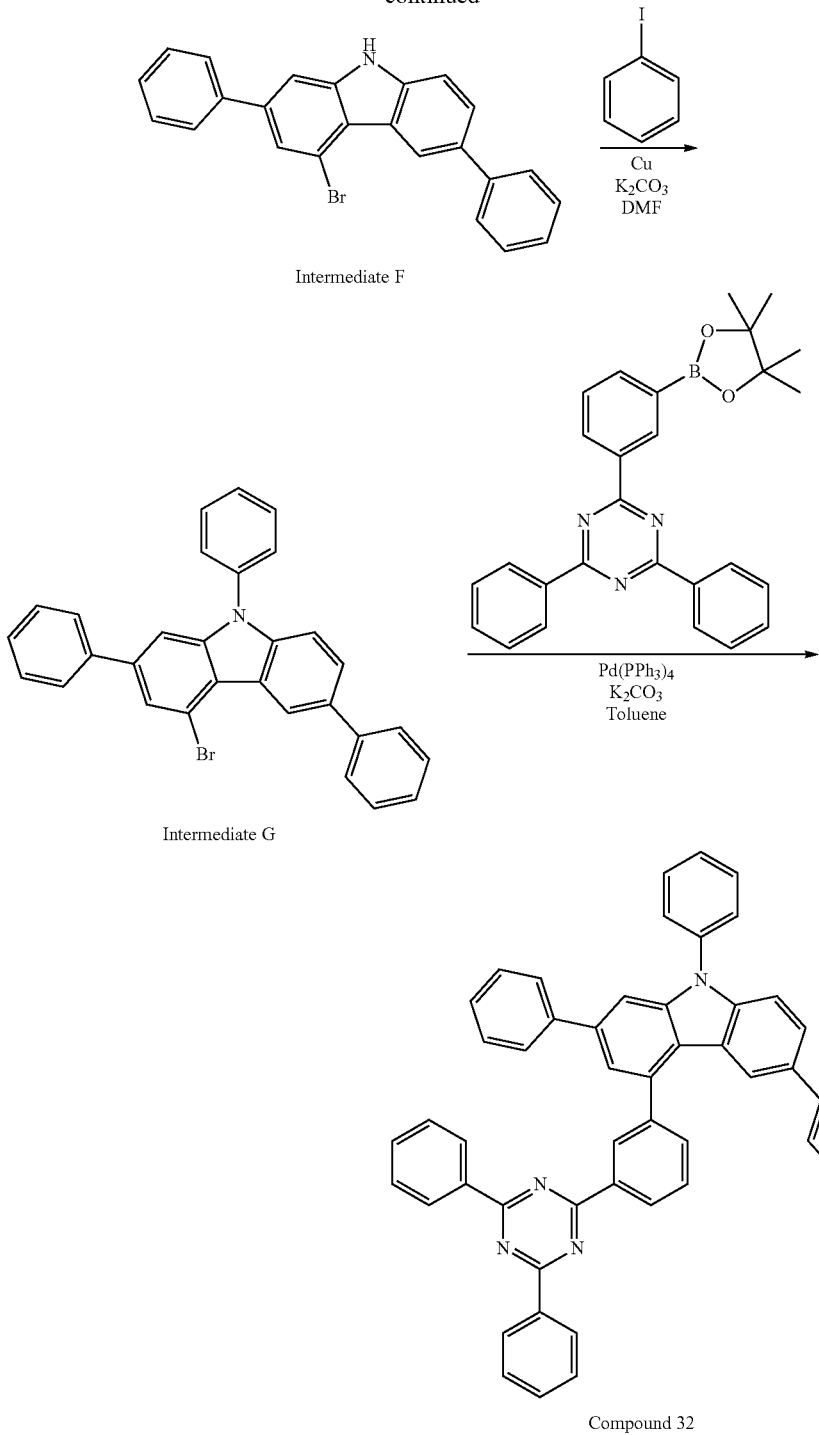

Compound 32

Synthesis of Intermediate E

Intermediate E (white solid, Yield: 66%) was synthesized in the same manner as in the synthesis of Intermediate A of Synthesis Example 1, except that 3-bromo-[1,1'-biphenyl]-4-yl)boronic acid, instead of (2-bromophenyl)boronic acid, was used. Intermediate E was identified using LC/MS.

LC/MS, calcd.: $C_{24}H_{16}BrNO_2$=430.29. found: m/z=429.04 (M+, 100%)

Synthesis of Intermediate F

Intermediate F (white solid, Yield: 57%) was synthesized in the same manner as in the synthesis of Intermediate B of Synthesis Example 1, except that Intermediate E, instead of Intermediate A, was used. Intermediate F was identified using LC/MS.

LC/MS, calcd.: $C_{24}H_{16}BrN$=398.29. found: m/z=397.05 (M+, 100%)

Synthesis of Intermediate G

Intermediate G (white solid, Yield: 61%) was synthesized in the same manner as in the synthesis of Intermediate C of Synthesis Example 1, except that Intermediate F, instead of Intermediate B, was used. Intermediate G was identified using LC/MS.

LC/MS, calcd.: $C_{30}H_{20}BrN$=474.39. found: m/z=475.08 (M+, 100%)

Synthesis of Compound 32

Compound 32 (white solid, Yield: 70%) was synthesized in the same manner as in the synthesis of Compound 3 of Synthesis Example 3, except that Intermediate G, instead of Intermediate C, was used. Compound 32 was identified using LC/MS.

LC/MS, calcd.: $C_{51}H_{34}N_4$=702.84. found: m/z=702.28 (M+, 100%)

Synthesis Example 6: Synthesis of Compound 36

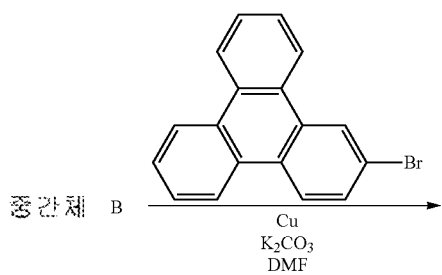

Synthesis of Intermediate H

Intermediate H (white solid, Yield: 50%) was synthesized in the same manner as in the synthesis of Intermediate C of Synthesis Example 1, except that 2-bromotriphenylene, instead of iodobenzene, was used. Intermediate H was identified using LC/MS.

LC/MS, calcd.: $C_{36}H_{22}BrN$=548.47. found: m/z=547.09 (M+, 100%)

Synthesis of Compound 36

Compound 36 (white solid, Yield: 52%) was synthesized in the same manner as in the synthesis of Compound 3 of Synthesis Example 3, except that Intermediate H, instead of Intermediate C, was used. Compound 36 was identified using LC/MS.

LC/MS, calcd.: $C_{57}H_{36}N_4$=776.92. found: m/z=776.29 (M+, 100%)

Synthesis Example 7: Synthesis of Compound 39
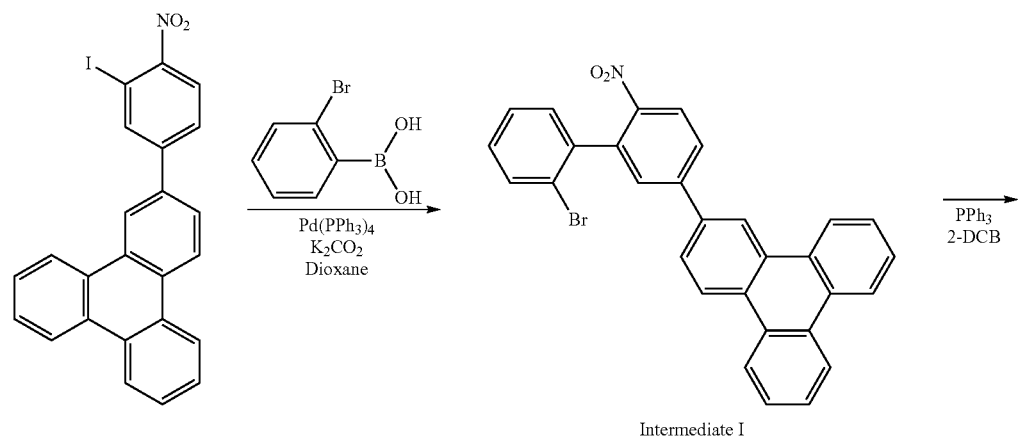
Intermediate I
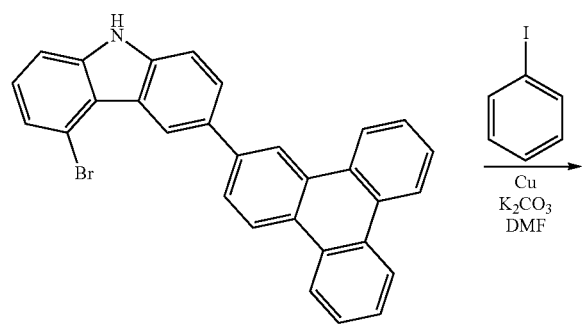
Intermediate J
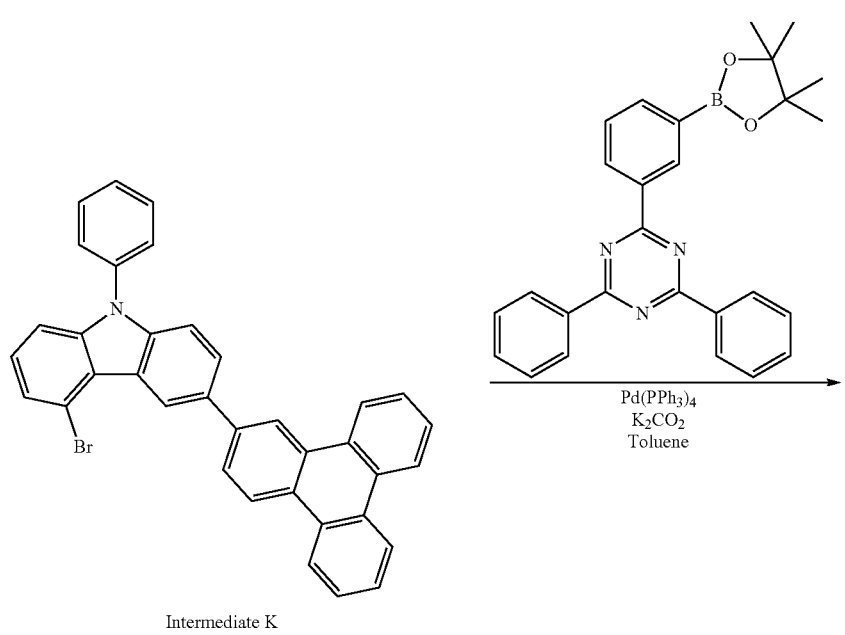
Intermediate K

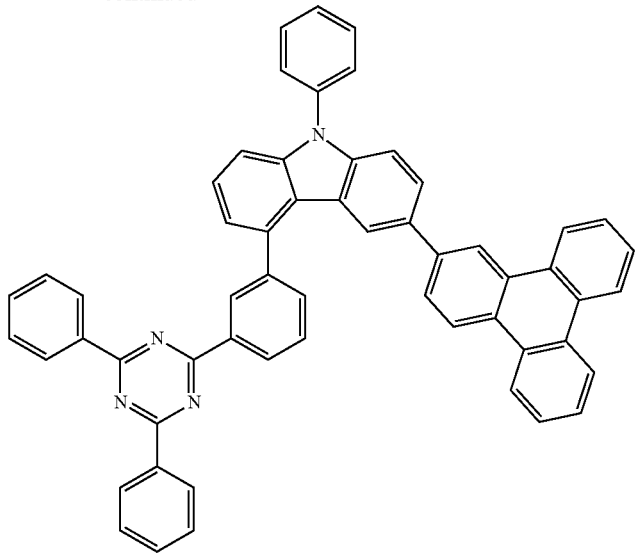

Compound 39

Synthesis of Intermediate I

Intermediate I (yellow solid, Yield: 54%) was synthesized in the same manner as in the synthesis of Intermediate A of Synthesis Example 1, except that 2-(3-iodo-4-nitrophenyl)triphenylene, instead of 3-iodo-4-nitro-1,1'-biphenyl, was used. Intermediate L was identified using LC/MS.

LC/MS, calcd.: $C_{30}H_{18}BrNO_2=504.37$. found: m/z=503.05 (M+, 100%)

Synthesis of Intermediate J

Intermediate J (white solid, Yield: 48%) was synthesized in the same manner as in the synthesis of Intermediate B of Synthesis Example 1, except that Intermediate I, instead of Intermediate A, was used. Intermediate J was identified using LC/MS.

LC/MS, calcd.: $C_{30}H_{18}BrN=472.37$. found: m/z=471.06 (M+, 100%)

Synthesis of Intermediate K

Intermediate K (white solid, Yield: 45%) was synthesized in the same manner as in the synthesis of Intermediate C of Synthesis Example 1, except that Intermediate J, instead of Intermediate B, was used. Intermediate K was identified using LC/MS.

LC/MS, calcd.: $C_{36}H_{22}BrN=548.47$. found: m/z=547.09 (M+, 100%)

Synthesis of Compound 39

Compound 39 (white solid, Yield: 63%) was synthesized in the same manner as in the synthesis of Compound 3 of Synthesis Example 3, except that Intermediate K, instead of Intermediate C, was used. Compound 39 was identified using LC/MS.

LC/MS, calcd.: $C_{57}H_{36}N_4=779.92$. found: m/z=776.29 (M+, 100%)

Synthesis Example 8: Synthesis of Compound 96

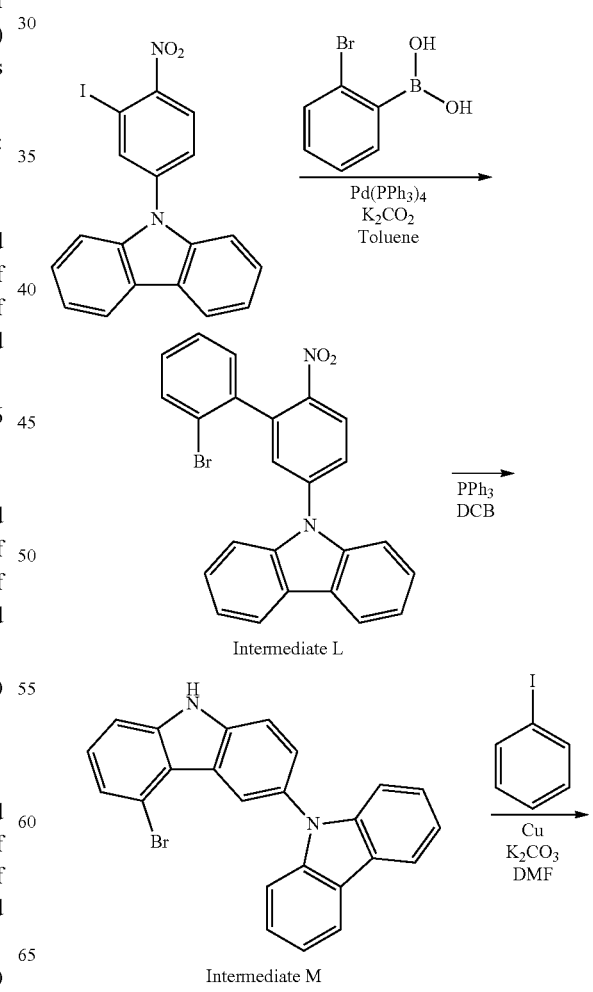

Intermediate L

Intermediate M

-continued

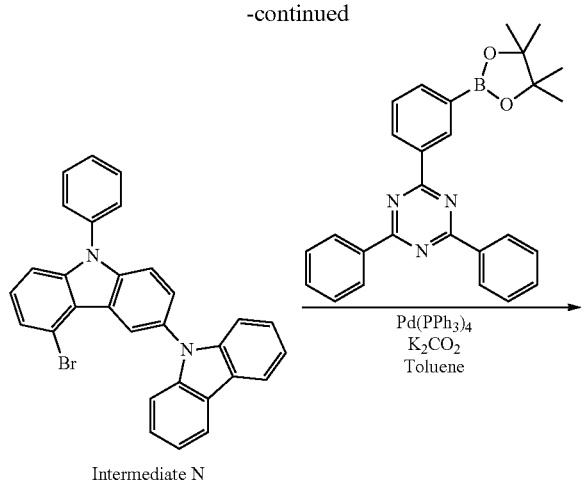

Intermediate N

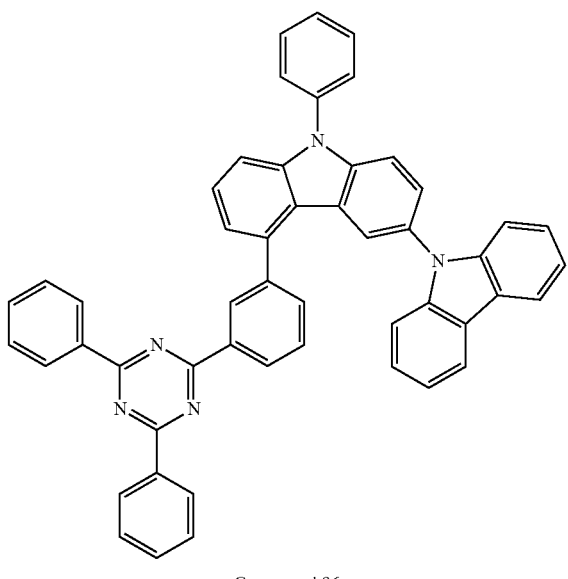

Compound 96

Synthesis of Intermediate L

Intermediate L (white solid, Yield: 60%) was synthesized in the same manner as in the synthesis of Intermediate A of Synthesis Example 1, except that 9-(3-iodo-4-nitrophenyl)-9H-carbazole, instead of 3-iodo-4-nitro-1,1'-biphenyl, was used. Intermediate L was identified using LC/MS.

LC/MS, calcd.: $C_{24}H_{15}N_2O_2$=443.29. found: m/z=442.0 (M+, 100%).

Synthesis of Intermediate M

Intermediate M (white solid, Yield: 55%) was synthesized in the same manner as in the synthesis of Intermediate B of Synthesis Example 1, except that Intermediate L, instead of Intermediate A, was used. Intermediate M was identified using LC/MS.LC/MS, calcd.: $C_{24}H_{15}BrN_2$=411.29. found: m/z=410.0 (M+, 100%)

Synthesis of Intermediate N

Intermediate N (white solid, Yield: 62%) was synthesized in the same manner as in the synthesis of Intermediate C of Synthesis Example 1, except that Intermediate M, instead of Intermediate B, was used. Intermediate N was identified using LC/MS.

LC/MS, calcd.: $C_{30}H_{19}BrN_2$=487.39. found: m/z=486.0 (M+, 100%)

Synthesis of Compound 96

Compound 96 (white solid, Yield: 68%) was synthesized in the same manner as in the synthesis of Compound 3 of Synthesis Example 3 via recrystallization with n-methyl-2-pyrrolidone (NMP), except that Intermediate N, instead of Intermediate C, was used. Compound 96 was identified using LC/MS.

LC/MS, calcd.: $C_{51}H_{33}N_5$=715.84. found: m/z=715.2 (M+, 100%)

Evaluation Example 1: Evaluation of HOMO, LUMO, and Triplet ($T_1$) Energy Levels and Energy Band Gap The highest occupied molecular orbital (HOMO), lowest unoccupied molecular orbital (LUMO), and triplet ($T_1$) energy levels of Compounds 1, 2, 3, 18, 32, 36, 39, 96, and C were evaluated according to the methods described in Table 1 below. The results are shown in Table 2.

TABLE 1

| | |
|---|---|
| HOMO energy level evaluation method | HOMO energy levels of the compounds were evaluated using a density functional theory (DFT) method (B3LYP/6-31G(D,P)//B3LYP/6-31G(D,P) w/Gaussian09) |
| LUMO energy level evaluation method | LUMO energy levels of the compounds were evaluated using a DFT method (B3LYP/6-31G(D,P)//B3LYP/6-31G(D,P) w/Gaussian09) |
| T1 energy level evaluation method | T1 energy levels of the compounds were evaluated using a time dependent density functional theory (TDDFT) method (B3LYP/6-31G(D,P)//B3LYP/6-31G(D,P) w/Gaussian09) |

TABLE 2

| Compound No. | HOMO (eV) (Absolute value) | LUMO (eV) (Absolute value) | T1 energy level (eV) | Energy band gap (eV) |
|---|---|---|---|---|
| Compound 1 | 5.234 | 1.790 | 2.612 | 3.453 |
| Compound 2 | 5.108 | 1.619 | 2.710 | 3.489 |
| Compound 3 | 5.195 | 1.820 | 2.877 | 3.375 |
| Compound 18 | 5.220 | 1.813 | 2.958 | 3.375 |
| Compound 32 | 5.215 | 1.826 | 2.808 | 3.389 |
| Compound 36 | 5.179 | 1.821 | 2.792 | 3.358 |
| Compound 39 | 5.164 | 1.848 | 2.749 | 3.316 |
| Compound 96 | 5.054 | 1.809 | 2.799 | 3.245 |
| Compound C | 5.384 | 1.925 | 2.666 | 3.459 |

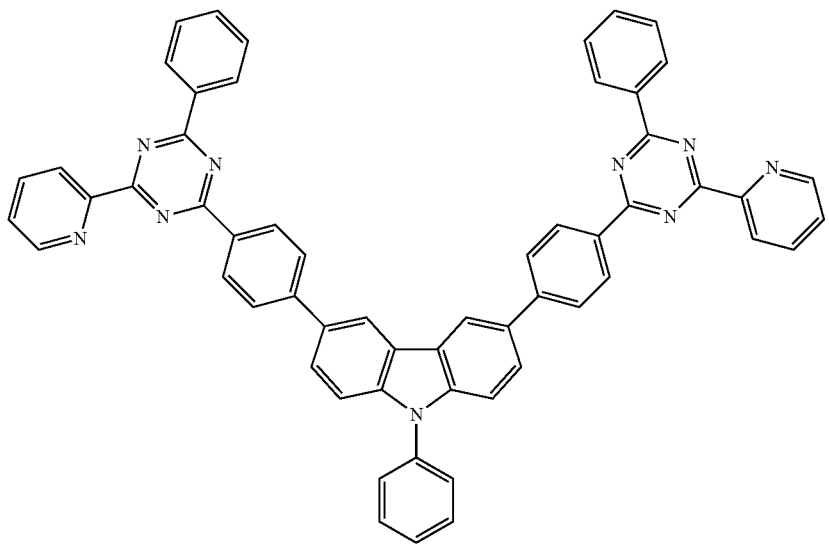

Compound C

Referring to Table 1, Compound 1, 2, 3, 18, 32, 36, 39, and 96 were found to have high T1 energy levels and wide band gaps, and thus have electrically characteristics suitable for use as materials for organic light-emitting devices.

The absolute values of the HOMO and LUMO energy levels of Compound 1, 2, 3, 18, 32, 36, 39, and 96 are smaller than those of Compound C, indicating that Compound 1, 2, 3, 18, 32, 36, 39, and 96 have electrical characteristics suitable for use as materials of organic light-emitting devices.

Example 1

To manufacture an anode, a glass substrate with deposited ITO/Ag/ITO layers (70 Å/1,000 Å/70 Å) was cut to a size of 50 mm×50 mm×0.5 mm and then ultrasonicated in isopropyl alcohol and pure water each for five minutes, and then cleaned by irradiation of ultraviolet rays for 30 minutes and exposure to ozone. The resulting glass substrate was loaded into a vacuum deposition device.

2-TNATA was deposited on the anode to form an HIL having a thickness of 60 nm, and then NPB was deposited on the HIL to form a HTL having a thickness of 100 nm.

Compound 1 (host) and Ir(ppy)$_3$ (dopant) were co-deposited in a weight ratio of about 91:9 on the HTL to form an EML having a thickness of about 25 nm, followed by depositing BCP on the EML to form a HBL having a thickness of about 5 nm. After deposition of Alq$_3$ on the HBL to form an ETL having a thickness of about 35 nm, LiF was deposited on the ETL to form an EIL having a thickness of about 1 nm, followed by co-depositing Mg and Ag in a weight ratio of 9:1 on the EIL to form a cathode having a thickness of about 12 nm, thereby completing the manufacture of the organic light-emitting device (emitting green light).

Example 2

An organic light-emitting device was manufactured in the same manner as in Example 1, except that Compound 2, instead of Compound 1, was used as a host to form the EML.

Example 3

An organic light-emitting device was manufactured in the same manner as in Example 1, except that Compound 3, instead of Compound 1, was used as a host to form the EML.

Example 4

An organic light-emitting device was manufactured in the same manner as in Example 1, except that Compound 18, instead of Compound 1, was used as a host to form the EML.

Example 5

An organic light-emitting device was manufactured in the same manner as in Example 1, except that Compound 32, instead of Compound 1, was used as a host to form the EML.

Example 6

An organic light-emitting device was manufactured in the same manner as in Example 1, except that Compound 36, instead of Compound 1, was used as a host to form the EML.

Example 7

An organic light-emitting device was manufactured in the same manner as in Example 1, except that Compound 39, instead of Compound 1, was used as a host to form the EML.

Example 8

An organic light-emitting device was manufactured in the same manner as in Example 1, except that Compound 96, instead of Compound 1, was used as a host to form the EML.

Comparative Example A

An organic light-emitting device was manufactured in the same manner as in Example 1, except that Compound A, instead of Compound 1, was used as a host to form the EML.

Compound A

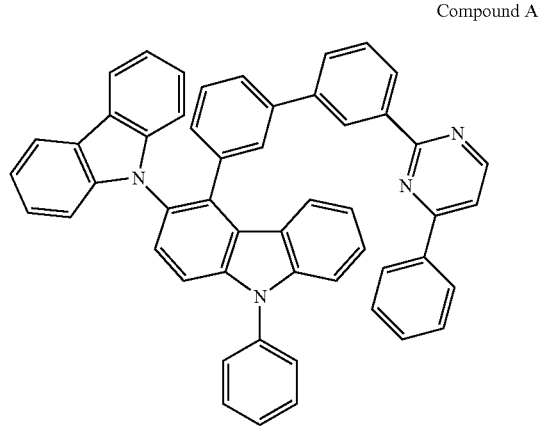 [SMILES: c1ccc(-c2ccnc(-c3cccc(-c4cccc(-c5c(-n6c7ccccc7c7ccccc76)ccc6c5c5ccccc5n6-c5ccccc5)c4)c3)n2)cc1]

Comparative Example B

An organic light-emitting device was manufactured in the same manner as in Example 1, except that Compound B, instead of Compound 1, was used as a host to form the EML.

Compound B

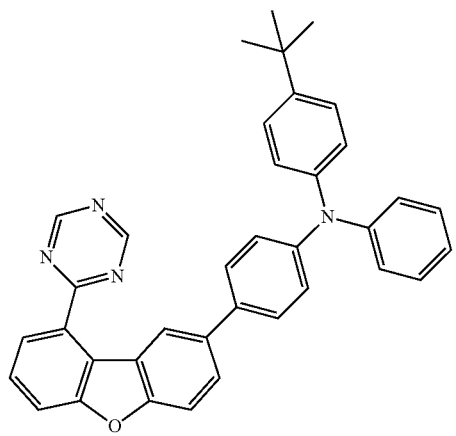

Comparative Example C

An organic light-emitting device was manufactured in the same manner as in Example 1, except that Compound C, instead of Compound 1, was used as a host to form the EML.

Compound C

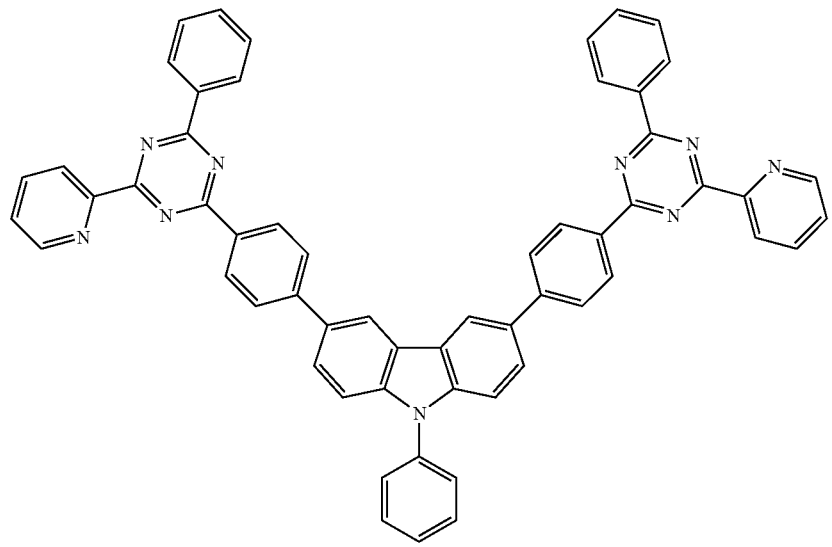

Evaluation Example 3: Characteristics Evaluation of Organic Light-Emitting Devices Current density changes with respect to voltage, luminance changes, and emission efficiencies in the organic light-emitting devices of Examples 1 to 8 and Comparative Examples A, B, and C were measured according to the following methods. The results are shown in Table 3 below.

1) Color coordinates were measured using a PR650 (Spectroscan) Source Measurement Unit (available from Photo Research, Inc.) with a supply of power using a Kethley Source-Measure Unit (SMU 236).

2) Luminances were measured using a PR650 (Spectroscan) Source Measurement Unit (available from Photo Research, Inc.) with a supply of power using a Kethley Source-Measure Unit (SMU 236).

3) Efficiencies were measured using a PR650 (Spectroscan) Source Measurement Unit (available from Photo Research, Inc.) with a supply of power using a Kethley Source-Measure Unit (SMU 236).

4) Lifetime (LT97) was measured as the time taken until an initial luminance (assumed as 100%) measured at a current density of about 10 milliamperes per square centimeter (mA/cm$^2$) is reduced to 97%.

TABLE 3

| Example | Host | Driving voltage (V) | Efficiency (cd/A) | Luminance (cd/m$^2$) | L97 (hr) | Color coordinates CIE x | CIE y |
|---|---|---|---|---|---|---|---|
| Example 1 | Compound 1 | 3.7 | 91 | 9000 | 120 | 0.25 | 0.71 |
| Example 2 | Compound 2 | 3.8 | 90 | 9000 | 130 | 0.24 | 0.71 |
| Example 3 | Compound 3 | 3.6 | 115 | 9000 | 359 | 0.25 | 0.71 |
| Example 4 | Compound 18 | 3.6 | 109 | 9000 | 245 | 0.25 | 0.71 |
| Example 6 | Compound 32 | 3.6 | 110 | 9000 | 105 | 0.26 | 0.71 |
| Example 7 | Compound 36 | 3.5 | 105 | 9000 | 280 | 0.25 | 0.70 |
| Example 8 | Compound 39 | 3.7 | 102 | 9000 | 210 | 0.26 | 0.70 |
| Example 10 | Compound 96 | 3.8 | 120 | 9000 | 365 | 0.24 | 0.71 |
| Comparative Example A | Compound A | 3.8 | 80 | 9000 | 75 | 0.26 | 0.70 |
| Comparative Example B | Compound B | 4.1 | 65 | 9000 | 12 | 0.29 | 0.71 |
| Comparative Example C | Compound C | 3.9 | 76 | 9000 | 50 | 0.25 | 0.71 |

Referring to Table 3, the organic light-emitting devices of Examples 1 to 8 were found to have improved emission efficiencies, compared to those of the organic light-emitting devices of Comparative Examples A to C. As described above, according to the one or more of the above embodiments of the present disclosure, a carbazole-based compound of Formula 1A or 1B may have good electrical characteristics and good thermal stability. An organic light-emitting device including the carbazole-based compound of Formula 1A or 1B may have a low driving voltage, a high efficiency, a high luminance, and long lifetime characteristics.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present disclosure have been described with reference to the figures, it will be understood by those of ordinary skill in the art that various changes in form and details may be made therein without departing from the spirit and scope of the present disclosure as defined by the following claims.

What is claimed is:

1. A carbazole-based compound represented by Formula 1A:

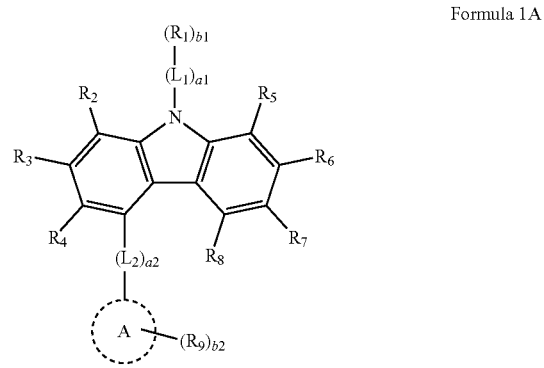

Formula 1A wherein a1 is 0;

$R_1$ is selected from Formulae 5-1 to 5-40;

b1 is 1;

$R_2$ to $R_6$ and $R_8$ are a hydrogen;

$R_7$ is selected from Formulae 5-1 to 5-40; a2 is 0 or 1;

$L_2$ is selected from Formulae 4-1 to 4-15;

ring A is represented Formula 2-1, wherein, in Formula 2-1, $R_{9a}$ and $R_{9b}$ are each independently, selected from Formulae 5-1 to 5-40:

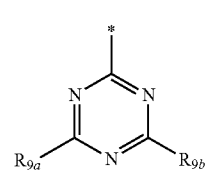

Formula 2-1

-continued
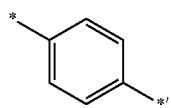
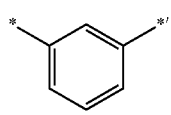
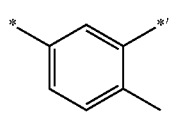
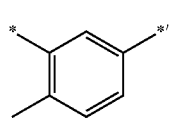
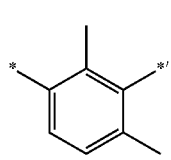
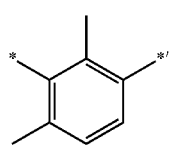
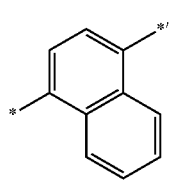
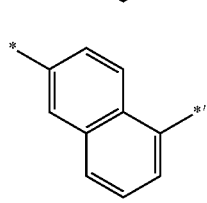
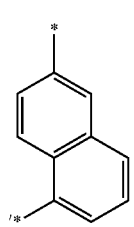
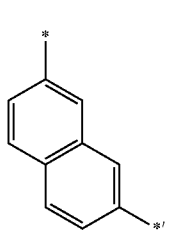
-continued
Formula 4-1
Formula 4-2
Formula 4-3
Formula 4-4
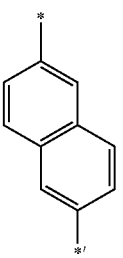
Formula 4-5
Formula 4-6
Formula 4-7
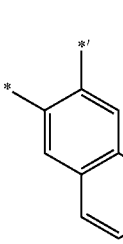
Formula 4-8
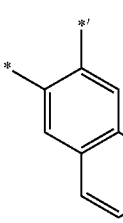
Formula 4-9
Formula 4-10
Formula 4-11
Formula 4-12
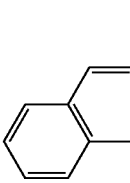
Formula 4-13
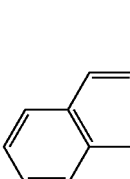
Formula 4-14
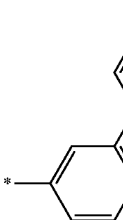
Formula 4-15
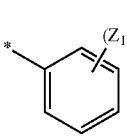
Formula 5-1
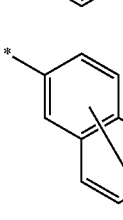
Formula 5-2
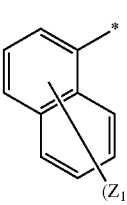
Formula 5-3

-continued
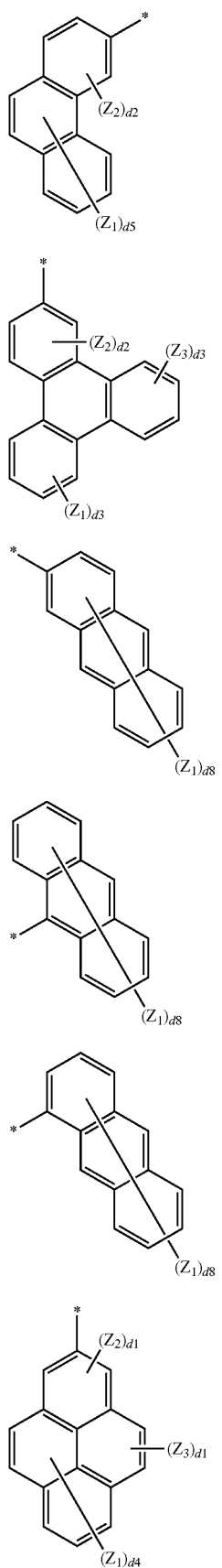
-continued
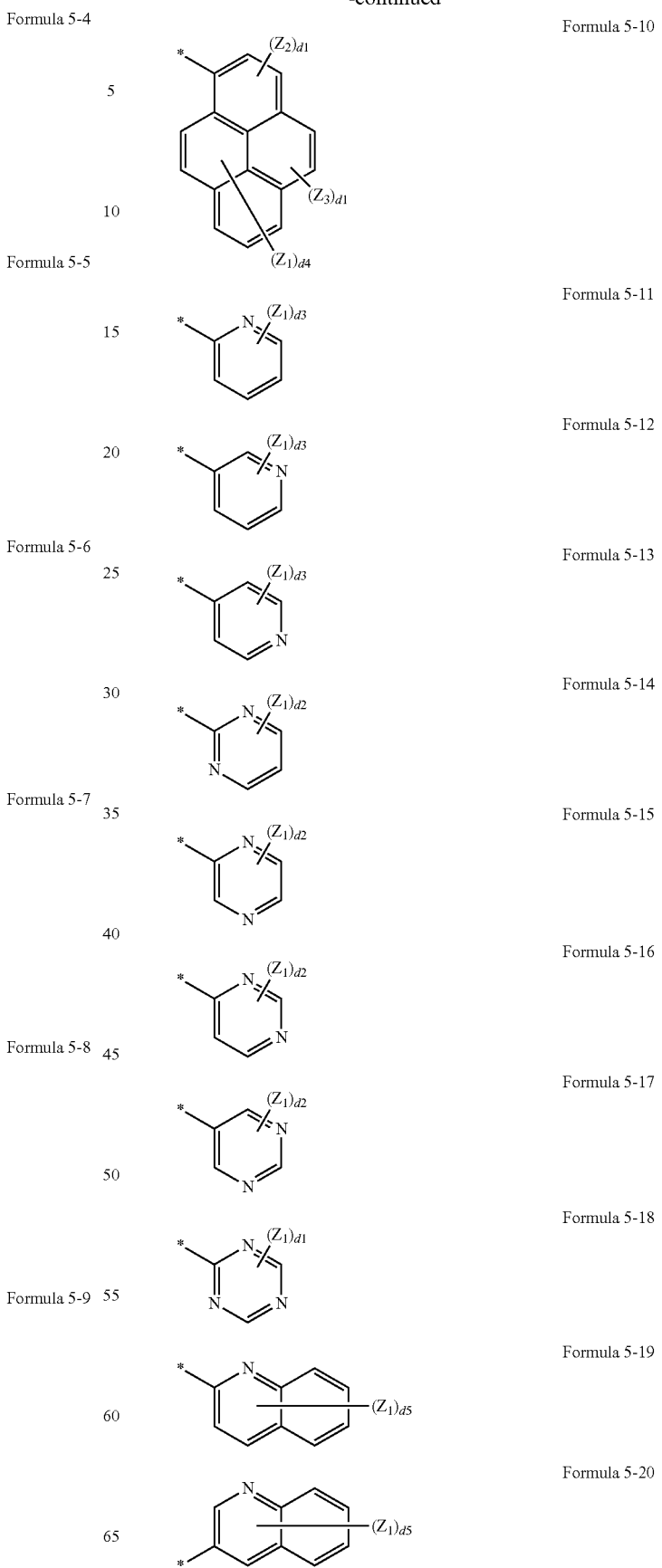

-continued
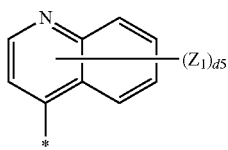
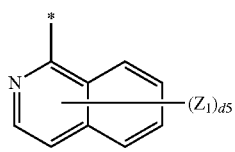
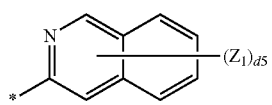
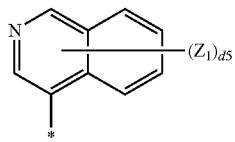
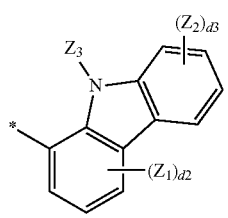
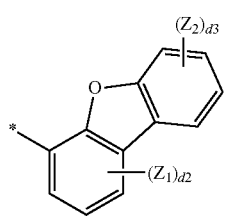
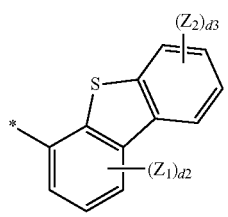
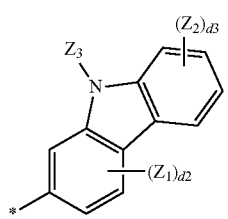
-continued
Formula 5-21
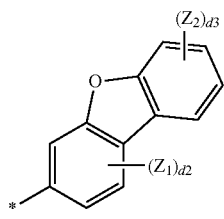
Formula 5-22
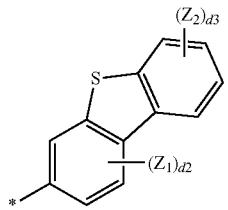
Formula 5-23
Formula 5-24
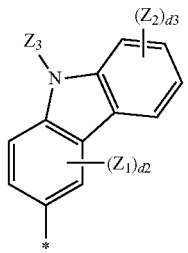
Formula 5-25
Formula 5-26
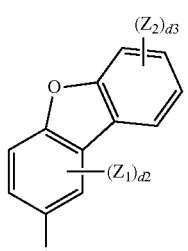
Formula 5-27
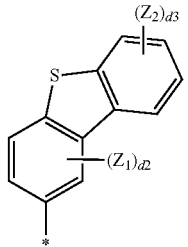
Formula 5-28
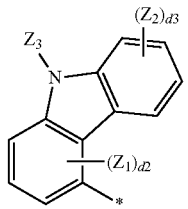
Formula 5-29
Formula 5-30
Formula 5-31
Formula 5-32
Formula 5-33
Formula 5-34
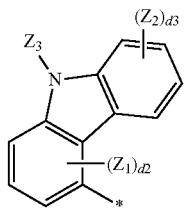
Formula 5-35
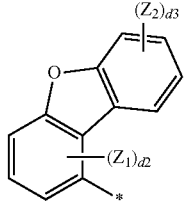

Formula 5-36

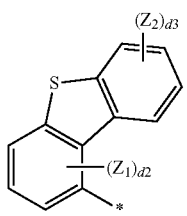

Formula 5-37

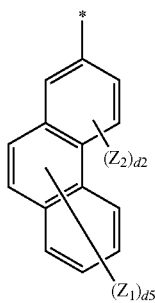

Formula 5-38

Formula 5-39

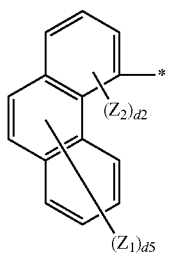

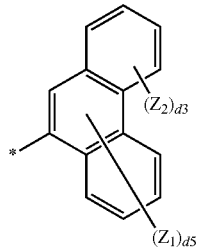

Formula 5-40 wherein, in Formulae 5-1 to 5-40, $Z_1$ to $Z_3$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group;

d1 is 1 or 2;
d2 is an integer selected from 1 to 3;
d3 is an integer selected from 1 to 4;
d4 is an integer selected from 1 to 5;
d5 is an integer selected from 1 to 6;
d6 is an integer selected from 1 to 7;
d7 is an integer selected from 1 to 8;
d8 is an integer selected from 1 to 9; and
* and *' each indicates a binding site to an adjacent atom.

2. A carbazole-based compound is selected from Compounds 1 to 130:

1

2

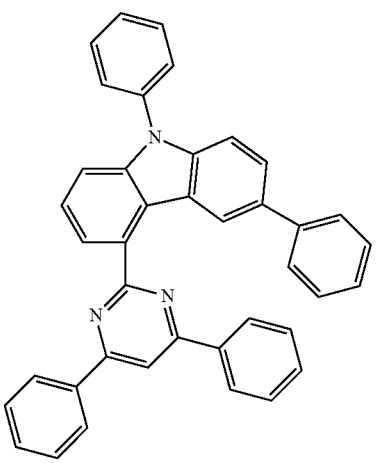

-continued
3
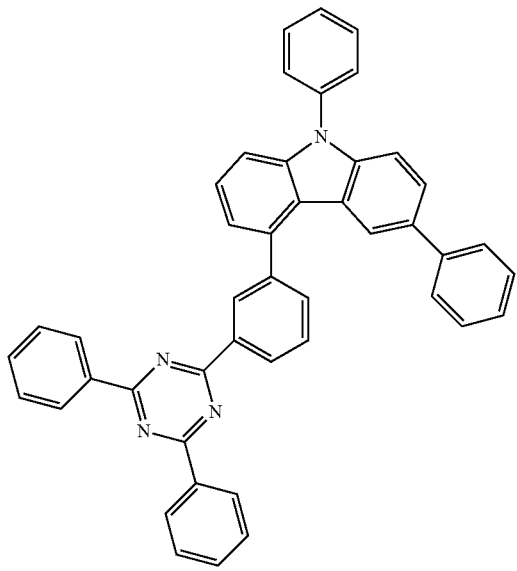
4
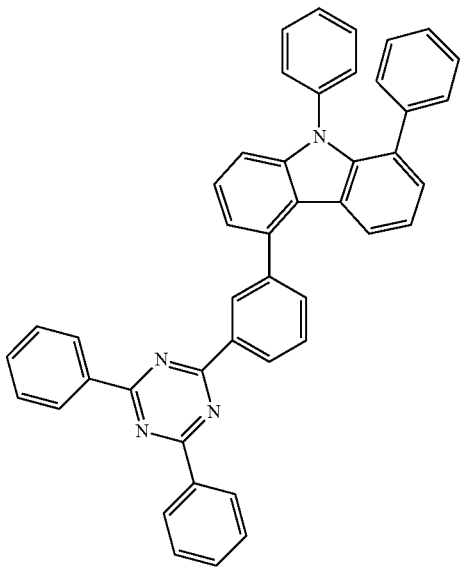
5
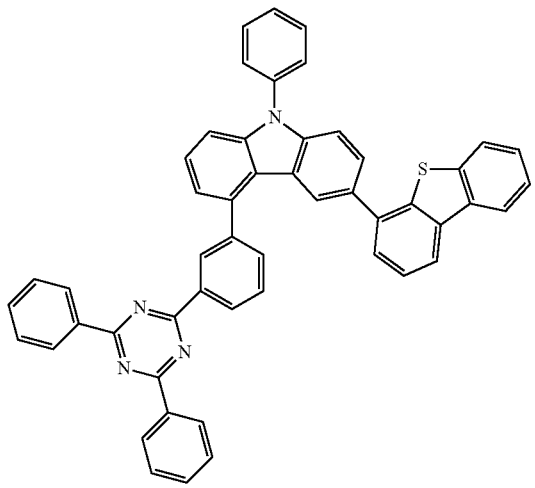
6
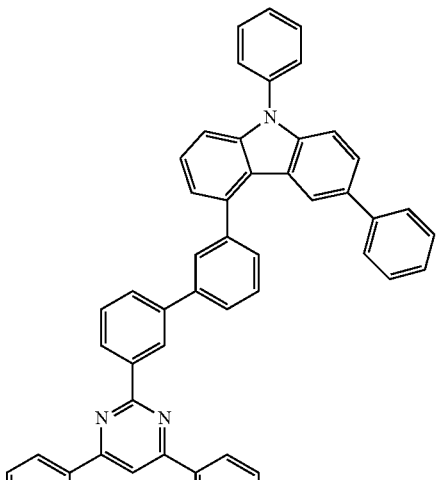
7
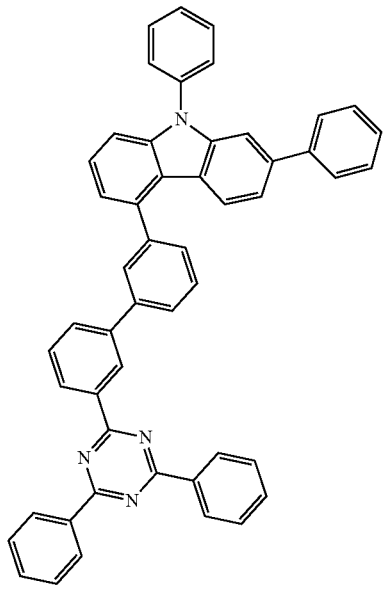
8
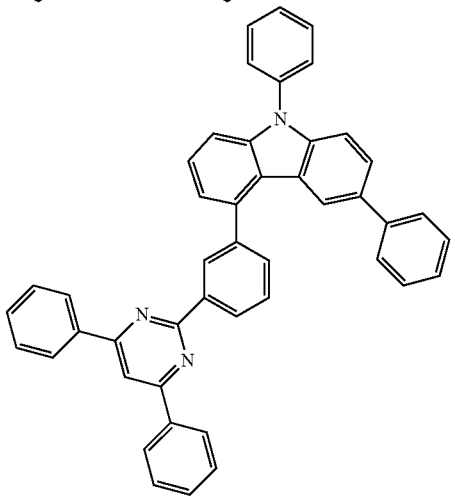

-continued
9
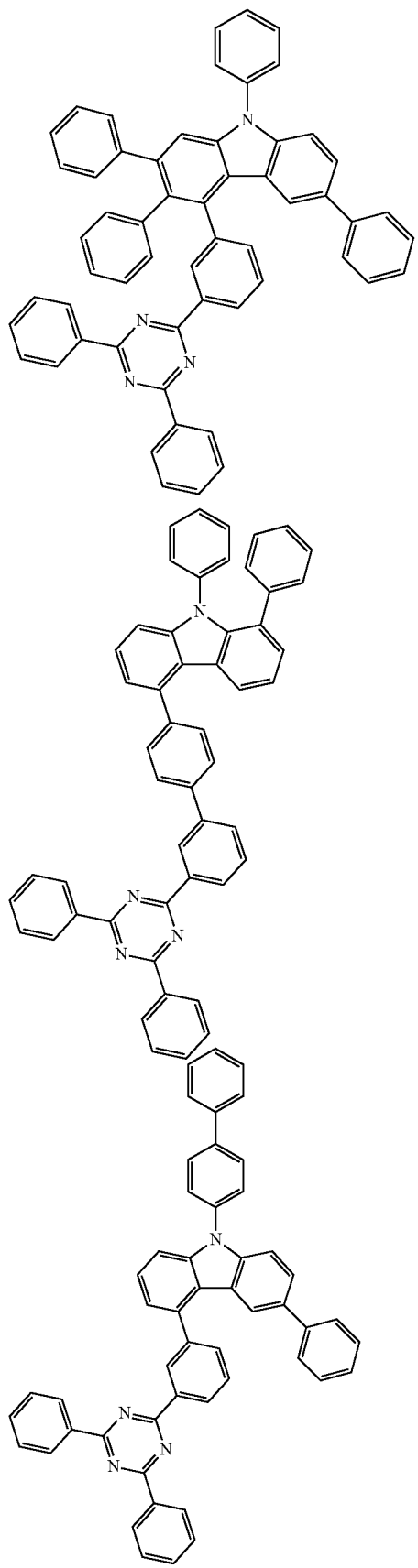
10
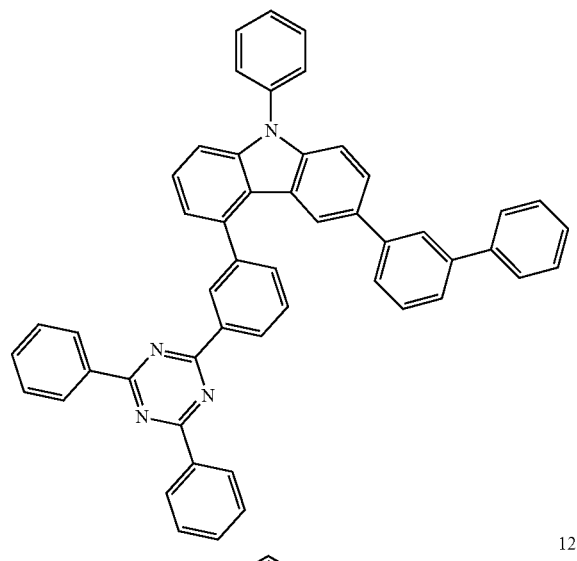
11
12
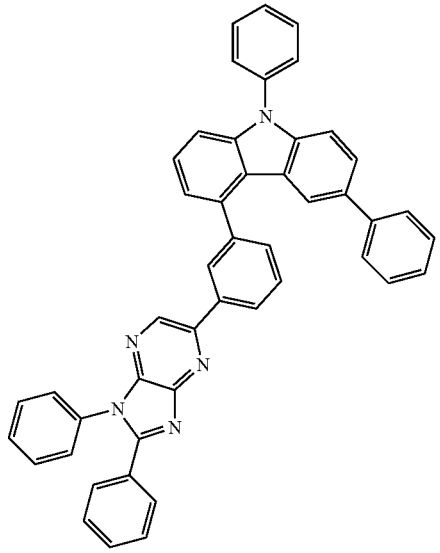
13
14
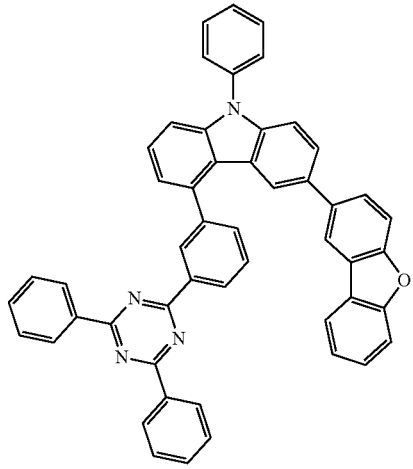

15
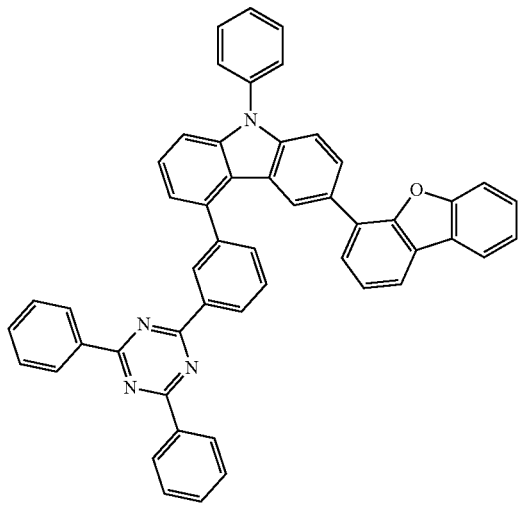
16
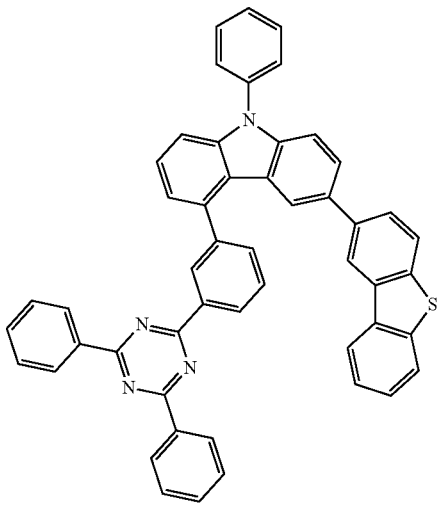
17
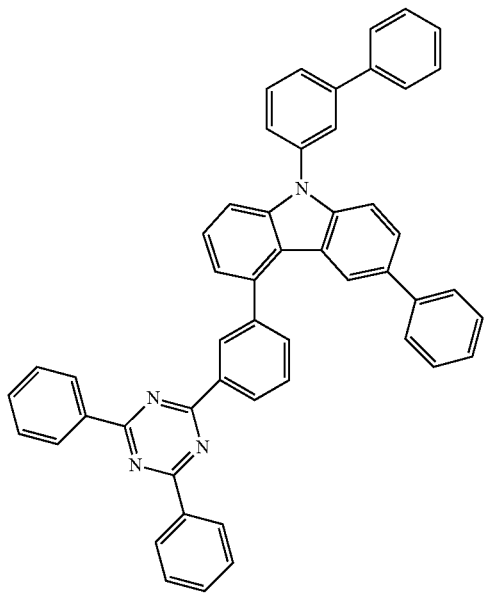
18
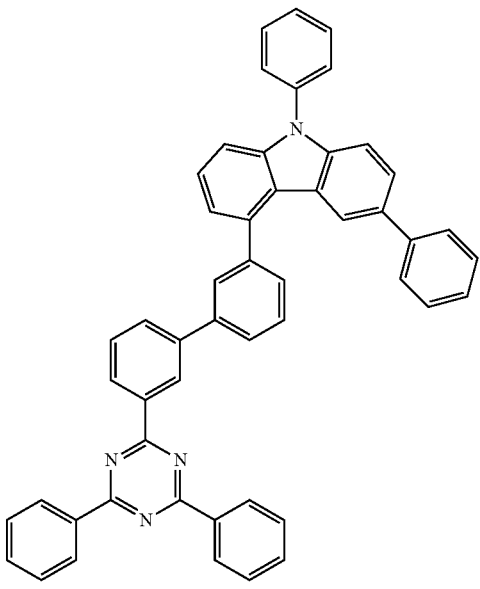
19
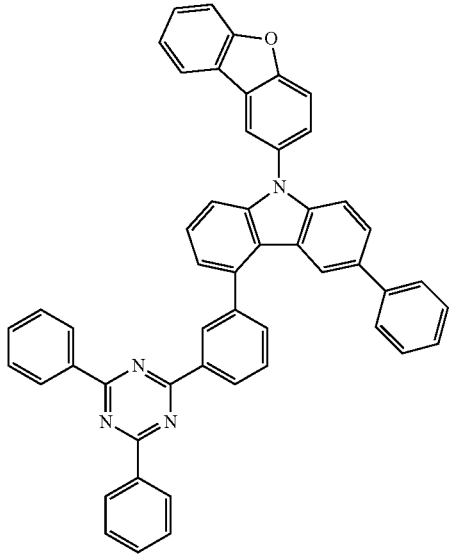
20
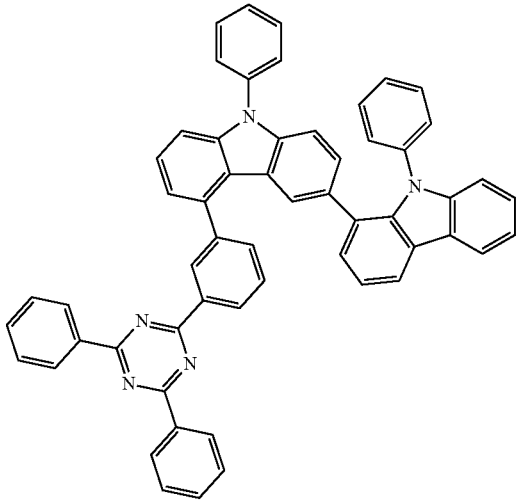

-continued
21
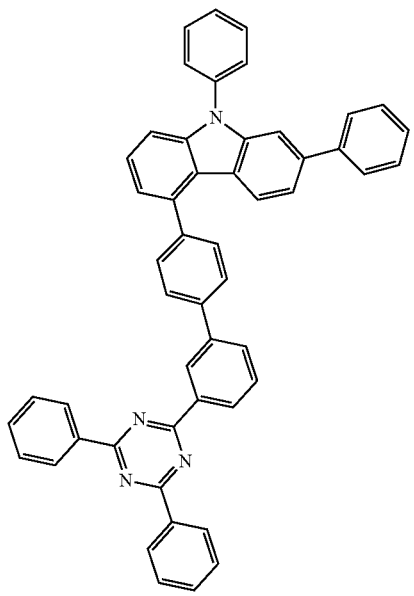
22
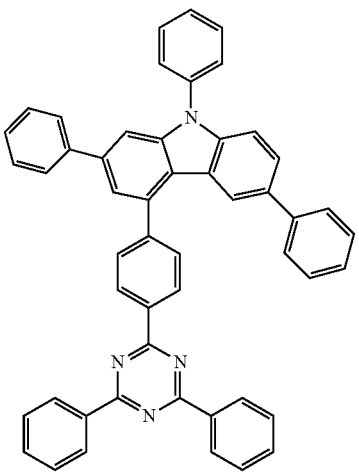
23
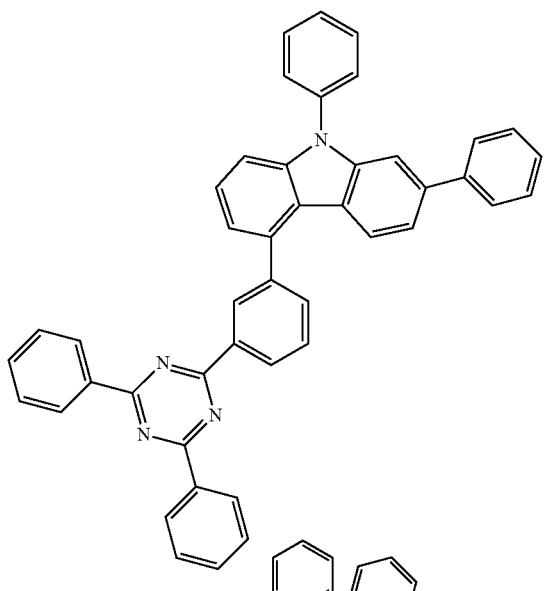
24
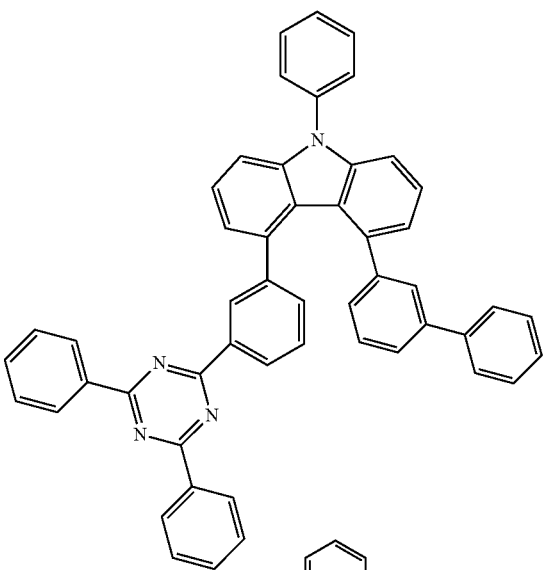
25
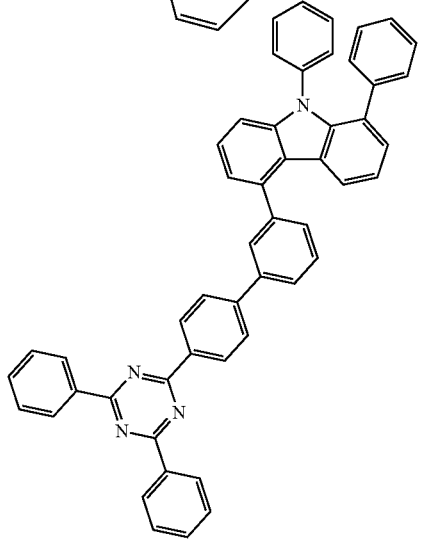
26
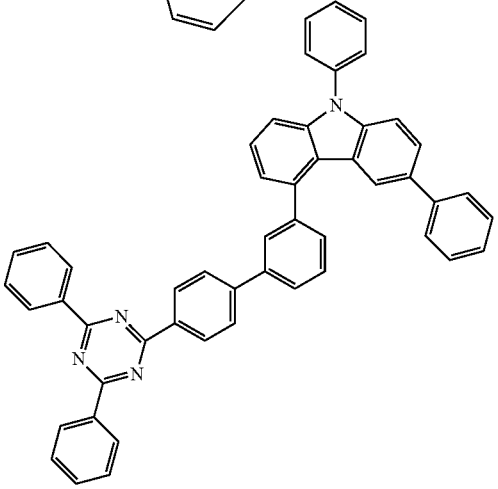

-continued
27
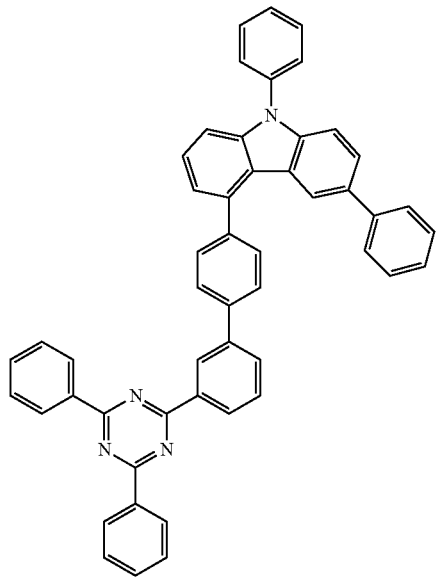
28
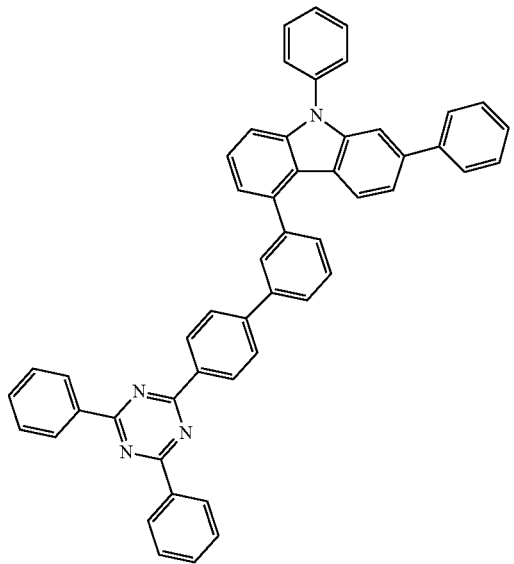
29
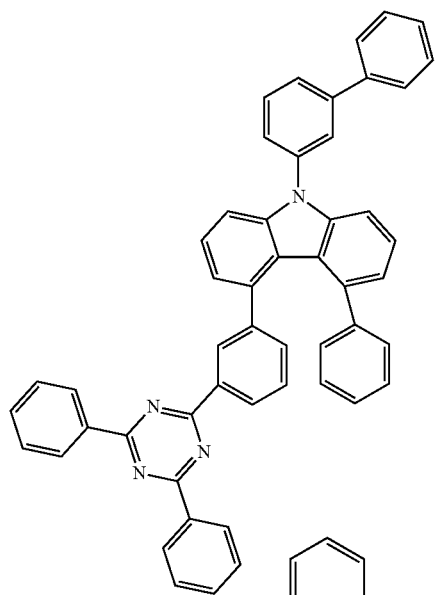
30
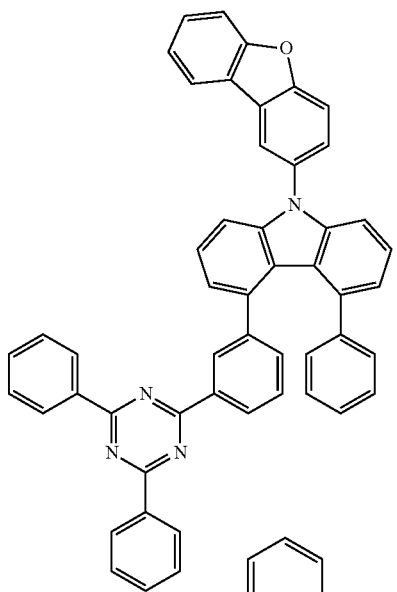
31
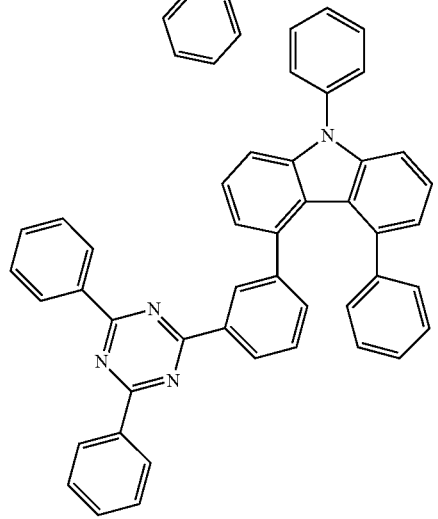
32
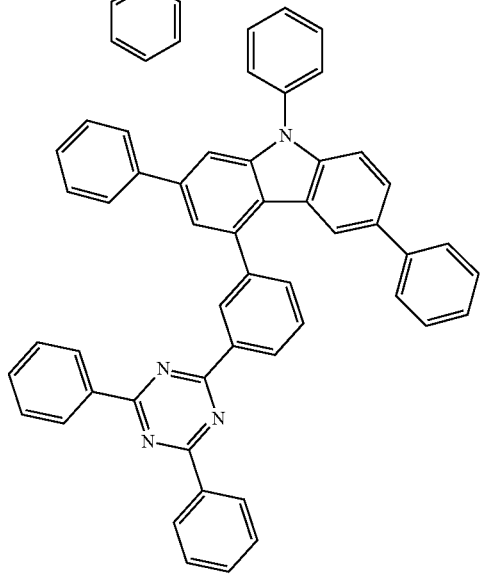

-continued
33
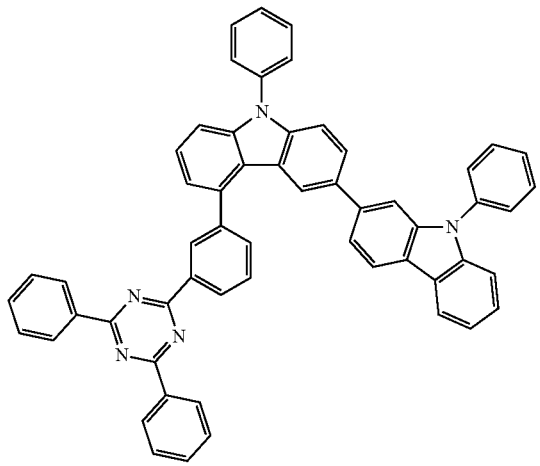
34
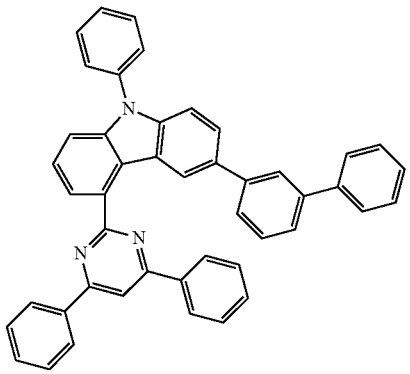
35
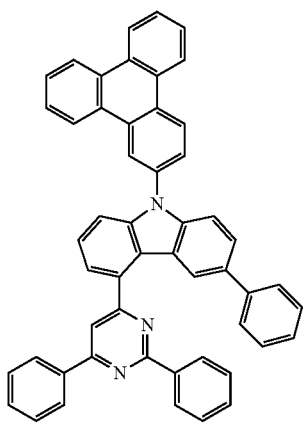
36
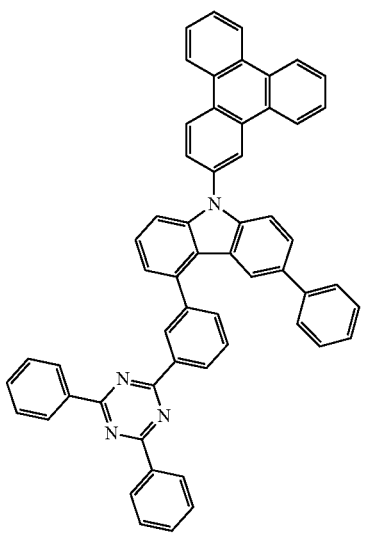
37
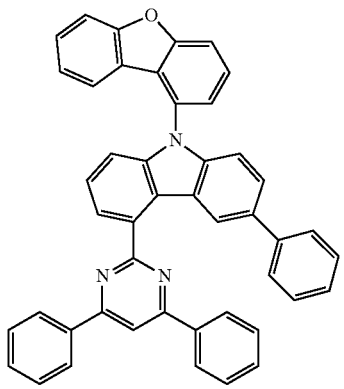
38
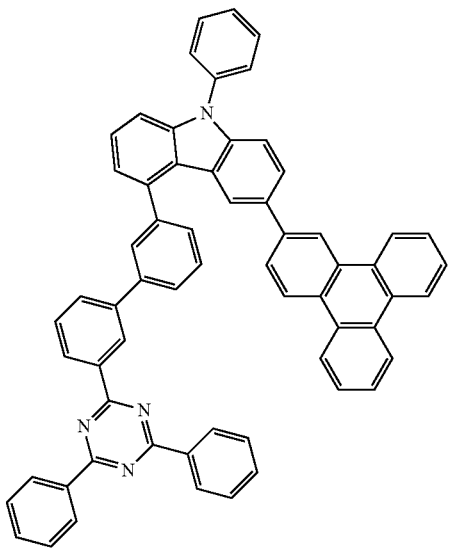

-continued
39
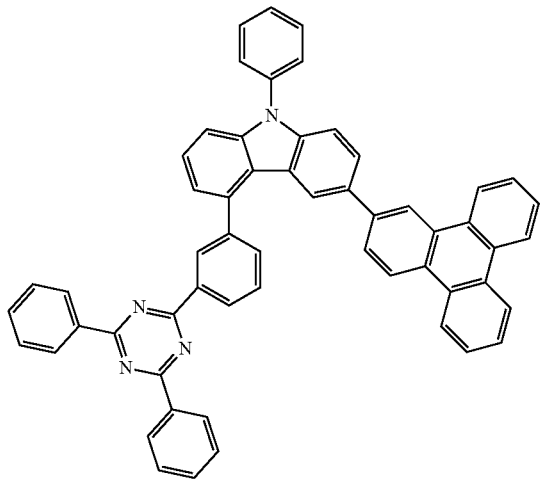
40
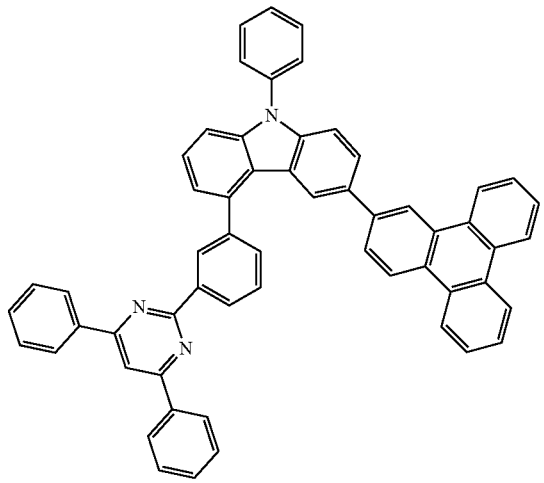
41
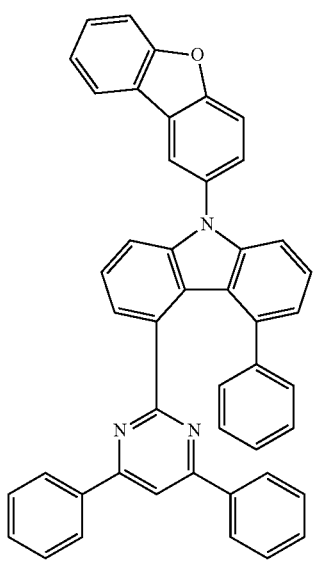
42
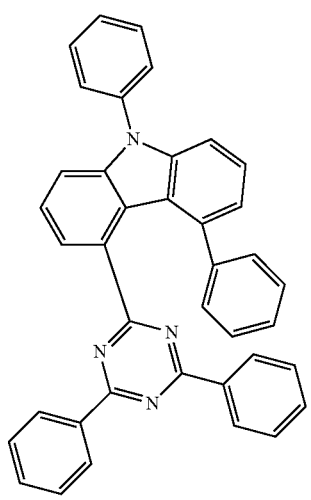
43
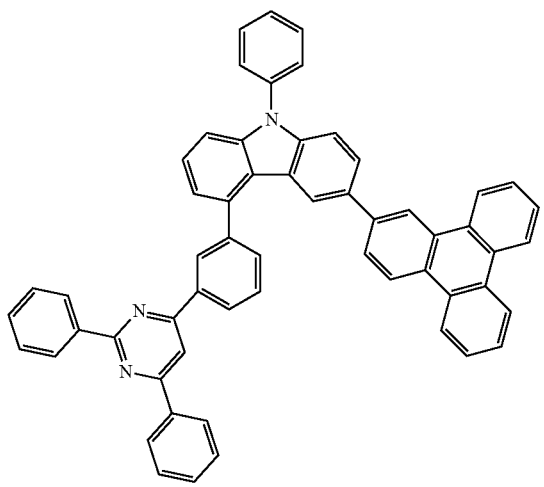
44
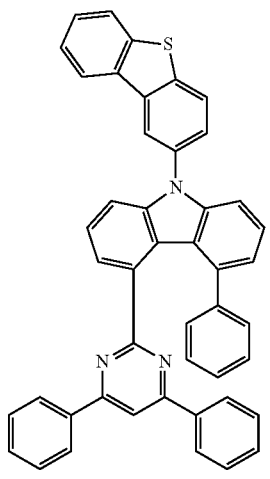

-continued
45
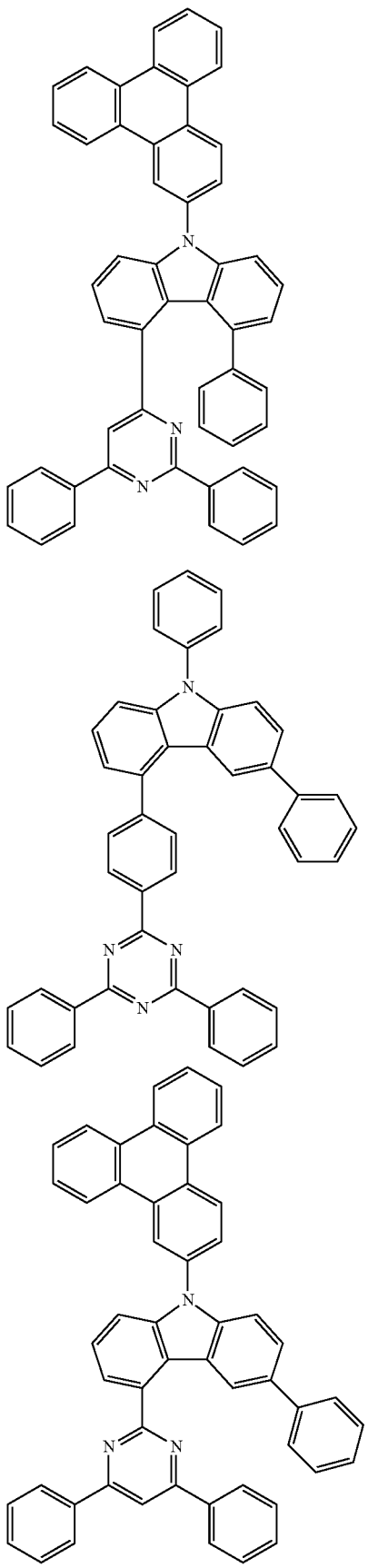
46
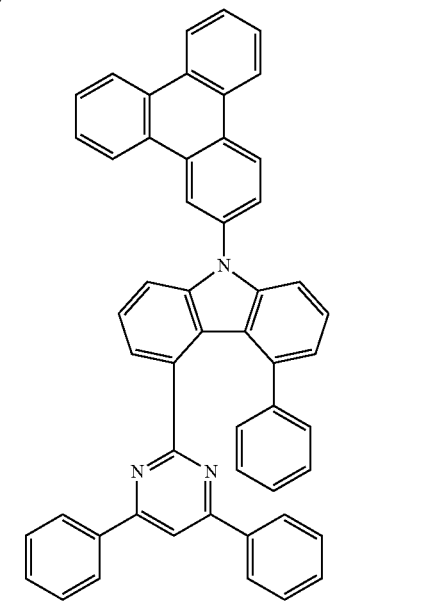
47
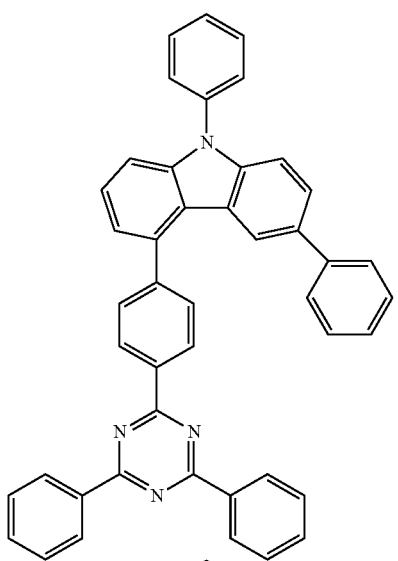
48
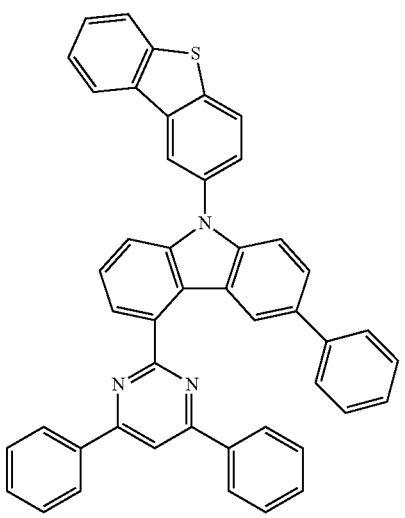
49
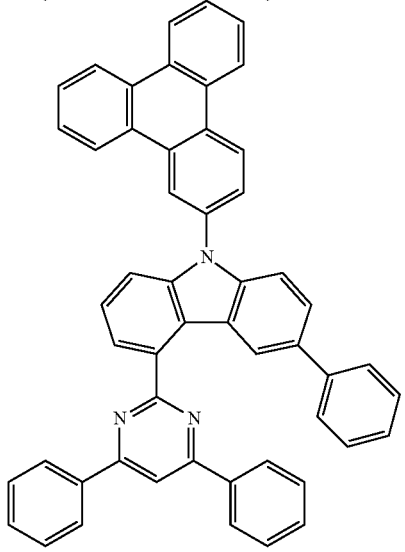
50
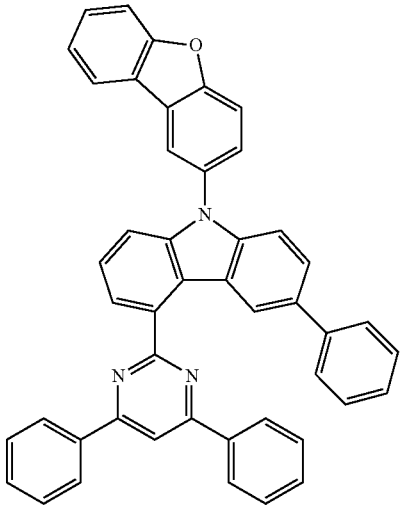

175 176
-continued
51
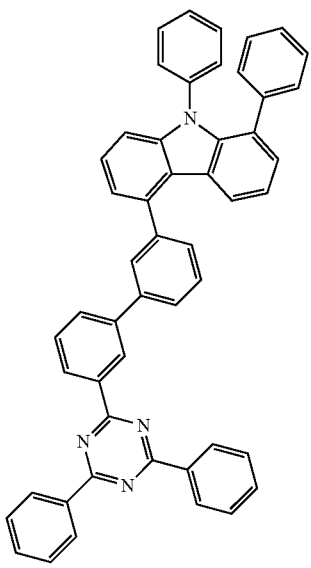
52
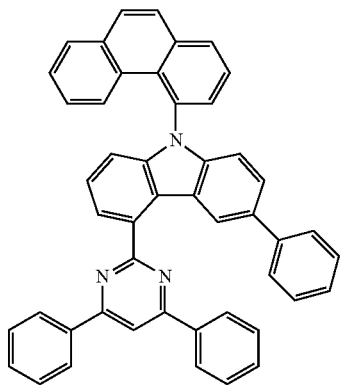
53
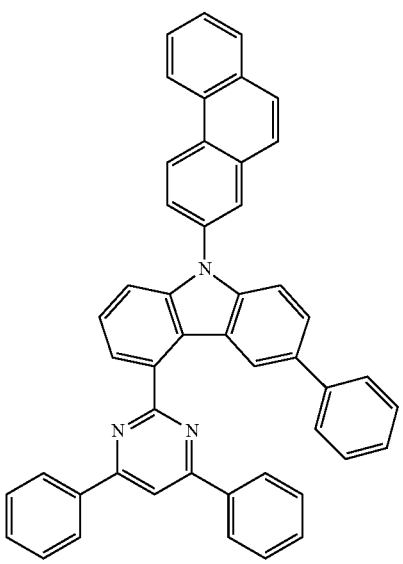
54
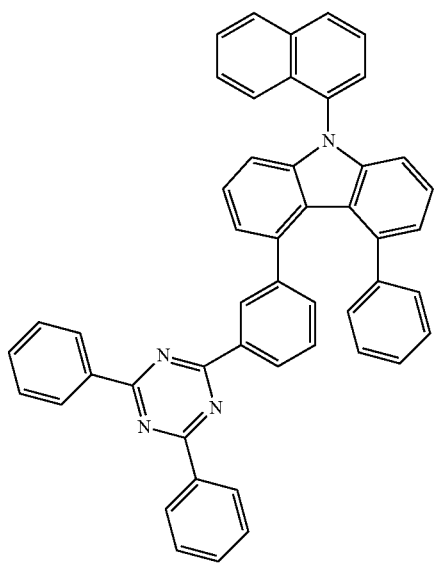
55
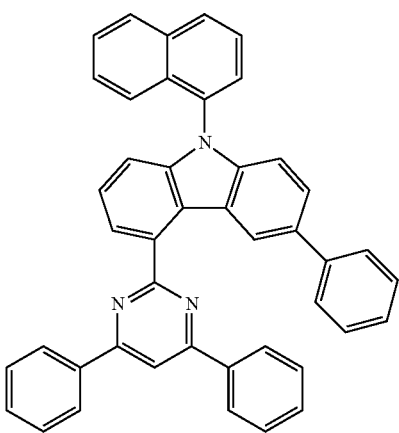
56
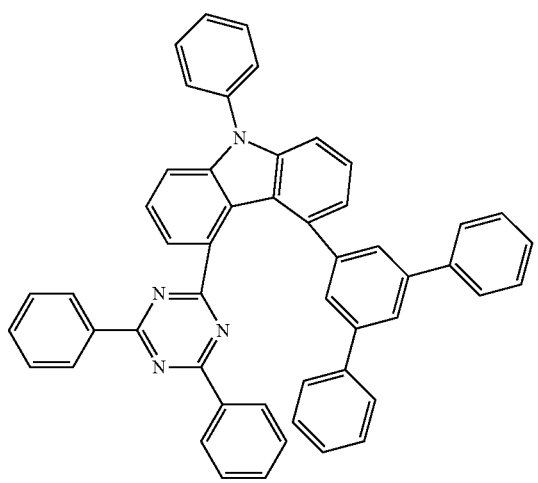

-continued
57
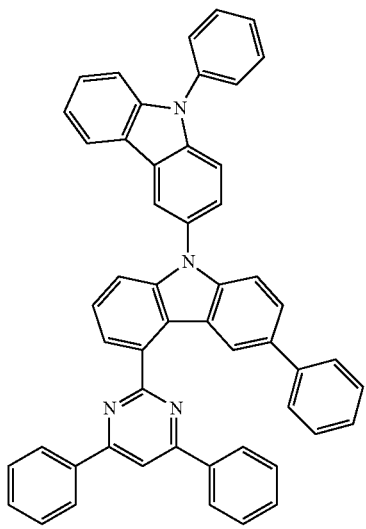
58
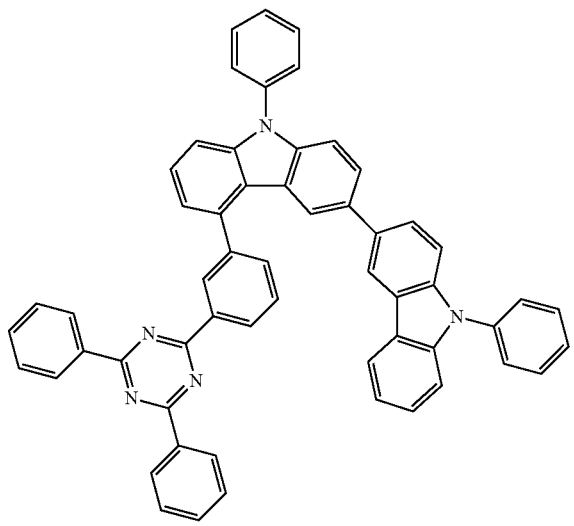
59
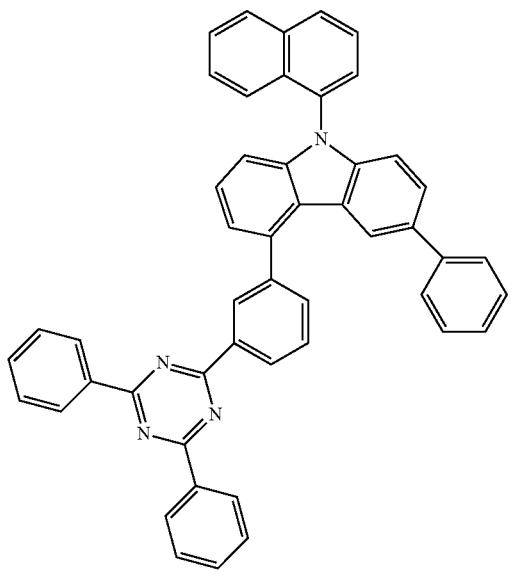
60
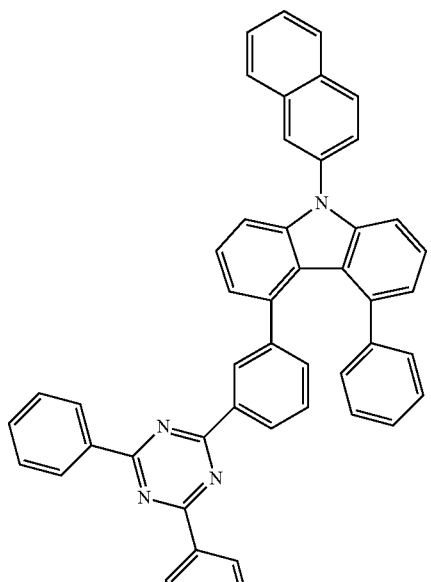
61
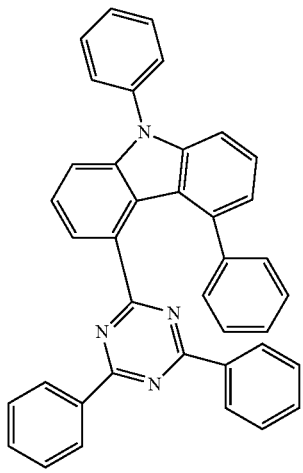
62
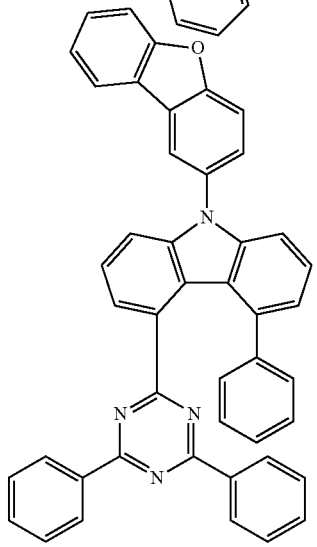

-continued
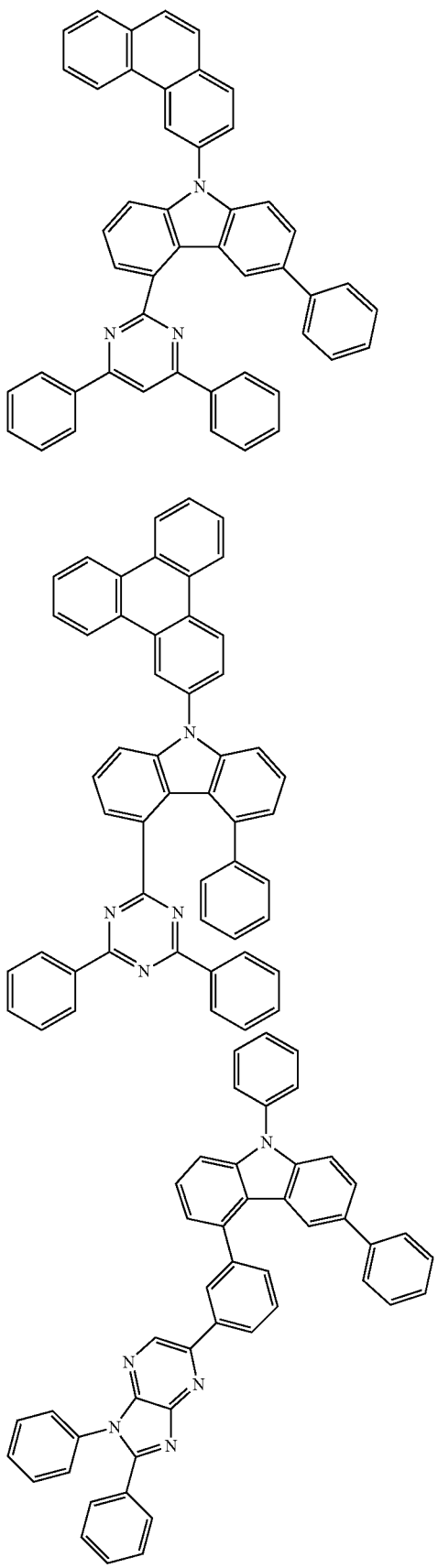
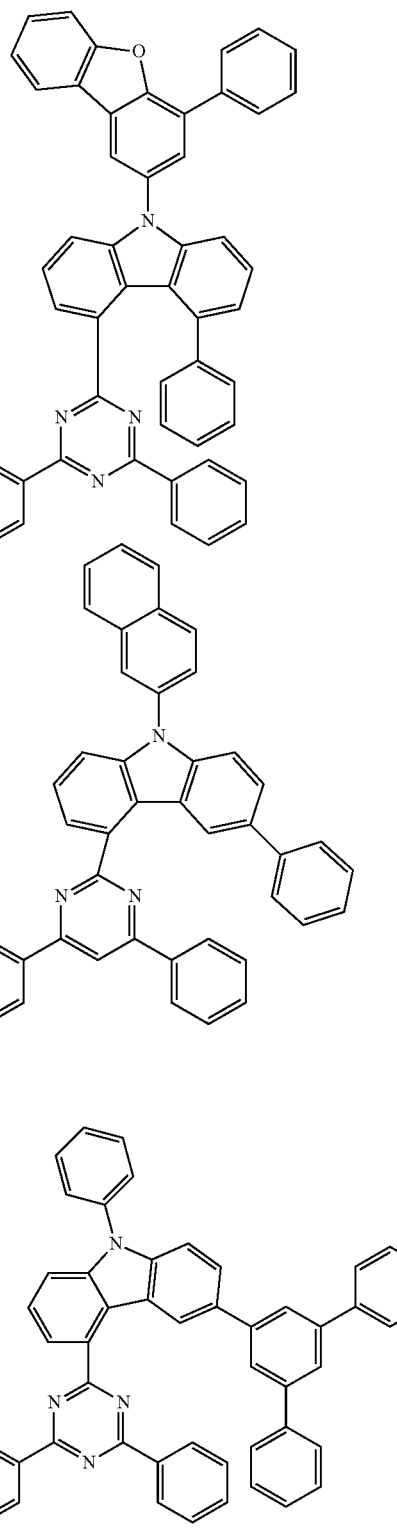

-continued
69
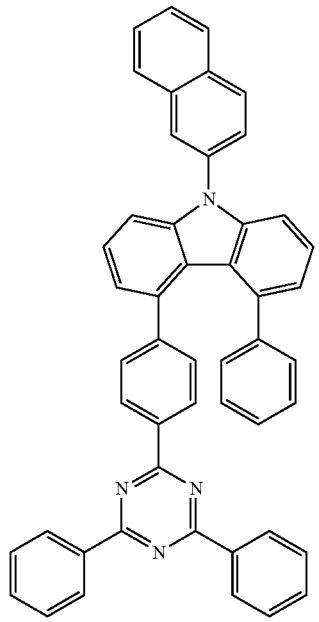
70
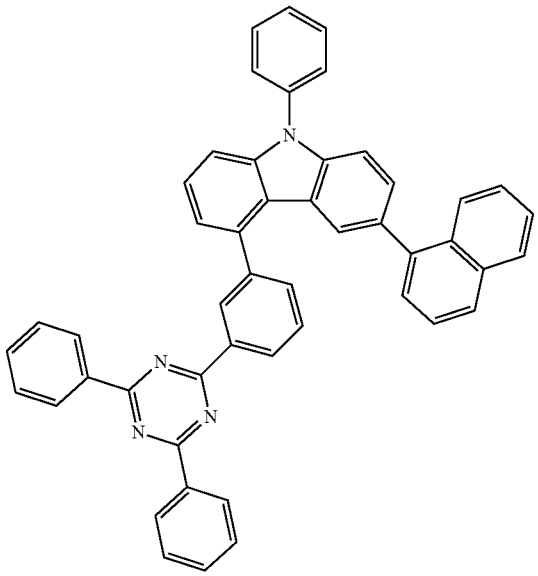
71
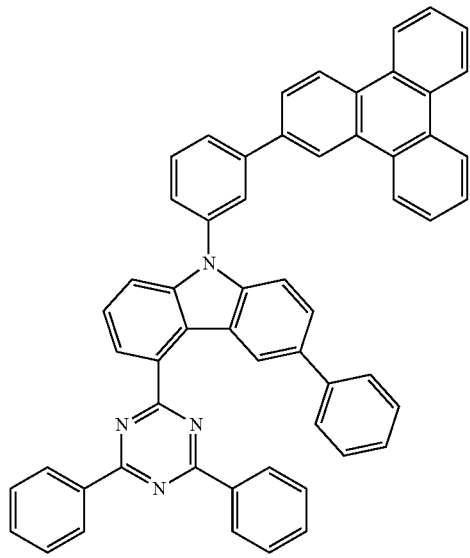
72
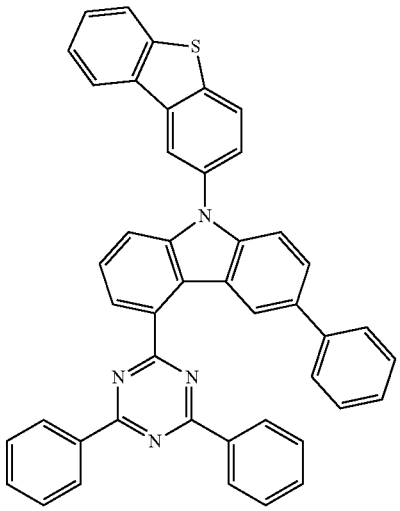

-continued
73
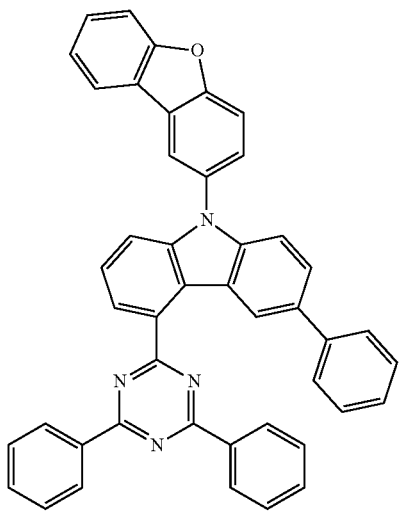
74
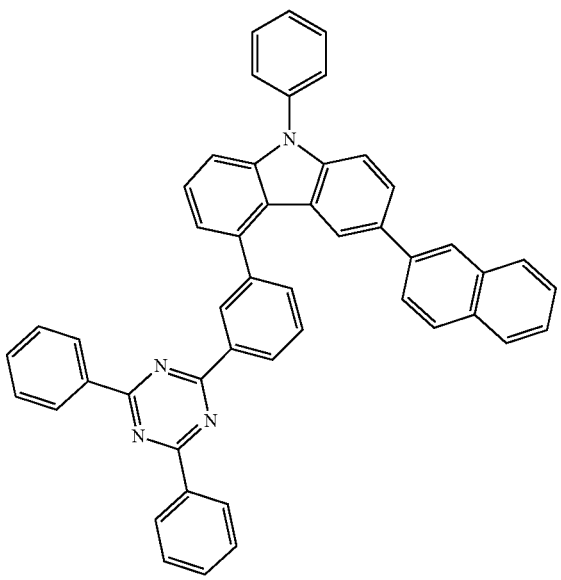
75
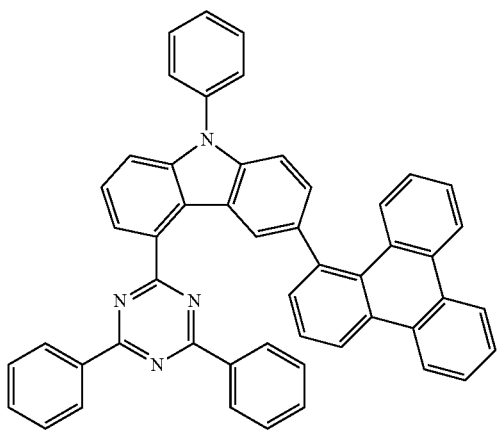
76
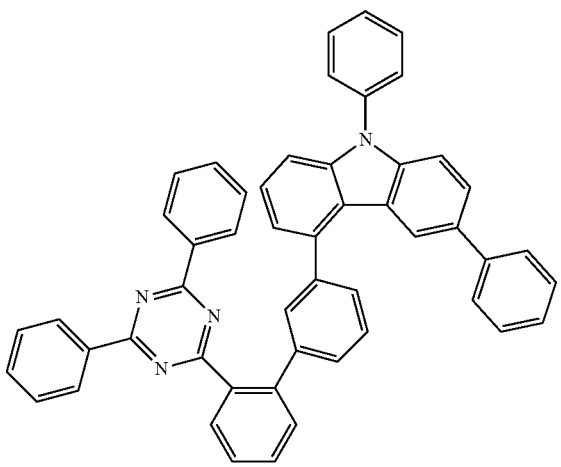
77
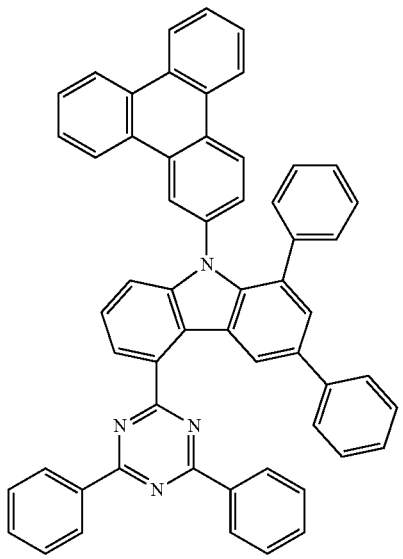
78
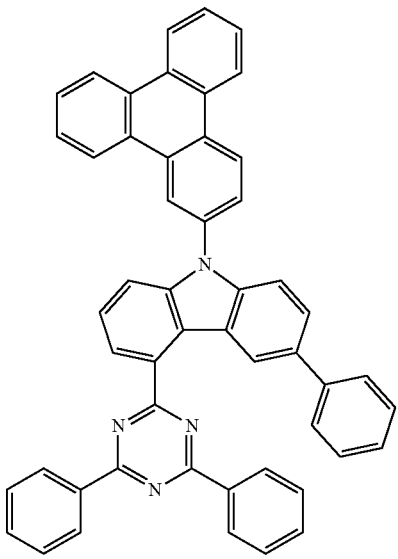

-continued
79
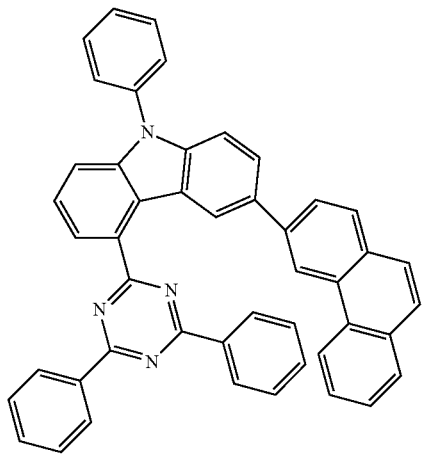
80
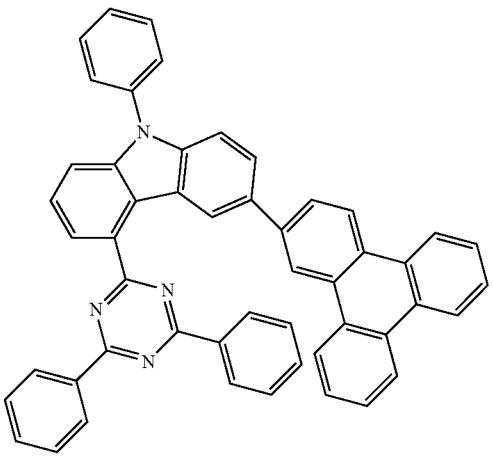
81
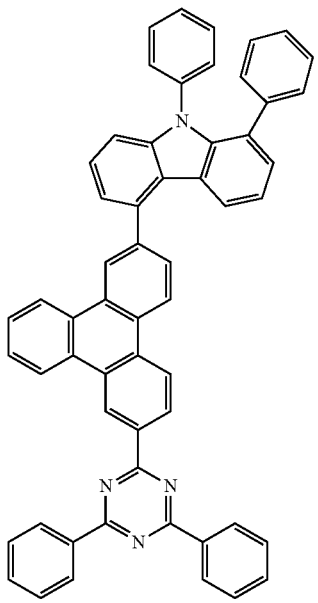
82
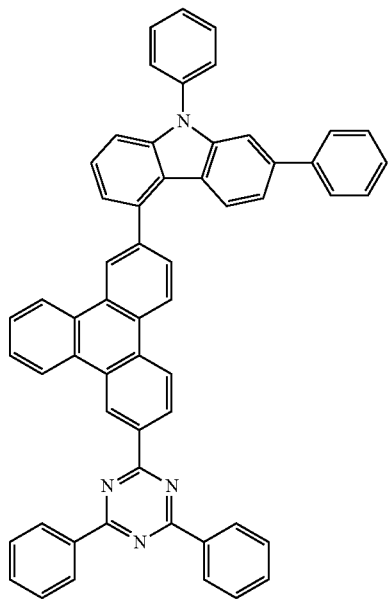
83
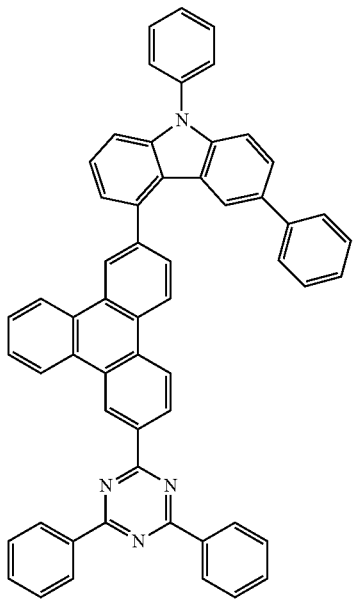
84
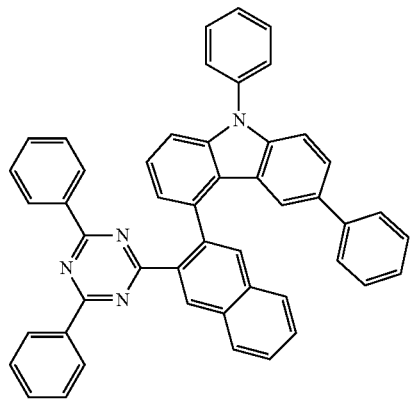

-continued
85
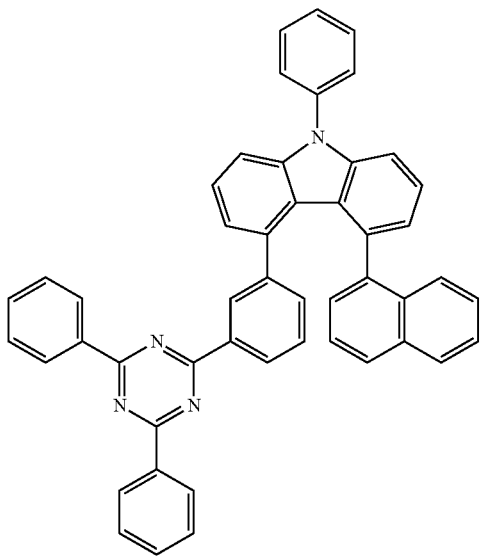
86
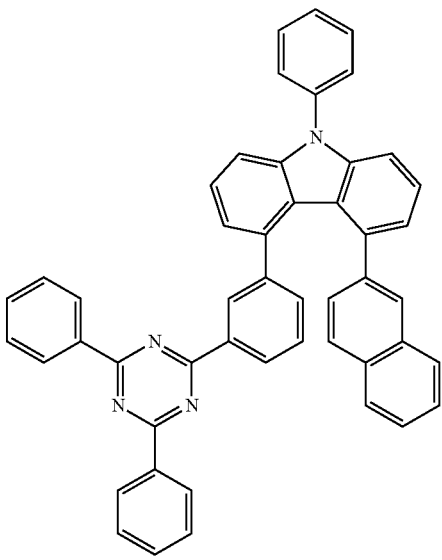
87
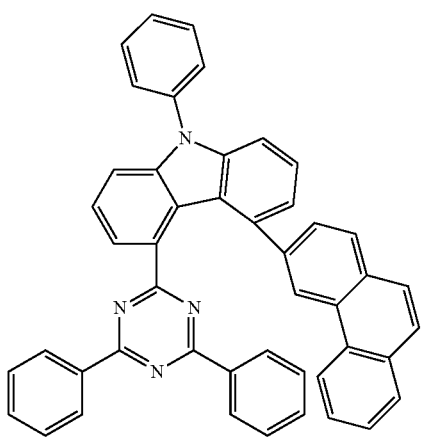
88
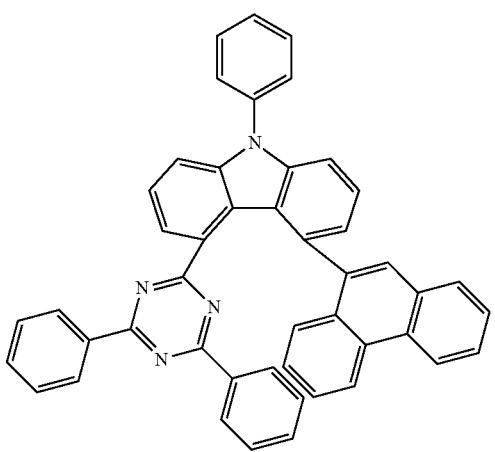
89
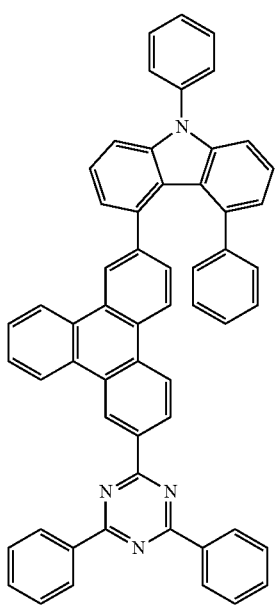
90
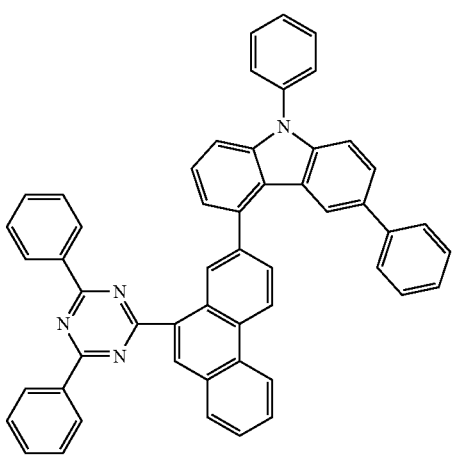

91
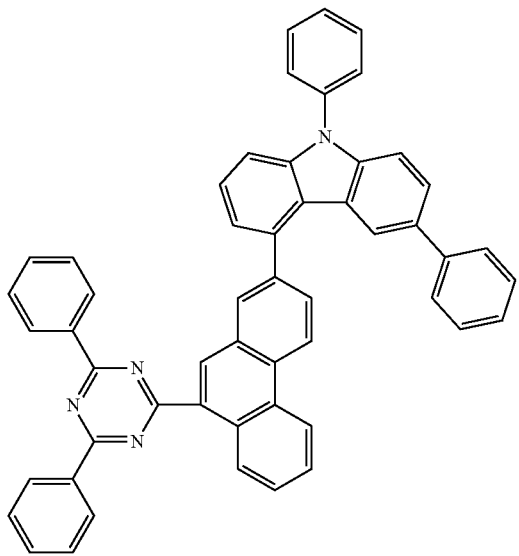
92
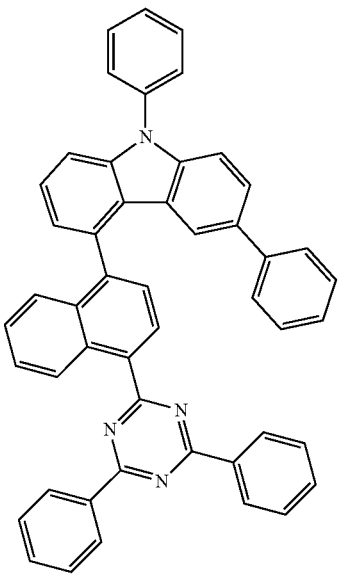
93
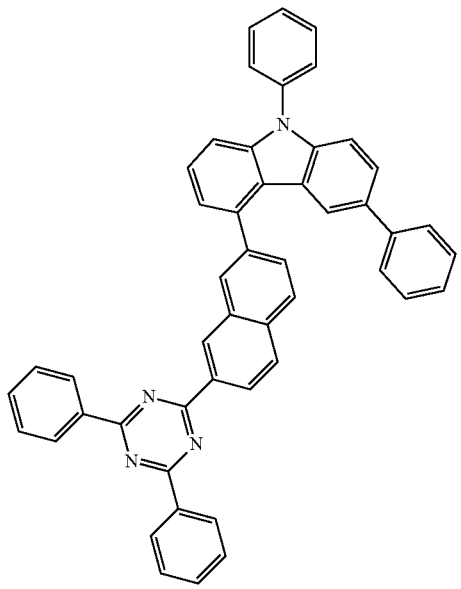
94
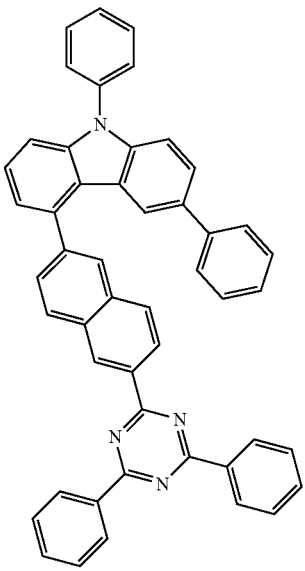

95
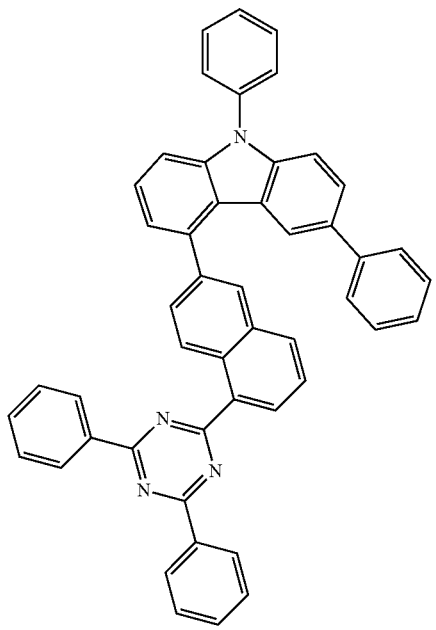
96
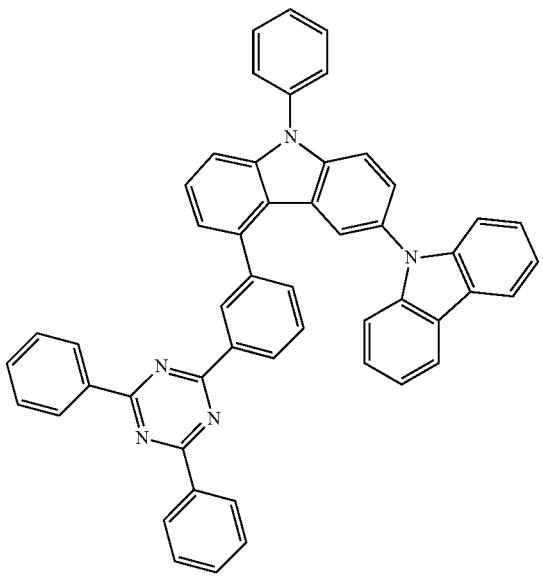
97
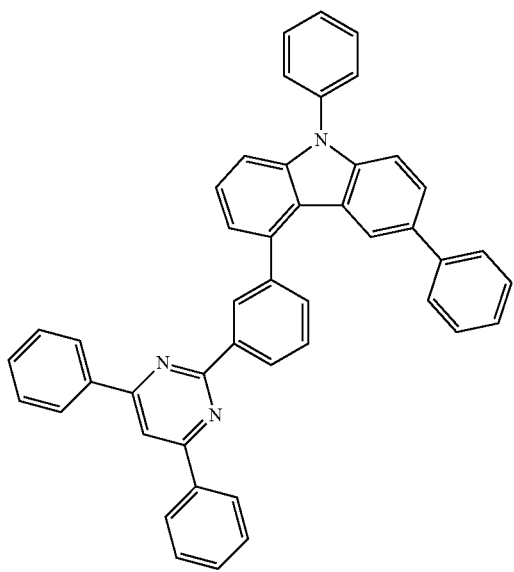
98

-continued
99
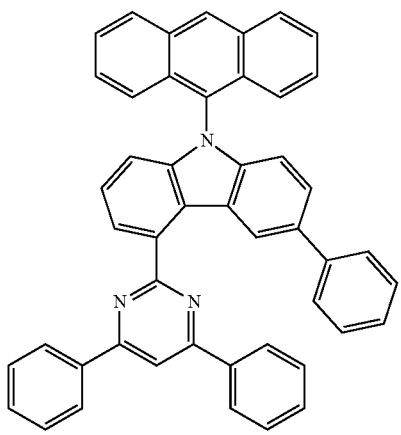
100
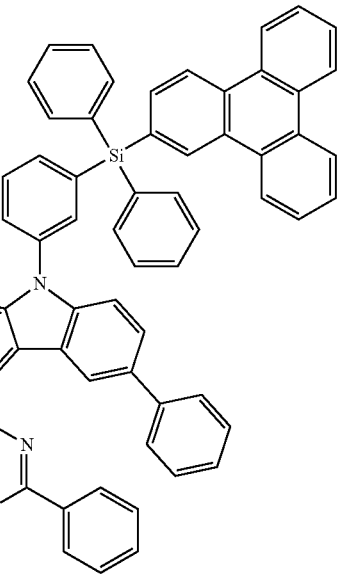
101
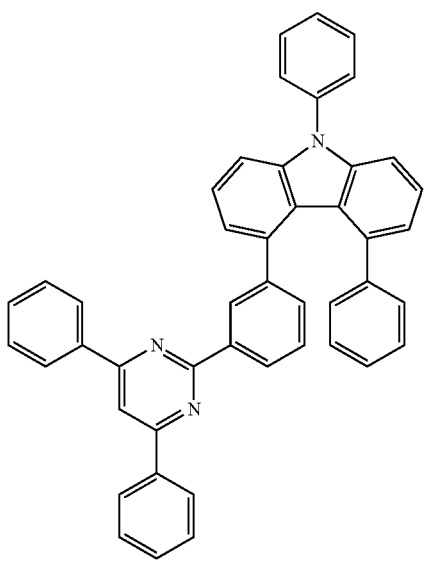
102
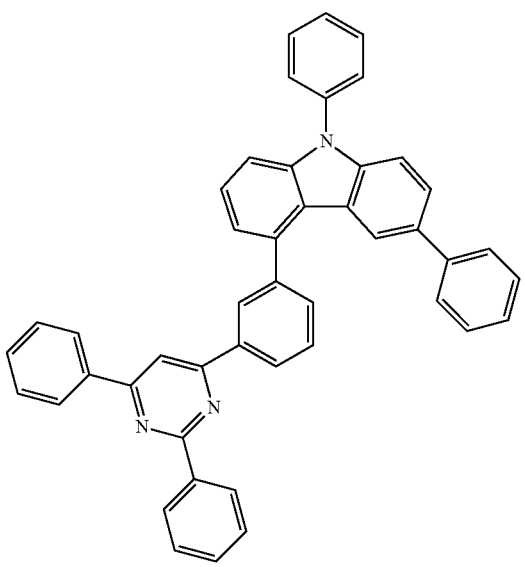
103
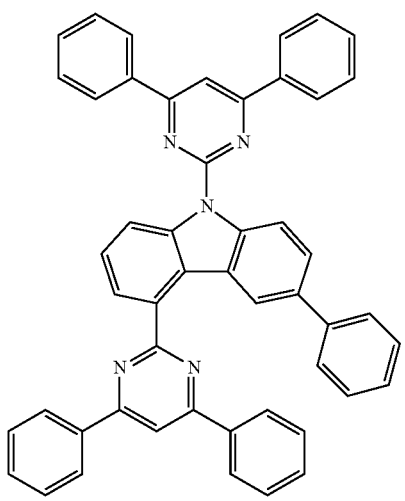
104
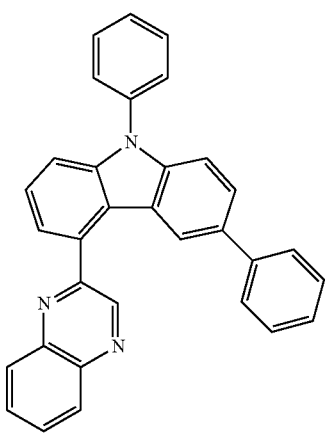

105
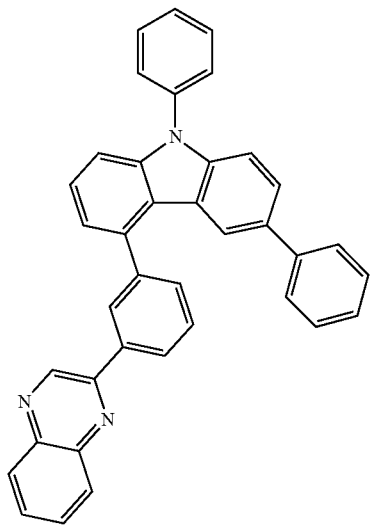
106
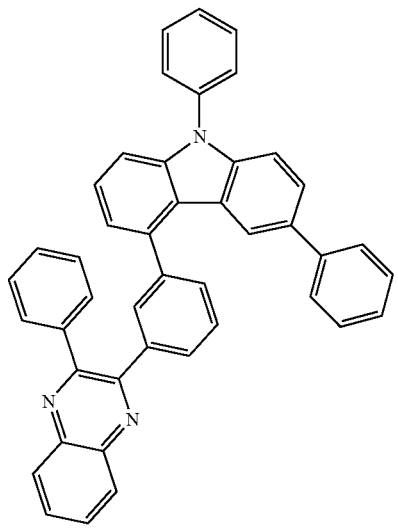
107
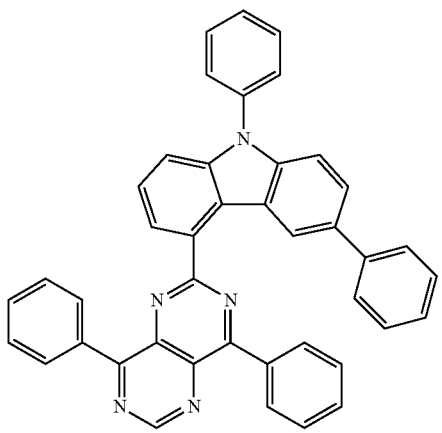
108
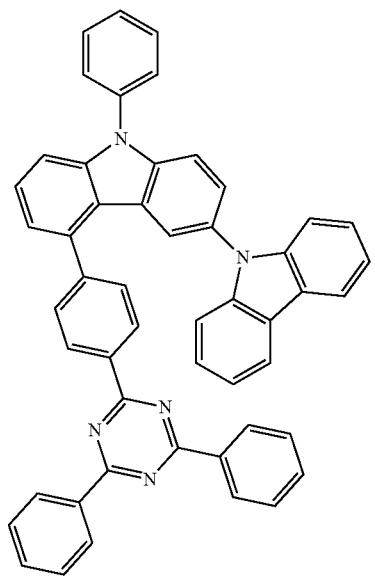
109
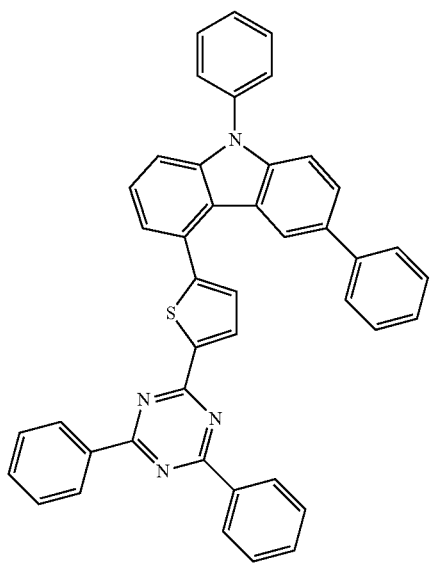
110
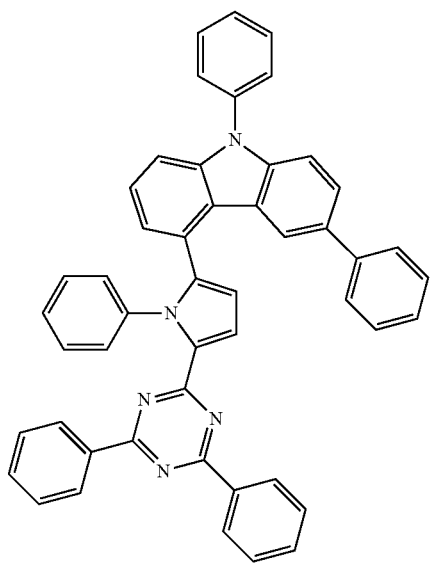

-continued
111
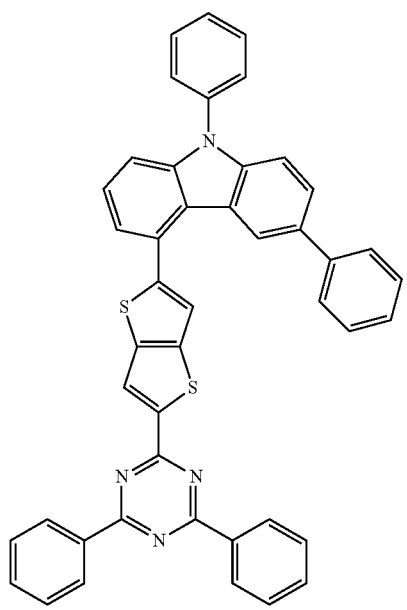
112
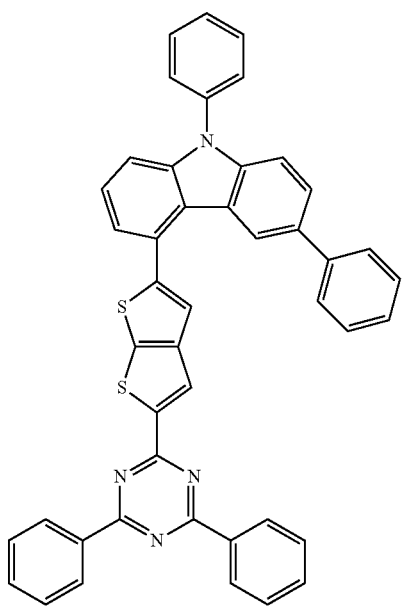
113
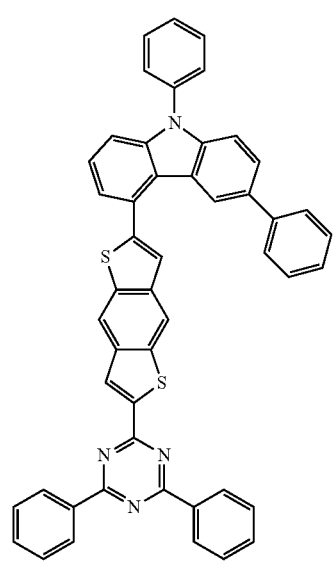
114
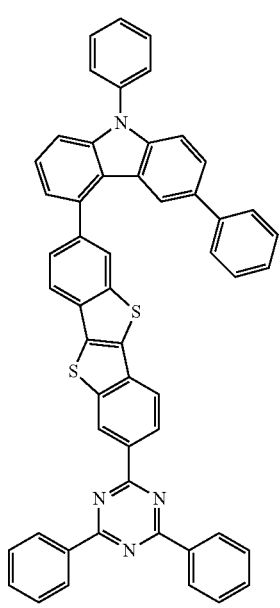

115
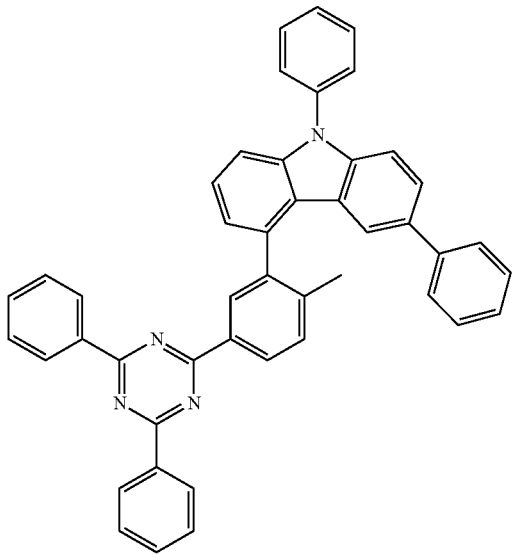
116
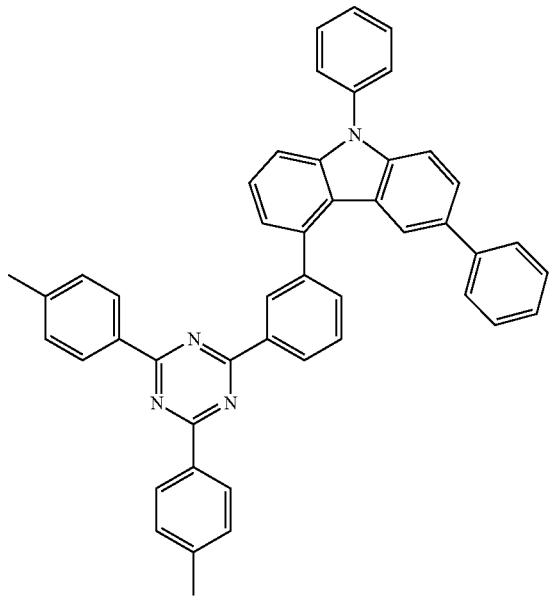
117
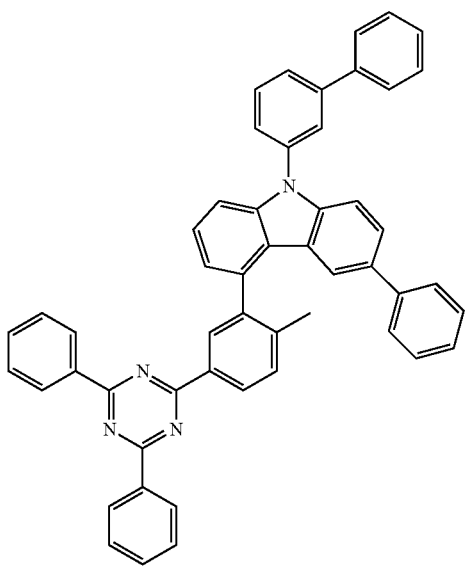
118
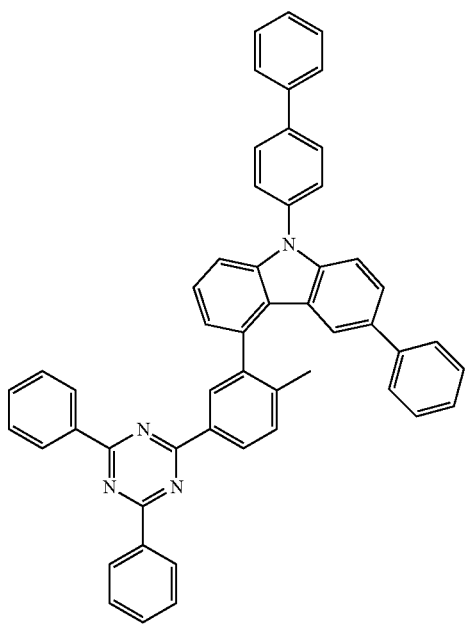

-continued
119
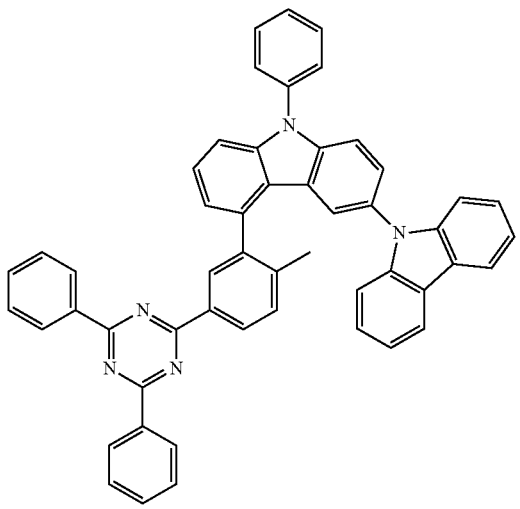
120
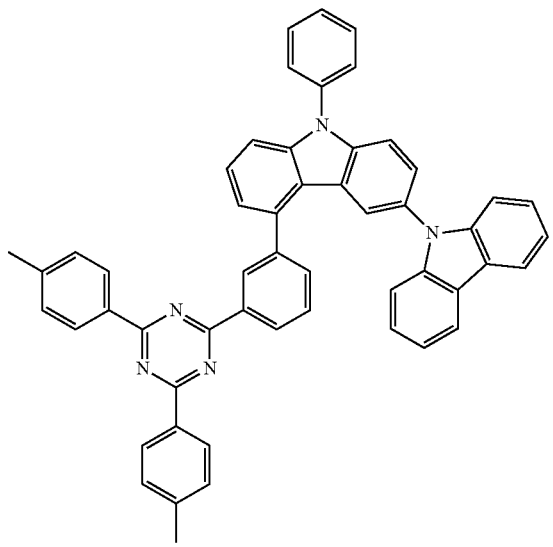
121
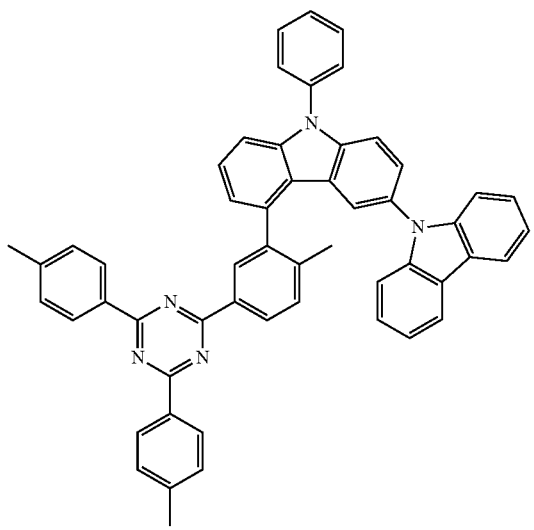
122
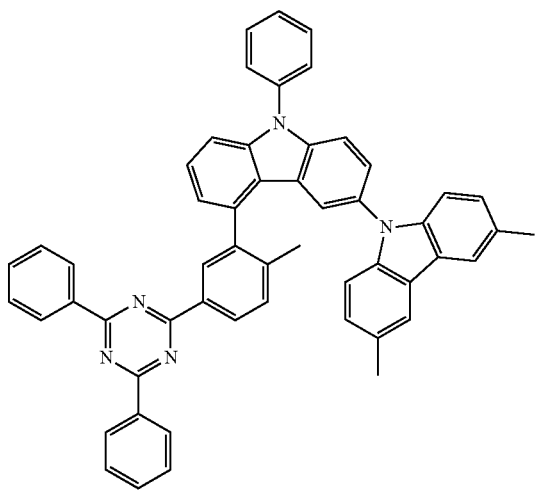
123
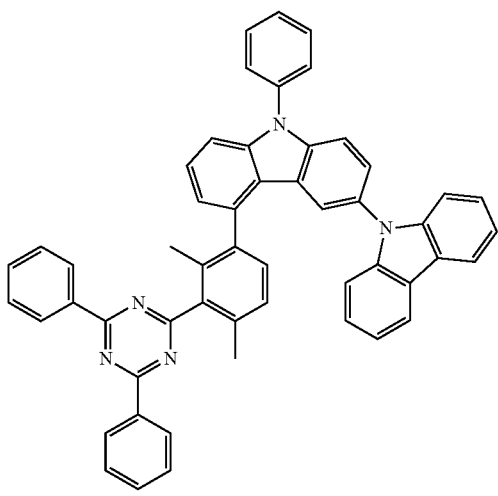
124
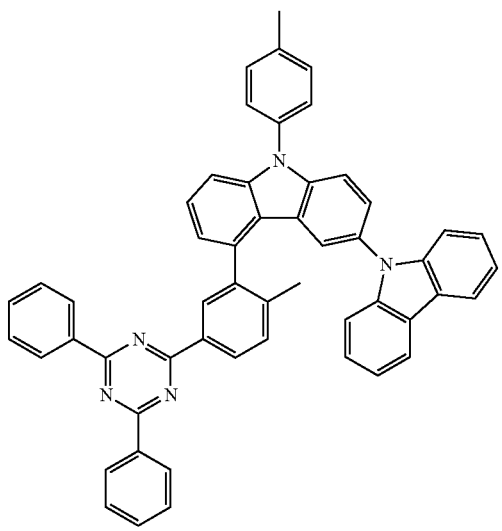

125
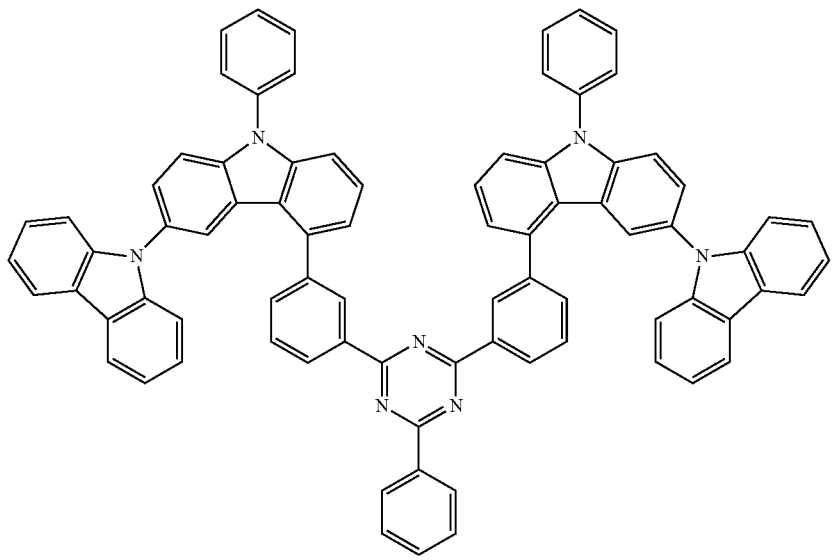
126
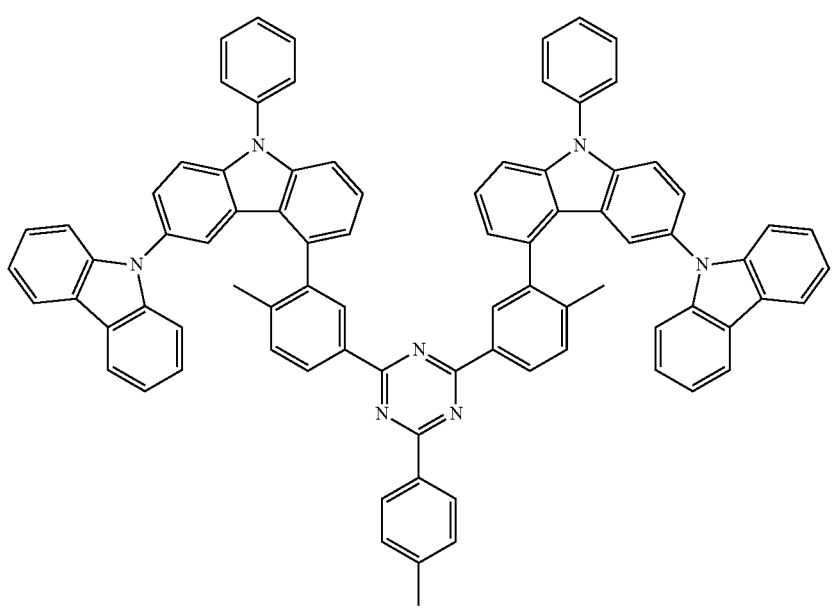

-continued
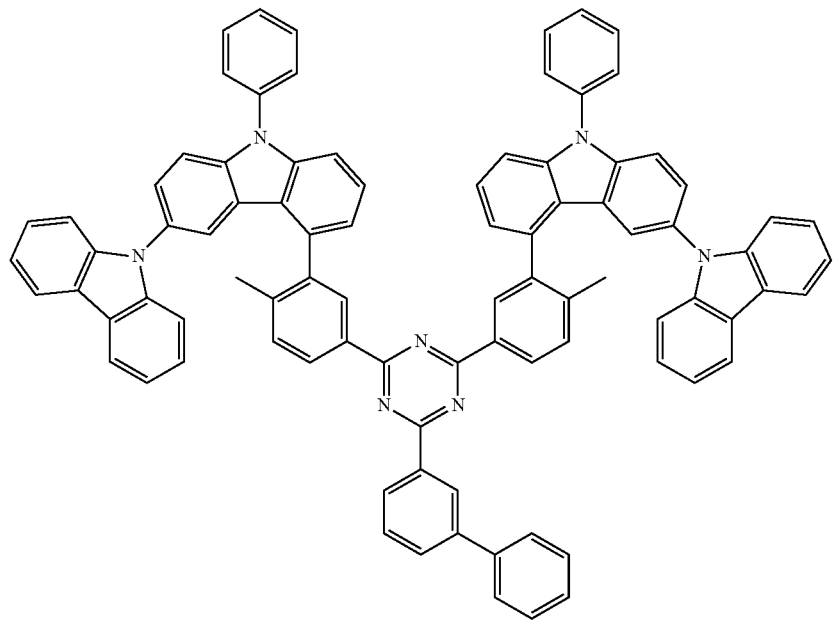
127
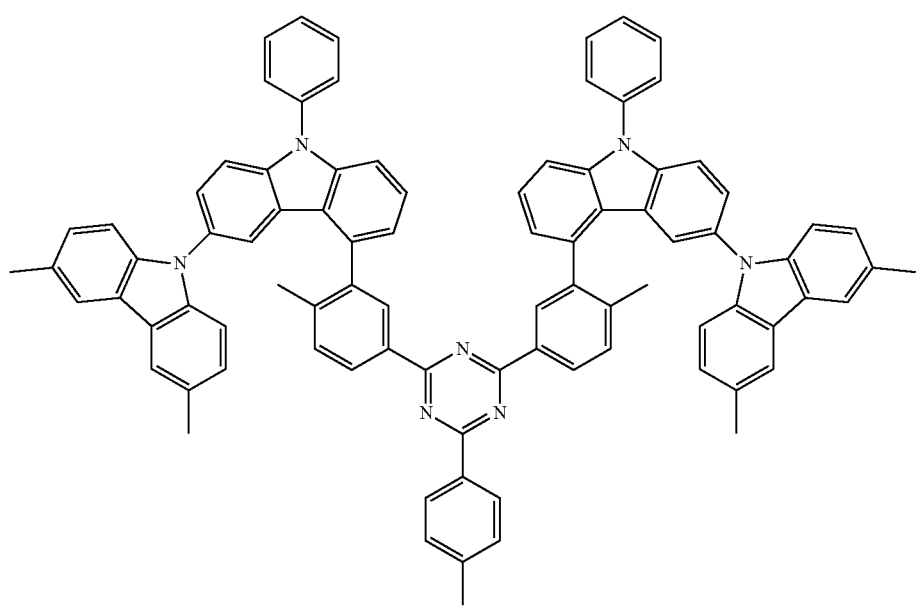
128

129

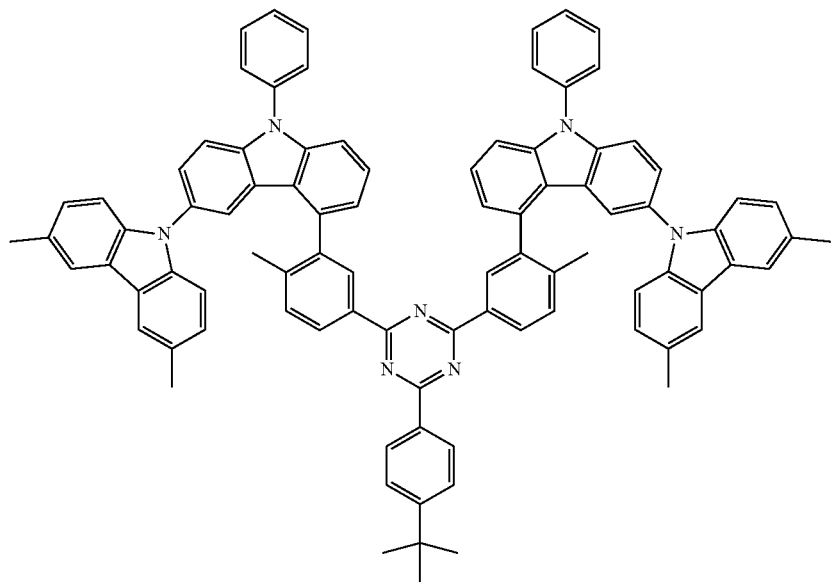

130

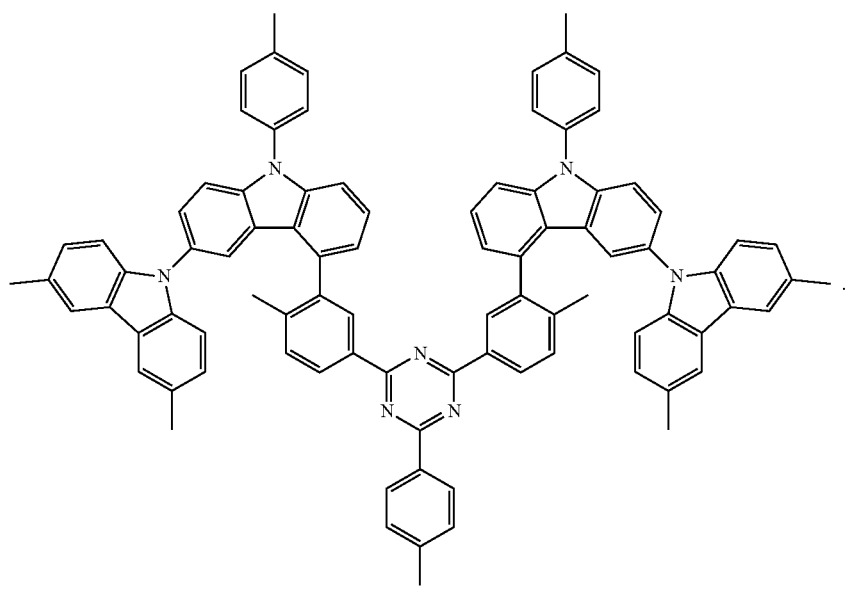

3. An organic light-emitting device comprising:
a first electrode;
a second electrode; and
an organic layer disposed between the first electrode and the second electrode,
wherein the organic layer comprises an emission layer and at least one of the carbazole-based compounds of claim 1.

4. The organic light-emitting device of claim 3, wherein
the first electrode is an anode,
the second electrode is a cathode, and
the organic layer comprises
i) a hole transport region disposed between the first electrode and the emission layer and comprising at least one of a hole injection layer, a hole transport layer, and an electron blocking layer, and
ii) an electron transport region disposed between the emission layer and the second electrode and comprising at least one of a hole blocking layer, an electron transport layer, and an electron injection layer.

5. The organic light-emitting device of claim 3, wherein the emission layer comprises at least one of the carbazole-based compounds.

6. The organic light-emitting device of claim 5, wherein the emission layer further comprises a phosphorescent dopant, and the at least one of the carbazole-based compound serves as a host.

7. The organic light-emitting device of claim 5, wherein the emission layer further comprises a phosphorescent dopant, and the dopant comprises an organometallic compound represented by Formula 81:

Formula 81

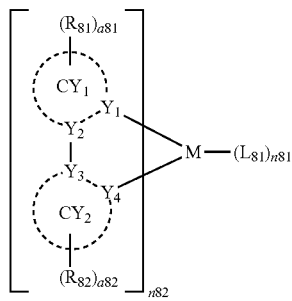

wherein, in Formula 81,

M is iridium, platinum, osmium, titanium, zirconium, hafnium, europium, terbium, or thulium, $Y_1$ to $Y_4$ are each independently a carbon or a nitrogen, wherein $Y_1$ and $Y_2$ are linked to each other via a single bond or a double bond, and $Y_3$ and $Y_4$ are linked to each other via a single bond or a double bond;

$CY_1$ and $CY_2$ are each independently a benzene, a naphthalene, a fluorene, a spiro-fluorene, an indene, a pyrrole, a thiophene, a furan, an imidazole, a pyrazole, a thiazole, an isothiazole, an oxazole, an isooxazole, a pyridine, a pyrazine, a pyrimidine, a pyridazine, a quinoline, an isoquinoline, a benzoquinoline, a quinoxaline, a quinazoline, a carbazole, a benzoimidazole, a benzofuran, a benzothiophene, an isobenzothiophene, a benzooxazole, an isobenzooxazole, a triazole, a tetrazole, an oxadiazole, a triazine, a dibenzofuran, or a dibenzothiophene, wherein $CY_1$ and $CY_2$ are optionally linked to each other via a single bond or an organic linking group;

$R_{81}$ and $R_{82}$ are each independently a hydrogen, a deuterium, —F, —Br, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —$SF_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent nonaromatic condensed polycyclic group, a substituted or unsubstituted monovalent nonaromatic condensed heteropolycyclic group, —$N(Q_1)(Q_2)$, —$Si(Q_3)(Q_4)(Q_5)$, or —$B(Q_6)(Q_7)$;

a81 and a82 are each independently an integer selected from 1 to 5;

n81 is an integer selected from 0 to 4;

n82 is 1, 2, or 3; and $L_{81}$ is a monovalent organic ligand, a divalent organic ligand, or a trivalent organic ligand.

8. An organic light-emitting device comprising:
a first electrode;
a second electrode; and
an organic layer disposed between the first electrode and the second electrode,
wherein the organic layer comprises an emission layer and at least one of the carbazole-based compounds of claim 2.

* * * * *